US012539244B2

(12) United States Patent
Lim et al.

(10) Patent No.: US 12,539,244 B2
(45) Date of Patent: Feb. 3, 2026

(54) SURGICAL GANTRY AND INTERFACE MOVEABLY INTERCONNECTING SURGICAL TABLE AND GANTRY

(71) Applicant: Warsaw Orthopedic, Inc., Warsaw, IN (US)

(72) Inventors: Roy K. Lim, Memphis, TN (US); Katharine E. Darling, Louisville, CO (US); Mark C. Dace, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 18/670,669

(22) Filed: May 21, 2024

(65) Prior Publication Data

US 2024/0390206 A1 Nov. 28, 2024

Related U.S. Application Data

(60) Provisional application No. 63/469,139, filed on May 26, 2023.

(51) Int. Cl.

*A61G 13/10* (2006.01)
*A61B 34/30* (2016.01)

(Continued)

(52) U.S. Cl.

CPC ............ *A61G 13/101* (2013.01); *A61B 34/30* (2016.02); *A61G 13/0054* (2016.11); *A61G 13/08* (2013.01); *A61G 2200/325* (2013.01)

(58) Field of Classification Search

CPC ...... A61G 13/04; A61G 13/08; A61G 13/123; A61G 13/122; A61G 13/0054; A61G 2200/325; A61G 13/1245; A61G 13/0036; A61G 13/104; A61G 13/06; A61G 13/101; A61B 6/0407; A61B 34/30; A61B 6/0487;

(Continued)

(56) References Cited

U.S. PATENT DOCUMENTS 1,171,713 A 2/1916 Gilkerson
2,691,979 A 10/1954 Watson (Continued)

FOREIGN PATENT DOCUMENTS

CN 200945223 9/2007
CN 212140458 12/2015

(Continued)

OTHER PUBLICATIONS

Top Design Multi Functional Operating Table 5 Major Hydraulic Price, alibaba.com (https://www.alibaba.com/product-detail/Top-Design-Multi-Functional-Operating-Table_160008926290.html).

(Continued)

*Primary Examiner* — Madison Emanski

(57) ABSTRACT

A combination of a surgical table, a gantry including surgical robotic arms, and an interface for moveably interconnecting a surgical table with the gantry is provided. The surgical table can support a patient thereon, the gantry can support one or more surgical robotic arms for performing and/or aiding the performance of surgery on the patient, and the interface can be used to move the surgical table and the patient supported thereby relative to the surgical robotic arms.

20 Claims, 39 Drawing Sheets

(51) Int. Cl.
*A61G 13/00* (2006.01)
*A61G 13/08* (2006.01)

(58) Field of Classification Search
CPC .................... A61B 50/13; A61B 90/57; A61B 2017/00477; A61B 2090/571; A61B 90/50; A61B 2560/0437; A61B 34/20; A61B 2034/2055; A61B 2034/2063; A61B 34/35; A61B 34/32; A61B 34/70; B25J 9/0009; B25J 9/0096
See application file for complete search history.

(56) References Cited

U.S. PATENT DOCUMENTS

| | | | |
|---|---|---|---|
| 3,060,925 | A | 10/1962 | Honsaker et al. |
| 3,227,440 | A | 1/1966 | Scott |
| 3,293,667 | A | 12/1966 | Ohrberg |
| 3,306,287 | A | 2/1967 | Arp |
| 3,362,704 | A | 1/1968 | Pilz |
| 3,389,702 | A | 6/1968 | Kennedy |
| 3,828,377 | A | 8/1974 | Fary, Sr. |
| 4,029,089 | A | 6/1977 | Mulhlland |
| 4,144,880 | A | 3/1979 | Daniels |
| 4,194,257 | A | 3/1980 | Martin et al. |
| 4,627,119 | A | 12/1986 | Hachey et al. |
| 4,655,200 | A | 4/1987 | Knight |
| 4,705,026 | A | 11/1987 | Chaussy |
| 4,866,796 | A | 9/1989 | Robinson |
| 4,872,656 | A | 10/1989 | Brendgord |
| 4,901,384 | A | 2/1990 | Eary |
| 4,915,101 | A | 4/1990 | Cuccia |
| 5,009,407 | A | 4/1991 | Watanabe |
| 5,013,018 | A | 5/1991 | Sicek |
| 5,088,706 | A | 2/1992 | Jackson |
| 5,103,511 | A | 4/1992 | Sequin |
| 5,131,106 | A | 7/1992 | Jackson |
| 5,231,719 | A | 8/1993 | Schnelle |
| 5,279,011 | A | 1/1994 | Schnelle |
| 5,362,302 | A | 11/1994 | Jenson et al. |
| 5,390,383 | A | 2/1995 | Carn |
| 5,410,769 | A | 5/1995 | Waterman |
| 5,444,882 | A | 8/1995 | Andrews |
| 5,477,570 | A | 12/1995 | Hannant et al. |
| 5,493,741 | A | 2/1996 | Baer |
| 5,564,662 | A | 10/1996 | Lussi et al. |
| 5,613,254 | A | 3/1997 | Clayman |
| 5,621,932 | A | 4/1997 | Strachan |
| 5,642,302 | A | 6/1997 | Dumont |
| 5,860,899 | A | 1/1999 | Rassman |
| 5,991,651 | A | 11/1999 | LaBarbera |
| 6,003,176 | A | 12/1999 | Wasley |
| 6,076,525 | A | 6/2000 | Hoffman |
| 6,101,644 | A | 8/2000 | Gagneur et al. |
| 6,112,349 | A | 9/2000 | Connolly |
| 6,154,901 | A | 12/2000 | Carr |
| 6,260,220 | B1 | 7/2001 | Lamb |
| 6,295,666 | B1 | 10/2001 | Takaura |
| 6,295,671 | B1 | 10/2001 | Reesby et al. |
| 6,311,349 | B1 | 11/2001 | Kazakia |
| 6,367,104 | B1 | 4/2002 | Fallbo, Sr. et al. |
| 6,378,149 | B1 | 4/2002 | Sanders et al. |
| 6,516,483 | B1 | 2/2003 | VanSteenburg |
| 6,566,833 | B2 | 5/2003 | Barlett |
| 6,615,430 | B2 | 9/2003 | Heimbrock |
| 6,671,905 | B2 | 1/2004 | Bartlett et al. |
| 6,681,423 | B2 | 1/2004 | Zachrisson |
| 6,701,553 | B1 | 3/2004 | Hand et al. |
| 6,701,554 | B2 | 3/2004 | Heimbrock |
| 6,701,558 | B2 | 3/2004 | VanSteenburg |
| 6,715,169 | B2 | 4/2004 | Niederkrom |
| 6,718,571 | B2 | 4/2004 | Bartels |
| 6,728,983 | B2 | 5/2004 | Bartlett et al. |
| 6,732,390 | B2 | 5/2004 | Krywiczanin |
| 6,739,006 | B2 | 5/2004 | Borders et al. |
| 6,820,621 | B2 | 11/2004 | DeMayo |
| 6,874,181 | B1 | 4/2005 | Connolly et al. |
| 6,928,676 | B1 | 8/2005 | Schwaegerle |
| 6,934,986 | B2 | 8/2005 | Krywiczanin et al. |
| 6,941,951 | B2 | 9/2005 | Hubert et al. |
| 6,966,081 | B1 | 11/2005 | Sharps |
| 7,100,225 | B1 | 9/2006 | Bailey |
| 7,120,223 | B2 | 10/2006 | Nafstadius |
| 7,152,261 | B2 | 12/2006 | Jackson |
| 7,181,791 | B2 | 2/2007 | Clayton |
| 7,189,214 | B1 | 3/2007 | Saunders |
| 7,219,379 | B2 | 5/2007 | Krywiczanin et al. |
| 7,234,180 | B2 | 6/2007 | Horton et al. |
| 7,257,849 | B2 | 8/2007 | Jahrling |
| 7,290,302 | B2 | 11/2007 | Sharps |
| 7,343,635 | B2 | 3/2008 | Jackson |
| 7,426,930 | B1 | 9/2008 | Bailey |
| 7,472,440 | B2 | 1/2009 | Bartlett et al. |
| 7,484,253 | B1 | 2/2009 | Coppens |
| 7,496,980 | B2 | 3/2009 | Sharps |
| 7,565,708 | B2 | 7/2009 | Jackson |
| 7,600,281 | B2 | 10/2009 | Skripps |
| 7,669,262 | B2 | 3/2010 | Skripps |
| 7,739,762 | B2 | 6/2010 | Lamb et al. |
| 7,757,316 | B2 | 7/2010 | Koch |
| 7,810,185 | B2 | 10/2010 | Burstner et al. |
| 7,882,583 | B2 | 2/2011 | Skripps |
| 8,060,960 | B2 | 11/2011 | Jackson |
| 8,117,694 | B2 | 2/2012 | Farooqui |
| 8,118,029 | B2 | 2/2012 | Gneiting et al. |
| 8,286,283 | B2 | 10/2012 | Copeland et al. |
| 8,286,637 | B2 | 10/2012 | Kaska |
| 8,381,331 | B2 | 2/2013 | Sharps et al. |
| 8,381,335 | B2 | 2/2013 | Ahlman |
| 8,413,660 | B2 | 4/2013 | Weinstein et al. |
| 8,424,133 | B1 | 4/2013 | Rossi |
| 8,439,948 | B1 | 5/2013 | King |
| 8,443,473 | B2 | 5/2013 | Maxwell |
| 8,584,281 | B2 | 11/2013 | Diel et al. |
| 8,635,725 | B2 | 1/2014 | Tannoury et al. |
| 8,677,529 | B2 | 3/2014 | Jackson |
| 8,707,484 | B2 | 4/2014 | Jackson et al. |
| 8,978,180 | B2 | 3/2015 | Jackson |
| 9,072,646 | B2 | 7/2015 | Skripps et al. |
| 9,180,062 | B2 | 11/2015 | Jackson |
| 9,186,291 | B2 | 11/2015 | Jackson et al. |
| 9,226,865 | B2 | 1/2016 | Jackson et al. |
| 9,265,680 | B2 | 2/2016 | Sharps |
| 9,295,433 | B2 | 3/2016 | Jackson et al. |
| 9,308,145 | B2 | 4/2016 | Jackson |
| 9,339,430 | B2 | 5/2016 | Jackson et al. |
| 9,358,170 | B2 | 6/2016 | Jackson |
| 9,402,775 | B2 | 8/2016 | Jackson et al. |
| 9,414,982 | B2 | 8/2016 | Jackson |
| 9,468,576 | B2 | 10/2016 | Jackson |
| 9,480,615 | B2 | 11/2016 | Eisenmann |
| 9,498,397 | B2 | 11/2016 | Hight et al. |
| 9,522,078 | B2 | 12/2016 | Pizzini |
| 9,554,959 | B2 | 1/2017 | Carn |
| 9,622,928 | B2 | 4/2017 | Jackson et al. |
| 9,642,760 | B2 | 5/2017 | Jackson et al. |
| 9,655,793 | B2 | 5/2017 | Hertz |
| 9,700,476 | B2 | 7/2017 | Hoel et al. |
| 9,713,562 | B2 | 7/2017 | Perlman et al. |
| 9,744,089 | B2 | 8/2017 | Jackson |
| 9,849,054 | B2 | 12/2017 | Jackson |
| 9,861,326 | B2 | 1/2018 | Koerth et al. |
| 9,925,101 | B2 | 3/2018 | Kuenzler |
| 9,937,006 | B2 | 4/2018 | Skripps et al. |
| 9,993,380 | B2 | 6/2018 | Jackson |
| 10,136,863 | B2 | 11/2018 | Kaiser et al. |
| 10,238,559 | B1 | 3/2019 | Khaligh |
| 10,314,758 | B2 | 6/2019 | Dolliver et al. |
| 10,342,722 | B2 | 7/2019 | Garrido |
| 10,383,779 | B2 | 8/2019 | Koch |
| RE47,588 | E | 9/2019 | Erbel et al. |
| 10,406,054 | B1 | 9/2019 | Scholl et al. |
| 10,426,684 | B2 | 10/2019 | Dubois et al. |
| 10,492,973 | B2 | 12/2019 | Drake |
| 10,531,998 | B2 | 1/2020 | Jackson et al. |

(56) References Cited

U.S. PATENT DOCUMENTS

| | | | |
|---|---|---|---|
| 10,543,142 | B2 | 1/2020 | Lim et al. |
| 10,548,796 | B2 | 2/2020 | Lim et al. |
| 10,576,006 | B2 | 3/2020 | Lim et al. |
| 10,695,252 | B2 | 6/2020 | Jackson |
| 10,722,413 | B2 | 7/2020 | Lim et al. |
| 10,729,607 | B2 | 8/2020 | Jackson |
| 10,751,240 | B2 | 8/2020 | Lim et al. |
| 10,835,438 | B2 | 11/2020 | Jackson |
| 10,835,439 | B2 | 11/2020 | Lim et al. |
| 10,849,809 | B2 | 12/2020 | Lim et al. |
| 10,874,570 | B2 | 12/2020 | Lim et al. |
| 10,881,570 | B2 | 1/2021 | Lim et al. |
| 10,888,484 | B2 | 1/2021 | Lim et al. |
| 10,893,996 | B2 | 1/2021 | Lim et al. |
| 10,898,401 | B2 | 1/2021 | Lim et al. |
| 10,900,448 | B2 | 1/2021 | Lim et al. |
| 11,096,853 | B2 | 8/2021 | Hight et al. |
| 11,452,656 | B2 | 9/2022 | Campbell |
| 11,925,586 | B2 | 3/2024 | Lim |
| 2002/0138905 | A1 | 10/2002 | Barltett et al. |
| 2002/0138906 | A1 | 10/2002 | Barltett et al. |
| 2002/0157186 | A1 | 10/2002 | VanSteenburg |
| 2003/0140419 | A1 | 7/2003 | Barltett et al. |
| 2003/0140420 | A1 | 7/2003 | Niederkrom |
| 2003/0145382 | A1 | 8/2003 | Krywiczanin |
| 2003/0178027 | A1 | 9/2003 | DeMayo et al. |
| 2004/0010849 | A1 | 1/2004 | Krywiczanin et al. |
| 2004/0133979 | A1 | 7/2004 | Newkirk et al. |
| 2004/0133983 | A1 | 7/2004 | Newkirk |
| 2005/0015878 | A1 | 1/2005 | Bannister et al. |
| 2005/0181917 | A1 | 8/2005 | Dayal |
| 2006/0037141 | A1 | 2/2006 | Krywiczanin et al. |
| 2006/0123546 | A1 | 6/2006 | Horton |
| 2006/0162076 | A1 | 7/2006 | Bartlett et al. |
| 2006/0162084 | A1 | 7/2006 | Mezue |
| 2006/0185090 | A1 | 8/2006 | Jackson |
| 2006/0185091 | A1 | 8/2006 | Jackson |
| 2007/0107122 | A1 | 5/2007 | Georgi et al. |
| 2007/0107125 | A1 | 5/2007 | Koch et al. |
| 2008/0034502 | A1 | 2/2008 | Copeland et al. |
| 2008/0134434 | A1 | 6/2008 | Celauro |
| 2008/0222811 | A1 | 9/2008 | Gilbert et al. |
| 2009/0070936 | A1 | 3/2009 | Henderson |
| 2009/0139030 | A1 | 6/2009 | Yang |
| 2009/0248041 | A1 | 10/2009 | Williams et al. |
| 2010/0037397 | A1 | 2/2010 | Wood |
| 2010/0192300 | A1 | 8/2010 | Tannoury |
| 2010/0293713 | A1 | 11/2010 | Sharps |
| 2010/0293719 | A1 | 11/2010 | Klemm et al. |
| 2011/0099716 | A1 | 5/2011 | Jackson |
| 2011/0107516 | A1 | 5/2011 | Jackson et al. |
| 2011/0152931 | A1 | 6/2011 | Zhang et al. |
| 2011/0173753 | A1 | 7/2011 | Luginbuhl et al. |
| 2012/0103344 | A1 | 5/2012 | Hunter |
| 2012/0144589 | A1 | 6/2012 | Skripps et al. |
| 2012/0255122 | A1 | 10/2012 | Diel et al. |
| 2013/0111666 | A1 | 5/2013 | Jackson |
| 2013/0191994 | A1 | 8/2013 | Bellows et al. |
| 2013/0283526 | A1 | 10/2013 | Gagliardi |
| 2013/0307298 | A1 | 11/2013 | Meiki |
| 2014/0020183 | A1 | 1/2014 | Dominick |
| 2014/0059773 | A1 | 3/2014 | Carn |
| 2014/0068861 | A1 | 3/2014 | Jackson |
| 2014/0109316 | A1 | 4/2014 | Jackson et al. |
| 2014/0130258 | A1 | 5/2014 | Kobuss |
| 2014/0137327 | A1 | 5/2014 | Tannoury et al. |
| 2015/0038982 | A1 | 2/2015 | Kilroy et al. |
| 2015/0044956 | A1 | 2/2015 | Hacker |
| 2015/0245969 | A1 | 9/2015 | Hight et al. |
| 2015/0245971 | A1 | 9/2015 | Bernardoni et al. |
| 2015/0272681 | A1 | 10/2015 | Skripps et al. |
| 2016/0000621 | A1 | 1/2016 | Jackson |
| 2016/0081582 | A1 | 3/2016 | Rapoport |
| 2016/0089287 | A1 | 3/2016 | Buerstner |
| 2016/0193099 | A1 | 7/2016 | Drake |
| 2016/0317373 | A1 | 11/2016 | Jackson et al. |
| 2016/0331477 | A1 | 11/2016 | Yu et al. |
| 2017/0027797 | A1 | 2/2017 | Dolliver et al. |
| 2017/0049651 | A1 | 2/2017 | Lim |
| 2017/0049653 | A1 | 2/2017 | Lim |
| 2017/0079864 | A1 | 3/2017 | Riley |
| 2017/0112698 | A1 | 4/2017 | Hight et al. |
| 2017/0135891 | A1 | 5/2017 | Kettner |
| 2017/0151115 | A1 | 6/2017 | Jackson |
| 2017/0341232 | A1 | 11/2017 | Perplies |
| 2017/0348171 | A1 | 12/2017 | Jackson |
| 2018/0116891 | A1 | 5/2018 | Beale et al. |
| 2018/0185106 | A1 | 7/2018 | Itkowitz et al. |
| 2018/0185228 | A1 | 7/2018 | Catacchio et al. |
| 2018/0193104 | A1 | 7/2018 | Beale et al. |
| 2018/0207044 | A1 | 7/2018 | Sabet et al. |
| 2018/0222044 | A1 | 8/2018 | Guerrera et al. |
| 2018/0363596 | A1 | 12/2018 | Lim et al. |
| 2019/0000702 | A1 | 1/2019 | Lim et al. |
| 2019/0000707 | A1 | 1/2019 | Lim et al. |
| 2019/0029906 | A1 | 1/2019 | Konsin et al. |
| 2019/0046381 | A1 | 2/2019 | Lim et al. |
| 2019/0046383 | A1 | 2/2019 | Lim et al. |
| 2019/0209409 | A1 | 7/2019 | Jackson et al. |
| 2019/0374420 | A1 | 12/2019 | Lehman et al. |
| 2020/0000668 | A1 | 1/2020 | Lim et al. |
| 2020/0060913 | A1 | 2/2020 | Lim et al. |
| 2020/0060914 | A1 | 2/2020 | Lim et al. |
| 2020/0060915 | A1 | 2/2020 | Lim et al. |
| 2020/0138659 | A1 | 5/2020 | Lim et al. |
| 2020/0138660 | A1 | 5/2020 | Jackson |
| 2020/0155403 | A1 | 5/2020 | Dalbert |
| 2020/0170868 | A1 | 6/2020 | Jackson |
| 2020/0188208 | A1 | 6/2020 | Lim et al. |
| 2020/0268369 | A1 | 8/2020 | Stanton |
| 2020/0281788 | A1 | 9/2020 | Lim et al. |
| 2020/0297568 | A1 | 9/2020 | Lim et al. |
| 2020/0337923 | A1 | 10/2020 | Lim et al. |
| 2020/0337926 | A1 | 10/2020 | Lim et al. |
| 2020/0337927 | A1 | 10/2020 | Lim et al. |
| 2020/0360214 | A1 | 11/2020 | Lim et al. |
| 2021/0106391 | A1 | 4/2021 | Gregerson et al. |
| 2021/0236369 | A1 | 8/2021 | Lee et al. |
| 2021/0290466 | A1 | 9/2021 | Koenig et al. |
| 2021/0330532 | A1 | 10/2021 | Lim et al. |
| 2022/0008016 | A1 | 1/2022 | Harrison et al. |
| 2022/0409311 | A1 | 12/2022 | Tadano et al. |
| 2023/0066826 | A1 | 3/2023 | Morgan |
| 2023/0301862 | A1 | 9/2023 | Lim et al. |
| 2023/0363715 | A1 | 11/2023 | Lim et al. |
| 2023/0363936 | A1 | 11/2023 | Lim et al. |
| 2023/0363969 | A1 | 11/2023 | Lim et al. |
| 2023/0414431 | A1 | 12/2023 | Lim et al. |
| 2024/0065912 | A1 | 2/2024 | Lim et al. |
| 2024/0382362 | A1 | 11/2024 | Lim et al. |

FOREIGN PATENT DOCUMENTS

| | | | | |
|---|---|---|---|---|
| CN | 110025380 | | 7/2019 | |
| CN | 111467179 | | 7/2020 | |
| CN | 211067011 | | 7/2020 | |
| CN | 112451269 | | 9/2021 | |
| CN | 109862845 | B | * 12/2022 | ............ B25J 9/0018 |
| DE | 1158663 | | 12/1963 | |
| DE | 2204573 | | 8/1973 | |
| DE | 29902989 | | 7/1999 | |
| DE | 102005029787 | | 8/2006 | |
| DE | 202018003692 | | 9/2018 | |
| EP | 0255938 | | 2/1988 | |
| EP | 1943996 | | 7/2008 | |
| EP | 3158986 | | 4/2017 | |
| EP | 3434248 | | 1/2019 | |
| EP | 3909539 | | 11/2021 | |
| FR | 1306095 | | 10/1962 | |
| FR | 2635681 | | 3/1990 | |
| GB | 970281 | | 9/1964 | |
| GB | 1547533 | | 6/1979 | |
| GB | 2056378 | | 3/1983 | |
| JP | 2001129039 | | 5/2001 | |

(56) References Cited

FOREIGN PATENT DOCUMENTS

| | | |
|---|---|---|
| JP | 3892275 | 3/2007 |
| JP | 2018069048 | 5/2018 |
| JP | 6449958 | 12/2018 |
| WO | WO0062731 | 10/2000 |
| WO | 2007058673 | 5/2007 |
| WO | 2019067028 | 4/2019 |
| WO | 2020053143 | 3/2020 |
| WO | 2021158769 | 8/2021 |
| WO | 2021176531 | 9/2021 |

OTHER PUBLICATIONS

International Search Report and Written Opinion dated Sep. 10, 2024 in PCT/IB2024/055050.
International Search Report and Written Opinion dated Jul. 19, 2023 in PCT/IB2023/054288.
International Search Report and Written Opinion dated Jun. 27, 2023 in PCT/IL2023/050291.
International Search Report and Written Opinion dated Jul. 20, 2023 in PCT/IB2023/054218.
International Search Report and Written Opinion dated Jul. 20, 2023 in PCT/IB2023/054786.
International Search Report and Written Opinion dated Oct. 11, 2023 in PCT/IB2023/056270.
International Search Report and Written Opinion dated Aug. 8, 2024 in PCT/IB2024/054734.
International Search Report and Written Opinion dated Oct. 18, 2023 in PCT/IB2023/058416.

* cited by examiner

SURGICAL GANTRY AND INTERFACE MOVEABLY INTERCONNECTING SURGICAL TABLE AND GANTRY

CROSS-REFERENCE TO RELATED APPLICATIONS

This application claims the benefit of and priority to U.S. Provisional Patent Application No. 63/469,139 filed May 26, 2023, the entire disclosure of which is incorporated by reference herein.

CROSS-REFERENCE TO RELATED APPLICATION

This application claims the benefit of and priority to U.S. Provisional Patent Application No. 62/926,136 filed Oct. 25, 2019, the entire disclosure of which is incorporated by reference herein.

FIELD

The present technology generally relates to a surgical gantry and an interface for moveably interconnecting a surgical table and the gantry relative to one another, where the gantry supports one or more surgical robotic arms, and the interface can move the surgical table and a patient supported thereon in at least a cranial-caudal direction relative to the gantry and the one or more surgical robotic arms supported thereby.

BACKGROUND

Use of conventional surgical robots and robotic systems during surgery has become common. Such conventional surgical robots and robotic systems are typically separate from conventional surgical tables supporting patients, and the base portions thereof are typically positionable adjacent the heads, the feet, or the lateral sides of the patients and corresponding portions of the surgical tables. Movement of the conventional surgical robots and robotic systems is typically independent of and not coordinated with movement of the conventional surgical tables. To illustrate, the base portions of the conventional surgical robots and robotic systems typically can be positioned and repositioned on the ground relative to the surgical tables and the patients supported thereby, and various arms of the surgical robots and robotic systems typically can be positioned and repositioned to the surgical tables and the patients supported thereby. And the surgical tables typically can be positioned and repositioned on the ground relative to the surgical robot and robotic systems, and the conventional surgical tables typically can be adjusted/articulated to adjust/articulate the positions of the patients supported thereby. However, the conventional surgical robots and robotic systems do not control movement of the conventional surgical tables, and vice versa. As such, coordinated movement between the conventional surgical robots and robotics systems and the conventional surgical tables can be very difficult. Also, given the configuration of the conventional surgical robots and robotics systems, access to various portions of the patients supported by the convention surgical tables can be limited. Typically, access by the conventional surgical robots and robotic systems to the patients is constrained by the location of the base portions thereof relative to the conventional surgical tables. Therefore, there is a need for a surgical gantry and an interface for moveably interconnecting a surgical table and the gantry relative to one another, where the gantry can support one or more surgical robotic arms in locations affording improved access to a patient supported by the surgical table, and the interface can move the surgical table and the patient supported thereon in at least a cranial-caudal direction relative to the gantry and the surgical robotic system supported thereby. Portions of such a surgical gantry can extend above and over the patient supported by the surgical table, and the interface can be incorporated on or relative to the gantry and on the surgical table. The surgical gantry can support the one or more surgical robotic arms above the patient, and portions of the interface can be used to move the surgical table relative to the gantry via actuation thereof. The position of the one or more surgical robotic arms and the movement afforded by the interface can be used to position and reposition the patient relative to the one or more surgical robotic arms to increase an operational area for the one or more surgical robotic arms supported by the surgical gantry.

SUMMARY

The techniques of this disclosure generally relate to a surgical gantry and an interface for moveably interconnecting a surgical table and the gantry relative to one another, where the gantry can support one or more surgical robotic arms, and the interface can be used in positioning and repositioning a patient supported by the surgical table relative to the surgical robotic arms to facilitate use of the surgical robotic arms on the patient.

In one aspect, the present disclosure provides a combination of a surgical table, a gantry including surgical robotic arms, and an interface for moveably interconnecting the surgical table with the gantry, the combination including the surgical table having a first end, an opposite second end, a first lateral side, an opposite second lateral side, a longitudinal cross-member extending between the first end and the second end, at least one track attached to the longitudinal cross-member, and a patient support portion being configured to support a patient thereon; the gantry having a base portion provided on an operating room floor; a support portion supported relative to the base portion, the support portion having a first portion on a first side of the gantry, and a second portion on a second side of the gantry; and a first surgical robotic arm and a second surgical robotic arm of the surgical robotic arms, the first surgical robotic arm supported by the first portion of the gantry and the second surgical robotic arm supported by the second portion of the gantry, the first surgical robotic arm and the second surgical robotic arm each including a first end portion for supporting surgical equipment thereon; and the interface having a collar portion attached relative to the longitudinal cross-member of the surgical table, the collar portion including a first end, an opposite second end, an interior cavity extending between the first end and the second end, an interior surface defining a portion of the interior cavity, and at least one truck attached relative to the interior surface, portions of the longitudinal cross member being received in the interior cavity, and the at least one truck engaged to the at least one track portion attached to the longitudinal cross member; an actuator portion actuatable to facilitate movement of the at least one truck along the at least one track; and a locking portion attached to and/or supported relative to the gantry, and at least one engagement portion moveable between a disengaged position and an engaged position to maintain a position of the collar portion of the surgical table relative to the gantry; where, after the collar portion is maintained in position relative to the gantry by the interface, the actuation of the actuator portion drives movement of portions of cross member into and out of the interior cavity via movement of the at least one truck along the at least one track to correspondingly adjust positions of the surgical table relative to the gantry, and the first surgical robotic arm and the second surgical robotic arm supported by the gantry; where, after the collar portion is maintained in position relative to the gantry, the first surgical robotic arm and the second surgical robotic arm are supported by the gantry above the patient supported by the surgical table, the surgical equipment supported by the first surgical robotic arm and the second surgical robotic arm are moveable within at least a first plane transverse to a cranial-caudal axis of the patient supported by the patient support portion of the surgical table, and as the positions of the surgical table are adjusted relative to the gantry via actuation of the actuator portion, portions of the patient supported by the patient support portion can be moved into and out of the first plane to thereby creating a three-dimensional operational area in which the first surgical robotic arm and the second surgical robotic arm can access the patient and/or areas around the patient.

In another aspect, the present disclosure provides a combination of a surgical table, a gantry including surgical robotic arms, and an interface for moveably interconnecting the surgical table with the gantry, the combination including the surgical table having a first end, an opposite second end, a first lateral side, an opposite second lateral side, a longitudinal cross-member extending between the first end and the second end, and a patient support portion being configured to support a patient thereon; the gantry having a base portion provided on an operating room floor; an extension portion extending outwardly relative to the base portion; a support portion supported relative to the base portion, the support portion having a first portion on a first side of the gantry, and a second portion on a second side of the gantry; a first surgical robotic arm, a second surgical robotic arm, and a third surgical robotic arm of the surgical robotic arms, the first surgical robotic arm supported by the first portion of the gantry, the second surgical robotic arm supported by the second portion of the gantry, and the third surgical robotic arm supported by the extension portion, the first surgical robotic arm, the second surgical robotic arm, and the third surgical robotic arm each including a first end portion for supporting surgical equipment thereon; and the interface having a collar portion attached relative to the longitudinal cross-member of the surgical table, the collar portion including a first end, an opposite second end, and an interior cavity extending between the first end and the second end, portions of the longitudinal cross member being received in the interior cavity, an actuator portion actuatable to facilitate movement of the longitudinal cross-member relative to the collar portion; and a locking portion attached to and/or supported relative to the gantry, and at least one engagement portion moveable between a disengaged position and an engaged position to maintain a position of the collar portion of the surgical table relative to the gantry; where, after the collar portion is maintained in position relative to the gantry by the interface, the actuation of the actuator portion drives movement of portions of cross member into and out of the interior cavity to correspondingly adjust positions of the surgical table relative to the gantry, and relative to the first surgical robotic arm, the second surgical robotic arm, and the third surgical robotic arm supported by the gantry; and where, after the collar portion is maintained in position relative to the gantry, the first surgical robotic arm and the second surgical robotic arm are supported by the gantry above the patient supported by the surgical table, the third surgical arm is supported by the gantry below the patient supported by the surgical table, the surgical equipment supported by the first surgical robotic arm, the second surgical robotic arm, and the third surgical robotic arm are moveable within at least a first plane transverse to a cranial-caudal axis of the patient supported by the patient support portion of the surgical table, and as the positions of the surgical table are adjusted relative to the gantry via actuation of the actuator portion, portions of the patient supported by the patient support portion can be moved into and out of the first plane to thereby creating a three-dimensional operational area in which the first surgical robotic arm, the second surgical robotic arm, and the third surgical robotic arm can access the patient and/or areas around the patient.

In yet another aspect, the present disclosure provides a combination of a surgical table, a gantry including surgical robotic arms, and an interface for moveably interconnecting the surgical table with the gantry, the combination including the surgical table having a first end, an opposite second end, a first lateral side, an opposite second lateral side, a longitudinal cross-member extending between the first end and the second end, and a patient support portion being configured to support a patient thereon; the gantry having a base portion provided on an operating room floor; an extension portion extending outwardly relative to the base portion; a support portion supported relative to the base portion; a first surgical robotic arm and a second surgical robotic arm of the surgical robotic arms, the first surgical robotic arm supported by the support portion of the gantry, and the second surgical robotic arm supported by the extension portion, the first surgical robotic arm and the second surgical robotic arm each including a first end portion for supporting surgical equipment thereon; and the interface having a collar portion attached relative to the longitudinal cross-member of the surgical table, the collar portion including a first end, an opposite second end, and an interior cavity extending between the first end and the second end, portions of the longitudinal cross member being received in the interior cavity; an actuator portion actuatable to facilitate movement of the longitudinal cross-member relative to the collar portion; and a locking portion attached to and/or supported relative to the gantry, and at least one engagement portion moveable between a disengaged position and an engaged position to maintain a position of the collar portion of the surgical table relative to the gantry; where, after the collar portion is maintained in position relative to the gantry by the interface, the actuation of the actuator portion drives movement of portions of cross member into and out of the interior cavity to correspondingly adjust positions of the surgical table relative to the gantry, and relative to the first surgical robotic arm and the second surgical robotic arm supported by the gantry; and where, after the collar portion is maintained in position relative to the gantry, the first surgical robotic arm is supported by the gantry above the patient supported by the surgical table, the second surgical arm is supported by the gantry below the patient supported by the surgical table, the surgical equipment supported by the first surgical robotic arm and the second surgical robotic arm are moveable within at least a first plane transverse to a cranial-caudal axis of the patient supported by the patient support portion of the surgical table, and as the positions of the surgical table are adjusted relative to the gantry via actuation of the actuator portion, portions of the patient supported by the patient support portion can be moved into and out of the first plane thereby creating a three-dimensional operational area in which the first surgical robotic arm and the second surgical robotic arm can access the patient and/or areas around the patient.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The techniques of this disclosure generally relate to a gantry and an interface for moveably interconnecting a surgical table and the gantry that supports one or more surgical arms relative to one another.

DETAILED DESCRIPTION

Figure 1A:
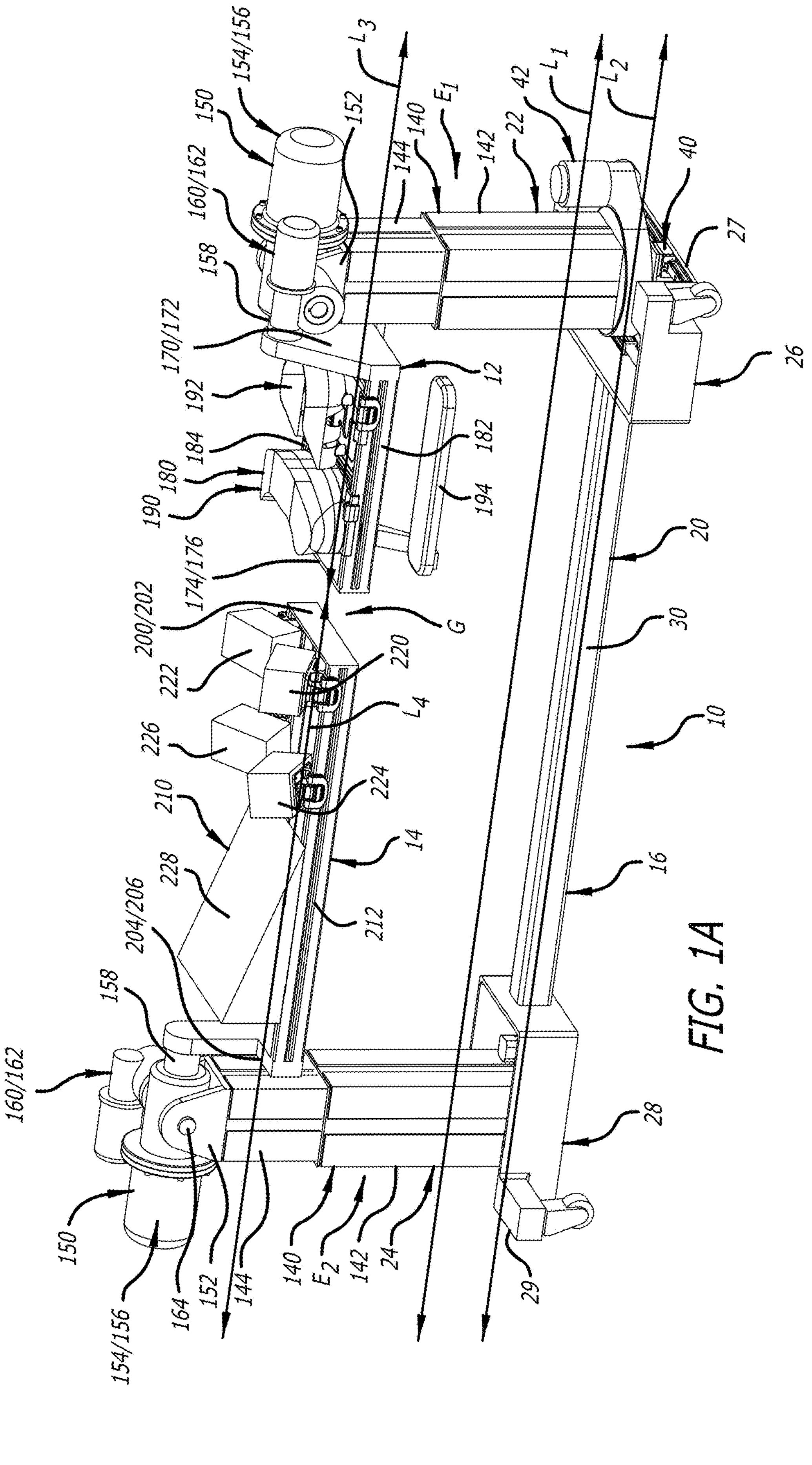
FIG. 1A is a side, perspective view that illustrates a surgical table of the present disclosure.

FIGS. 1-12 depict a prior art embodiment of a surgical table generally indicated by the numeral 10. FIGS. 1-12 were previously described in U.S. Ser. No. 17/741,125, filed May 10, 2022, which is hereby incorporated by reference herein in its entirety. Additionally, FIGS. 13-27 depict a prior art embodiment of an interface generally indicated by the letter I. FIGS. 13-27 were previous described in U.S. Ser. No. 17/846,444, filed Jun. 22, 2022, which is hereby incorporated by reference herein in its entirety.

The surgical table 10 includes a first end E1, a second end E2, and a mid-longitudinal L1 extending through the first end E1 and the second end E2. The surgical table 10 includes a first platform portion 12, a second platform portion, 14 and a support portion 16. The support portion 16 supports the first platform portion 12 and the second 14 above the ground, and the first platform portion 12 and the second platform portion 14 can each support a portion of a patient P thereon.

The first platform portion 12 and the second platform portion 14, as depicted in FIGS. 1A-1C and 6-12, are spaced apart from another across a gap G, and can be independently positioned/oriented and repositioned/reoriented relative to one another. Together, when the patient is supported thereby, adjustment of the first platform portion 12 and the second platform portion 14 relative to one another can be used to manipulate and provide access to the spine of the patient. The manipulation of the patient P and the access afforded by the gap G can aid the performance of surgery on the patient P, and such surgery, for example, can include spinal surgery on the spine of the patient.

The support portion 16, as depicted in FIGS. 1A and 6-12, includes a horizontally-oriented portion 20, a first vertically-oriented portion 22, and a second vertically-oriented portion 24. The horizontally-oriented portion 20 is used in supporting the first vertically-oriented portion 22 and the second vertically-oriented portion 24 relative to the ground, the first vertically-oriented portion 22 is used in supporting the first platform portion 12 relative to the horizontally-oriented portion 20, and the second vertically-oriented portion 24 is used in supporting the second platform portion 14 relative to the horizontally-oriented portion 20. The surgical table 10, as discussed below, can include a controller or controllers for controlling motorized actuators included in the surgical table 10 to facilitate the operation thereof.

As depicted in FIG. 1A, the horizontally-oriented portion 20 includes a first end portion 26 at a first end 27 thereof (collocated with the first end E1), a second end portion 28 at a second end 29 thereof (collocated with the second end E2), and a cross member 30 extending between the first end portion 26 and the second end portion 26. The cross member 30 can be aligned with a mid-longitudinal axis L2 of the horizontally-oriented portion 20, can be used to connect the first end portion 26 and the second end portion 28, and can be expandable and contractable to expand and contract a length of the horizontally-oriented portion 20 along the mid-longitudinal axis L2.

Figure 2:
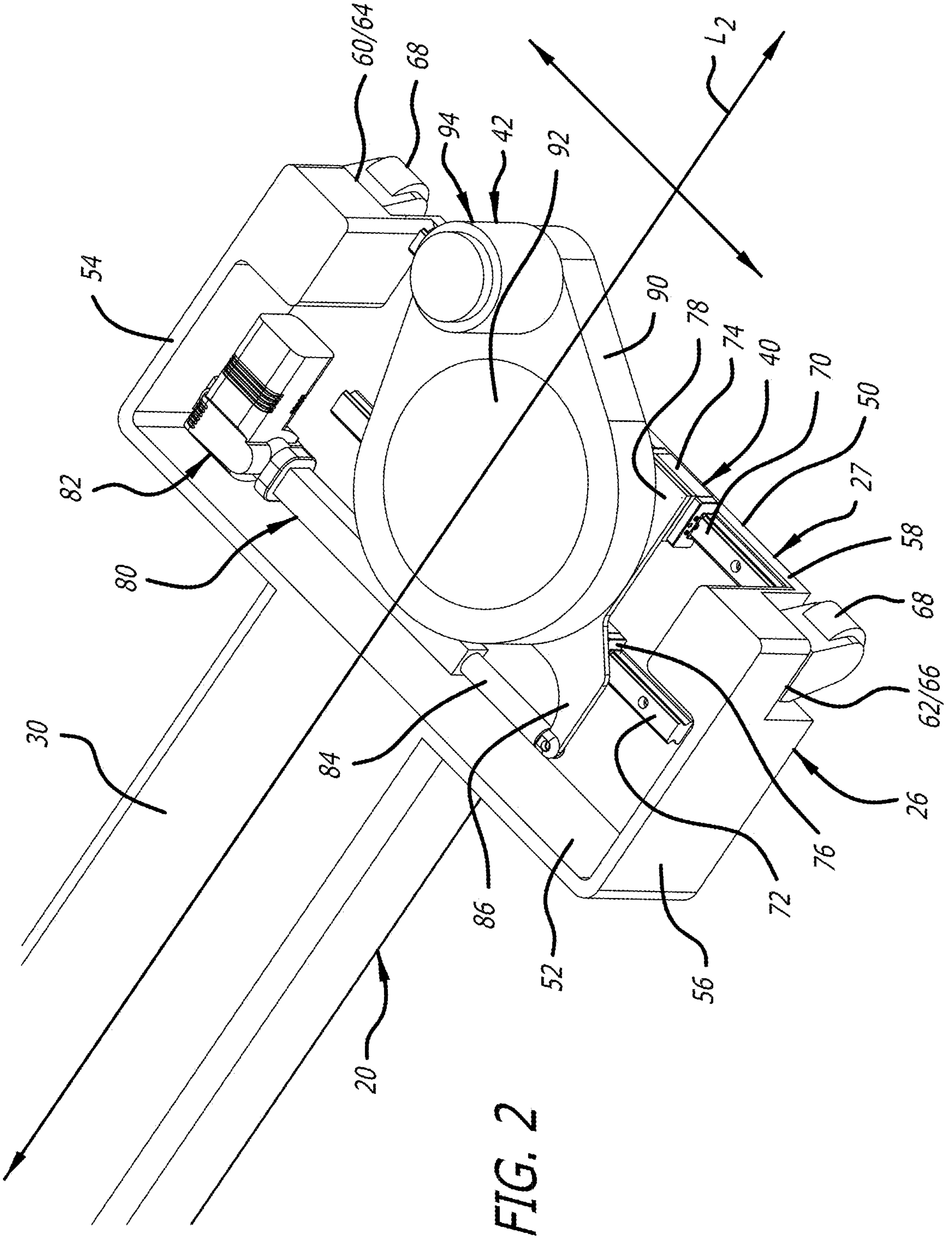
FIG. 2 is a top, perspective view that illustrates a slider portion and a rotatable portion of a first end portion of the surgical table of FIG. 1A.
Figure 3:
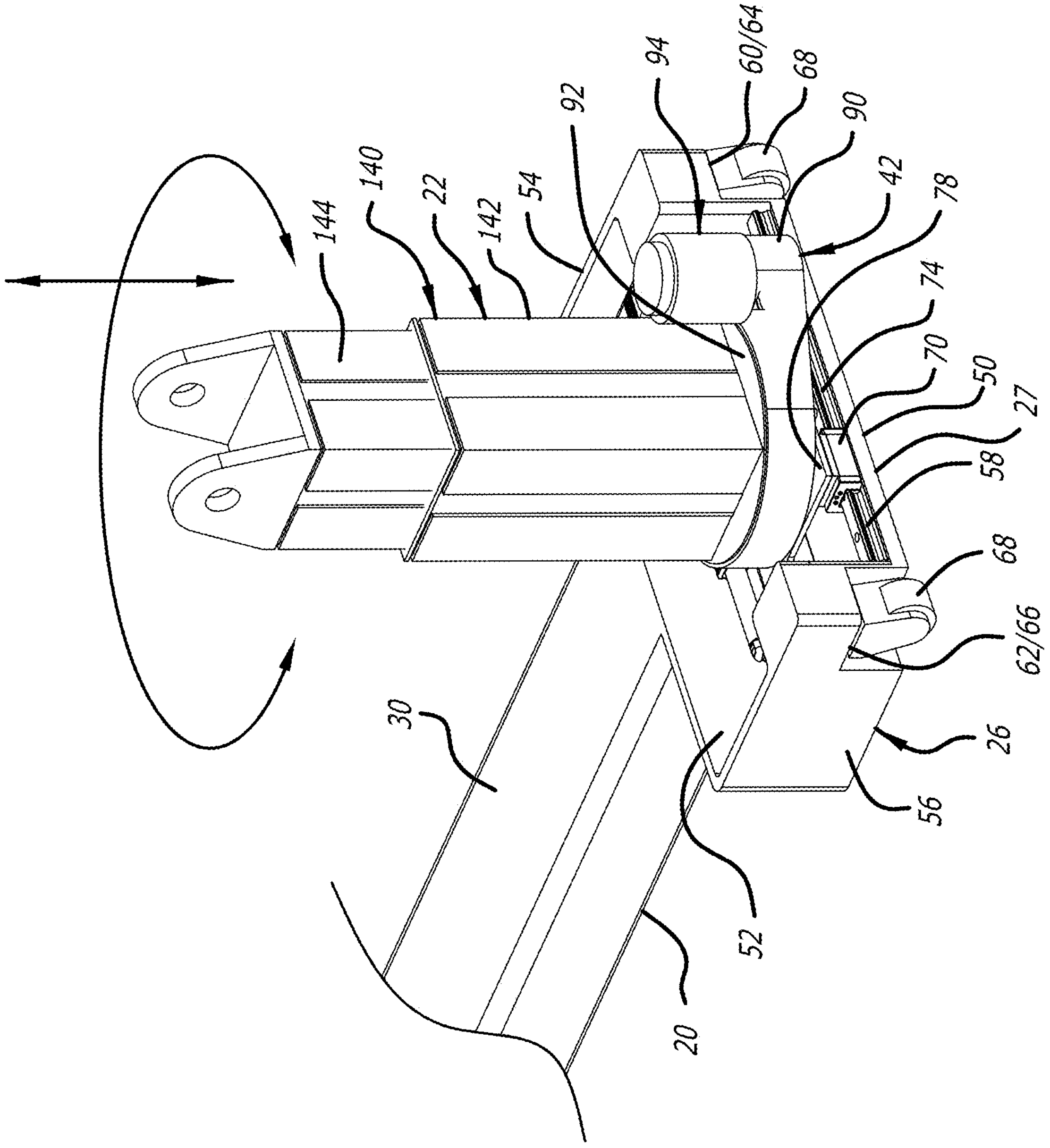
FIG. 3 is an end, perspective view that illustrates the slider portion and the rotatable portion of the first end portion supporting a first vertically-oriented portion of the surgical table of FIG. 1A.

The first end portion 26, as depicted in FIGS. 2 and 3, supports the first vertically-oriented portion 22, and includes a slider portion 40 and a rotator portion 42. As discussed below, the slider portion 40 is configured to move the first vertically-oriented portion 22 in directions transverse to the mid-longitudinal axes L1 and L2, and the rotator portion 42 is configured to rotate the first vertically-oriented portion 22 about a vertically-oriented axis. As depicted in FIGS. 2 and 3, the first end portion 26 includes a bottom portion 50, an endwall portion 52, a first sidewall portion 54, and a second sidewall portion 56.

The first end portion 26 includes an open end 58 adjacent the first end 27, and together, the bottom portion 50, the endwall portion 52, the first sidewall portion 54, and the second sidewall portion 56 define an area in which the slider portion 40 and the rotator portion 42 are provided. Furthermore, the first sidewall portion 54 and the second sidewall portion 56 include indentations 60 and 62 that include undersurfaces 64 and 66, respectively. Casters 68 can be attached to each of the undersurfaces 64 and 66, and together with other casters, the casters 68 can be used to space the support portion 16 from the ground and to facilitate movement of the support portion 16.

The slider portion 40, as depicted in FIGS. 2 and 3, includes a first track portion 70, a second track portion 72, first trucks 74 moveable along the first track portion 70, second trucks 76 moveable along the second track portion 72, and a platform portion 78 supported by the first trucks 74 and the second trucks 76. Using movement of the first trucks 74 and the second trucks 76 on the first track portion 70 and the second track portion 72, respectively, the platform portion 78 is moveable relative to the bottom portion 50 in side-to-side directions transverse to the mid-longitudinal axes L1 and L2 between a first position and a second position. In the first position, a majority of the platform portion 78 is located on one side of the mid-longitudinal axis L2, and, in the second position, a majority of the platform portion 78 is located on the other side of the mid-longitudinal axis L2.

Linear movement of the platform portion 78 can be controlled via operation of an actuator 80 that includes a motor and transmission portion 82 that is actuatable to move a telescoping arm portion 84 inwardly and outwardly. The telescoping arm portion 84 is attached to an extension portion 86 that extends outwardly from the platform portion 78. As such, the inward movement and the outward movement of the telescoping arm portion 84 serves to move the platform portion 78 (and the first vertically-oriented portion 22 supported thereby) between the first position and the second position thereof. As such, the first platform portion 12 supported by the first vertically-oriented portion 22 can be moved in side-to-side directions relative to the mid-longitudinal axes L1 and L2 via actuation of the actuator 80 of the slider portion 40. Furthermore, the operation of the slider portion 40 and the actuator 80 thereof can be controlled by the controllers of the surgical table 10.

As depicted in FIG. 3, the platform portion 78 can support the rotator portion 42 thereon, and the rotator portion 42 can support the first vertically-oriented portion 22 thereon. The rotator portion 42 can include a base portion 90, a rotatable portion 92, and an actuator 94. Rotation of the rotatable portion 92 can be controlled via operation of the actuator 94 that includes a motor and transmission portion 94 that is actuatable to rotate the rotatable portion 92 and the first vertically-oriented portion 22 supported by the rotatable portion 92 about a vertically-oriented axis. As such, the first platform portion 12 can be rotated relative to the platform portion 78, the first end portion 26, and the support portion 16 via actuation of the actuator 94 of the rotator portion 42. Furthermore, the operation of the rotator portion 42 and the actuator 94 thereof can be controlled by the controllers of the surgical table 10.

Figure 4:
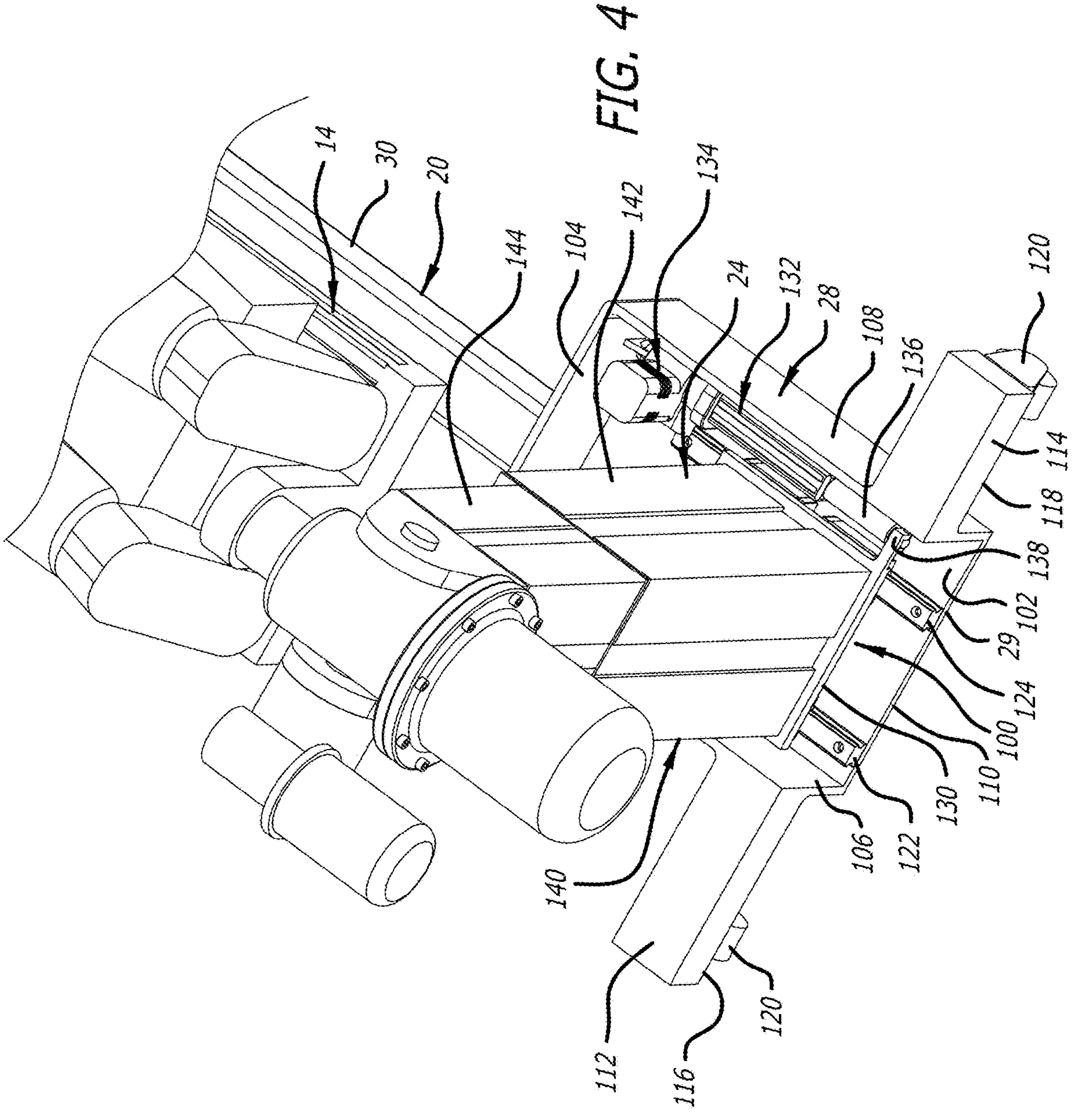
FIG. 4 is a top, perspective view that illustrates a slider portion of a second end portion supporting a second vertically-oriented portion of the surgical table of FIG. 1A.
Figure 5:
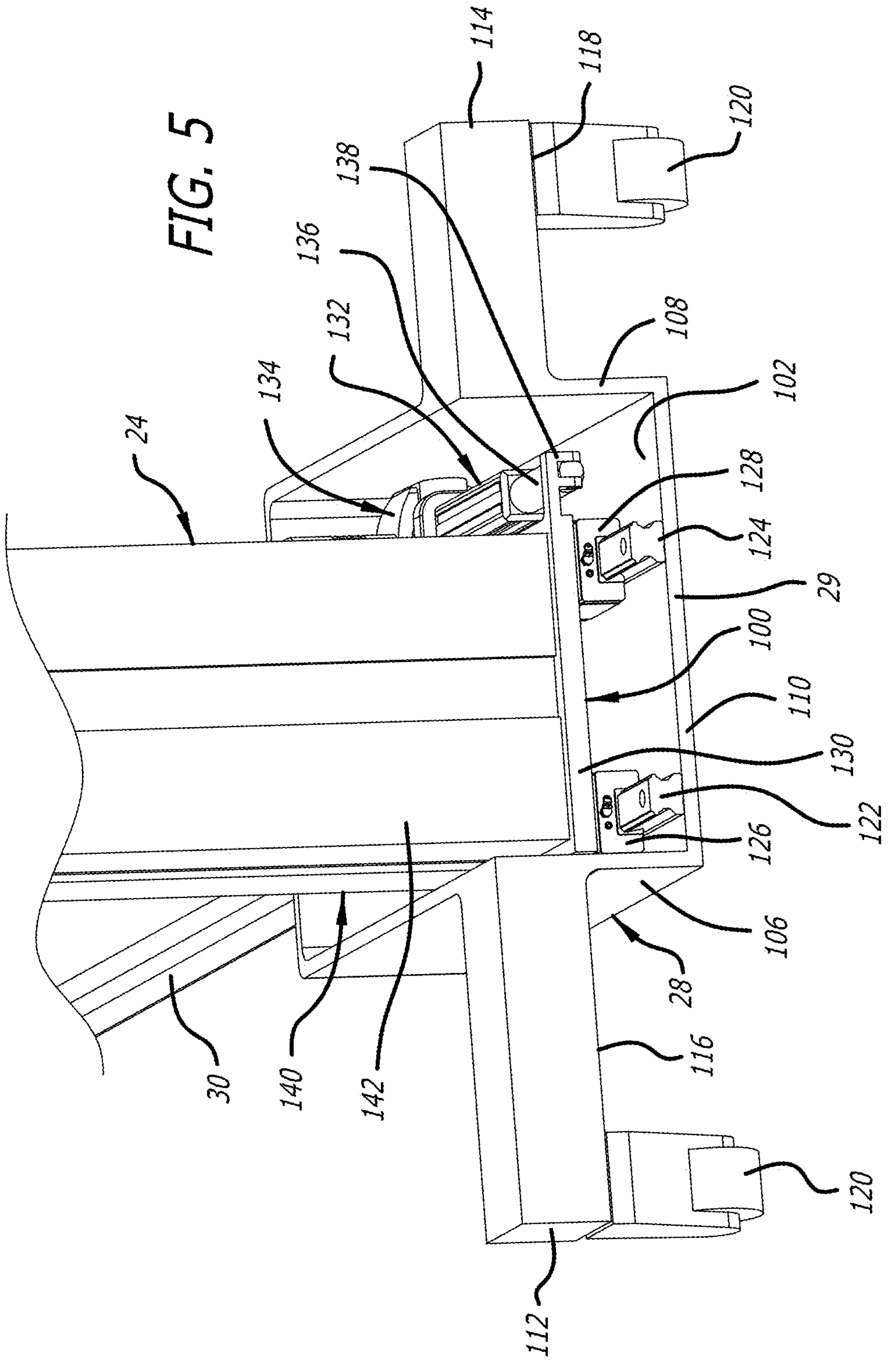
FIG. 5 is an end, perspective view that illustrates the slider portion of the second end portion supporting the second vertically-oriented portion of the surgical table of FIG. 1A.

The second end portion 28, as depicted in FIGS. 4 and 5, supports the second vertically-oriented portion 24, and includes a slider portion 100. As discussed below, the slider portion 100 is configured to move the second vertically-oriented portion 24 toward and away from the first vertically-oriented portion 22 in directions aligned with the longitudinal axes L1 and L2. As depicted in FIGS. 4 and 5, the second end portion 28 includes a bottom portion 102, an endwall portion 104, a first sidewall portion 106, and a second sidewall portion 108.

The second end portion 28 includes an open end 110 adjacent the second end 29, and together, the bottom portion 102, the endwall 104, the first sidewall portion 106, and the second sidewall portion 108 define an area in which the slider portion 100 are provided. An arm portion 112 extends outwardly from the first sidewall portion 106 and an arm portion 114 extends outwardly from the second sidewall portion 108, and the arm portions 112 and 114 include undersurfaces 116 and 118, respectively. Casters 120 can be attached to each of the undersurfaces 116 and 118, and together with the casters 68, the casters 120 can be used to space the support portion 16 from the ground and to facilitate movement of the support portion 16.

The slider portion 100, as depicted in FIGS. 4 and 5, includes a first track portion 122, a second track portion 124, first trucks 126 moveable along the first track portion 122, second trucks 128 moveable along the second track portion 124, and a platform portion 130 supported by the first trucks 126 and the second trucks 128. Using movement of the first trucks 126 and the second trucks 128 on the first track portion 122 and the second track portion 124, respectively, the platform portion 130 is moveable relative to the bottom portion 102 in directions aligned with the longitudinal axes L1 and L2 between a first position and a second position. In the first position, the platform portion 130 is located adjacent the second end 29, and, in the second position, the platform portion 130 is located adjacent the endwall portion 104.

Linear movement of the platform portion 130 can be controlled via operation of an actuator 132 that includes a motor and transmission portion 134 that is actuatable to move a telescoping arm portion 136 inwardly and outwardly. The telescoping arm portion 136 is attached to an extension portion 138 that extends outwardly from the platform portion 130. As such, the inward movement and the outward movement of the telescoping arm portion 138 serves to move the platform portion 130 (and the second vertically-oriented portion 24 supported thereby) between the first position and the second position thereof. As such, the second platform portion 14 supported by the second vertically-oriented portion 24 can be moved toward and away from the first platform portion 12 in directions aligned with the mid-longitudinal axes L1 and L2 via actuation of the actuator 132 of the slider portion 100. Furthermore, the operation of the slider portion 100 and the actuator 132 thereof can be controlled by the controllers of the surgical table 10.

As discussed below, the use of the slider portion 40 and the rotator portion 42 of the first end portion 26, and the use of the slider portion 100 of the second end portion 28 can afford independent movement and adjustment of the first platform portion 12 and the second platform portion 14 relative to one another. Furthermore, rather than employing the slider portion 40 and the rotator portion 42, the first vertically-oriented portion 22 can be supported directly by the first end portion 26 and be fixed in position relative thereto, and rather than employing the slider portion 100, the second vertically-oriented portion 24 can be supported directly by the second end portion 28. As such, if the slider portion 40, the rotatable portion 42, and the slider portion 100 are not provided, portions of the first vertically-oriented portion 22 and the second vertically-oriented portion 24 can be used to facilitate independent movement and adjustment of the first platform portion 12 and the second platform portion 14 relative to one another.

As depicted in FIGS. 1A, 1B, and 6-12, each of the first vertically-oriented portion 22 and the second vertically oriented 24 can include a telescoping column 140 for positioning/orienting and repositioning/reorienting the first platform portion 12 and the second platform portion 14 relative to the horizontally-oriented portion 20. Each of the telescoping columns 140 can include a lower portion 142 and an upper portion 144. The upper portions 144 can be telescopically moved upwardly and downwardly relative to the lower portions 142 between a lower position and an upper position. The lower portions 142 of the telescoping columns 140 are supported by the first end portion 26 and the second end portion 28. As such, the telescopic expansion and contraction of the telescoping columns 140 can be used to correspondingly raise and lower the first platform portion 12 and the second platform portion 14 relative to the horizontally-oriented portion 20.

Figure 1B:
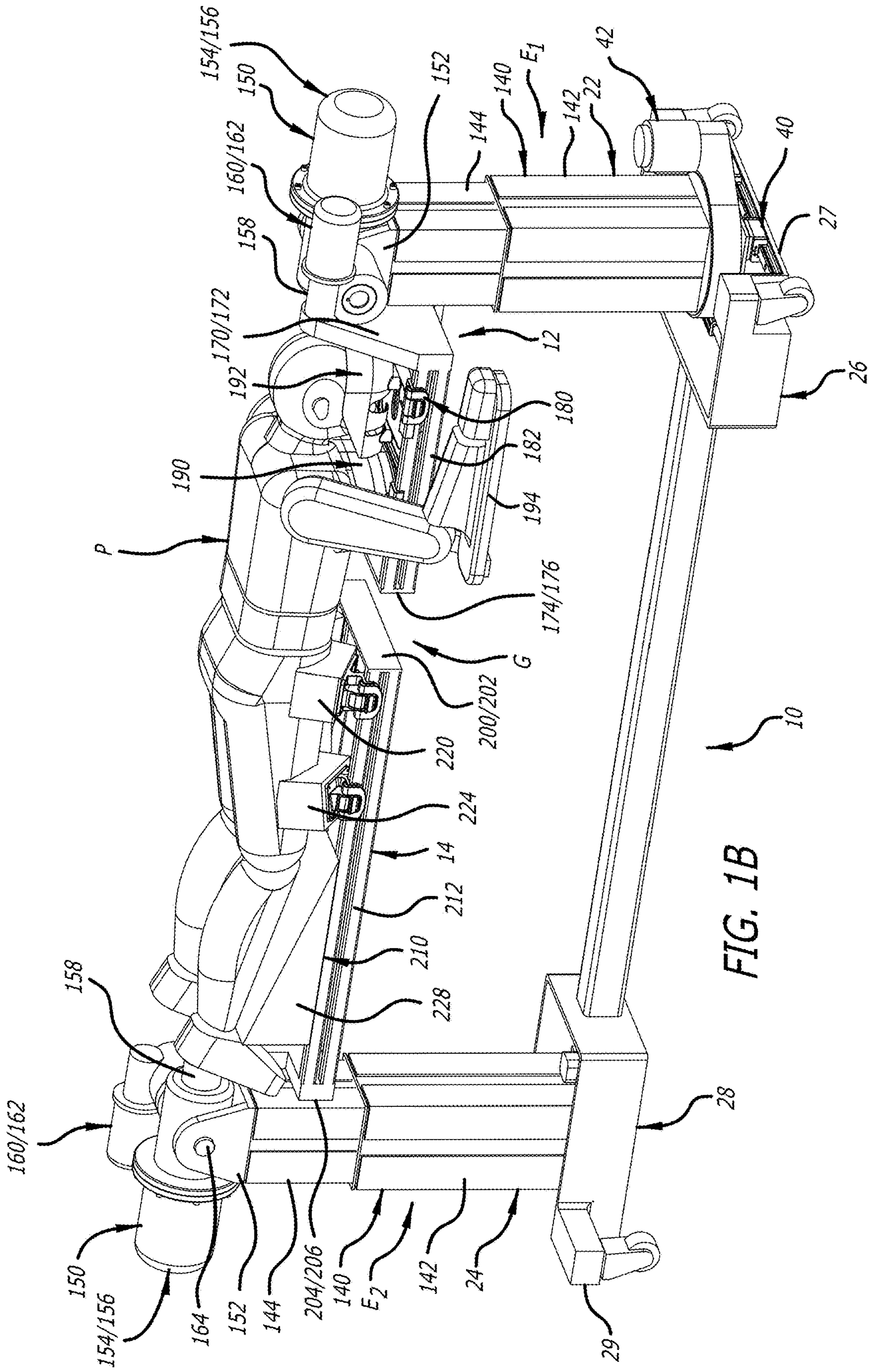
FIG. 1B is a side, perspective view similar to FIG. 1A that illustrates the surgical table of FIG. 1A with a patient positioned thereon in a prone position.
Figure 1C:
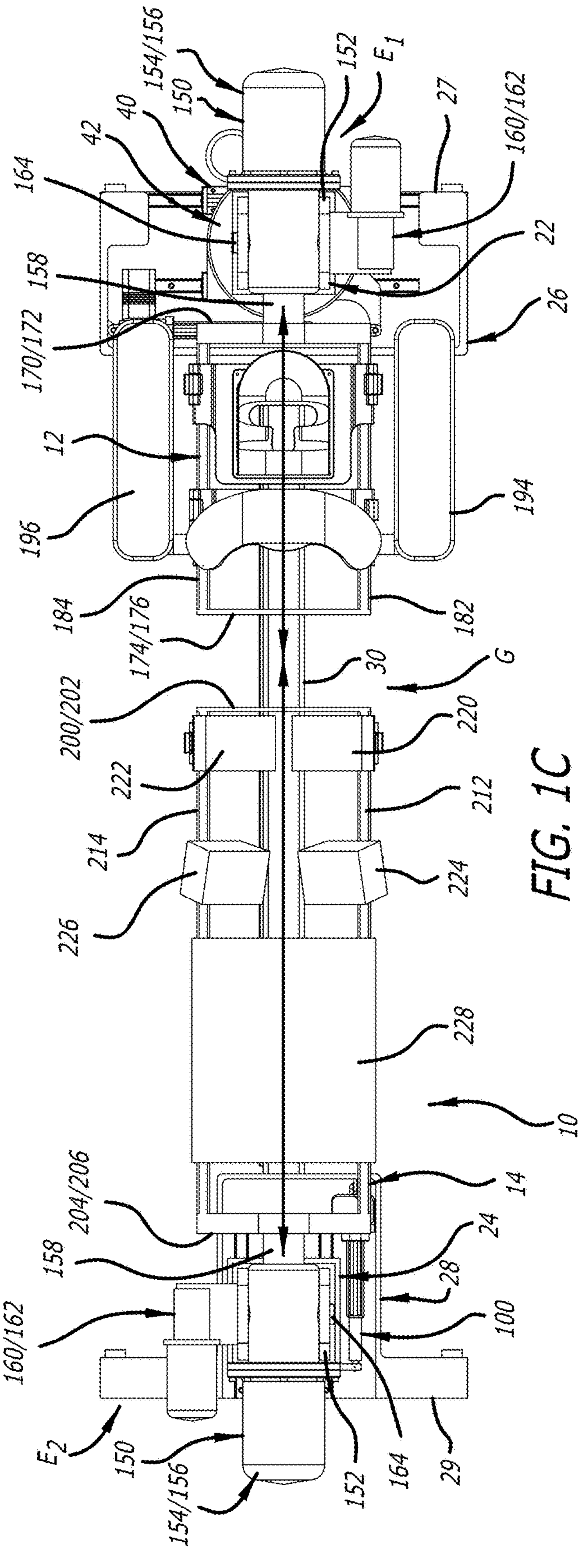
FIG. 1C is a top, plan view that illustrates the surgical table of FIG. 1A with the patient positioned thereon.

As depicted in FIGS. 1A, 1B, and 6-12, each of the first vertically-oriented portion 22 and the second vertically-oriented portion 24 also include a rotational/tilt positioner 150. Each of the rotational/tilt positioners 150 can be supported relative to the telescoping column 140 by a clevis 152 attached to the upper portion 144. The rotational/tilt positioners 150 each include a rotational portion 154 including a motor and transmission 156 and an axle 158, and a tilt portion 160 including a motor and transmission 162 and an axle 164. As depicted in FIGS. 1A-1C, portions of the motors and transmissions 156 of the rotational portions 154 can be positioned between portions of the clevis 152, and the axles 158 can extend outwardly from the motors and transmissions 156 and be attached to the first platform portion 12 and the second platform portion 14. Furthermore, the motors and transmissions 162 of the tilt portions 160 can be positioned on one side of portions of the clevises 152, and the axles 164 can be received through the clevises 152 and be attached to portions of the rotational portions 154. Operation of the motors and transmissions 156 serve in rotating the axle 158 to rotate the first platform portion 12 and the second platform portion 14 attached thereto, and operation of the motors and transmissions 162 serves in rotating the axles 164 to tilt the rotational portions 154 and the first platform portion 12 and the second platform portion 14 attached thereto.

Accordingly, to further position/orient and reposition/reorient the first platform portion 12 and the second platform portion 14, the platform portion 12 and the second platform portion 14 each can be raised and lowered via expansion and contraction of the telescoping columns 140, the first platform portion 12 and the second platform portion 14 each can be rotated side to side by rotation of the axles 158 using the motors and transmissions 156, and the first platform portion 12 and the second platform portion 14 can be tilted upwardly or downwardly by rotation of the axles 164 using the motors and transmissions 162. The rotation of the axles 158 can rotate the first platform portion 12 and the second platform portion 14 side to side in a vertical plane perpendicular to the mid-longitudinal axes L1 and L2, and the rotation of the axles 164 can tilt the first platform portion 12 and the second platform portion 14 upwardly and downwardly in a vertical plane aligned with the mid-longitudinal axes L1 and L2 As discussed below, the operation of the telescoping columns 140, the motors and transmissions 156, and the motors and transmissions 162 can be controlled by the controllers of the surgical table 10.

As depicted in FIGS. 1A-1C, the first platform portion 12 includes a first end portion 170 at and adjacent a first end 172 thereof, a second end portion 174 at and adjacent a second end 176 thereof, and various rails positioned therebetween that connect the first end portion 170 and the second end portion 174 to one another. A portion of first end portion 170 has a height sufficient enough to afford attachment relative to the axle 158 of the rotational/tilt positioner 150 of the first vertically-oriented portion 22, and such attachment affords movement thereof via operation of the rotational/tilt positioner 150.

The first platform portion 12 includes a first patient support portion 180, and the various rails, as depicted in FIGS. 1A and 1C, can include a first outer rail 182 and a second outer rail 184 that extend between the first end portion 170 and the second end portion 174. First end portions of the first outer rail 182 and the second outer rail 184 can be attached to the first end portion 170, opposite second end portions of the first outer rail 182 and the second outer rail 184 can be attached to the second end portion 174, and/or the first and second end portions can be attached to intermediate portions (not shown) positioned between the various rails and the first end portion 170 and/or the second end portion 174. Furthermore, the first outer rail 182 and the second outer rail 184 can be aligned with a mid-longitudinal axis L3 of the first platform portion 12, with the first outer rail 182 being positioned on one side of the mid-longitudinal axis L3, and the second outer rail 184 being positioned on the other side of the mid-longitudinal axis L3.

In addition to providing structural rigidity to the first platform portion 12, the first outer rail 182 and the second outer rail 184 can also be used to support the first patient support portion 180 of the first platform portion 12. The patient support portion 180 can include a chest support portion 190 and a head support portion 192 that are integrated with or separate from one another. As depicted in FIG. 1C, the chest support portion 190 and the head support portion 192 are separate from one another. Furthermore, the chest support portion 190 and/or the head support portion 192 can be moveably adjusted or fixed in position along portions of the first outer rail 182 and the second outer rail 184 to accommodate differently-sized patients. As such, the first outer rail 182 and the second outer rail 184 serves as tracks affording movement of the chest support portion 190 and the head support portion 192. As depicted in FIGS. 1B and 6-12, the patient P is supported in a prone position by the first patient support portion 180, with the upper torso of the patient being supported by the chest support portion 190, and the head of the patient being supported by the head support portion 192. The chest support portion 190 and the head support portion 192 can be configured and operate in similar fashion to those disclosed in U.S. Ser. Nos. 17/740,559 and 17/740,588, both filed May 10, 2022, which are hereby incorporated by reference herein.

In addition to the chest support portion 190 and the head support portion 192, first and second arm supports 194 and 196 can be provided as part of the first platform portion 12 to support arms of the patient relative to the remaining portions thereof. As depicted in FIG. 1C, the first arm support 194 is attached relative to the first outer rail portion 182, and the second arm support 196 is attached relative to the second outer rail portion 184. As such, when the patient P is in the prone position with the upper torso of the patient supported by the chest support portion 190 and the head of the patient supported by the head support portion 192, the right arm and the left arm of the patient can be supported relative to the remainder of the first platform portion 12 by the first arm support 194 and the second arm support 196, respectively.

As depicted in FIGS. 1A-1C, the second platform portion 14 includes a first end portion 200 at and adjacent a first end 202 thereof, a second end portion 204 at and adjacent a second end 206 thereof, and various rails positioned therebetween that connect the first end portion 200 and the second end portion 204 to one another. A portion of second end portion 204 has a height sufficient enough to afford attachment relative to the axle 158 of the rotational/tilt positioner 150 of the second vertically-oriented portion 24, and such attachment affords movement thereof via operation of the rotational/tilt positioner 150.

The second platform portion 14 includes a second patient support portion 210, and the various rails, as depicted in FIGS. 1A and 1C, can include a first outer rail 212 and a second outer rail 214 that extend between the first end portion 200 and the second end portion 204. First end portions of the first outer rail 212 and the second outer rail 214 can be attached to the first end portion 200, opposite second end portions of the first outer rail 212 and the second outer rail 214 can be attached to the second end portion 204, and/or the first and second end portions can be attached to intermediate portions (not shown) positioned between the various rails and the first end portion 200 and/or the second end portion 204. Furthermore, the first outer rail 212 and the second outer rail 214 can be aligned with a mid-longitudinal axis L4 of the second platform portion 14, with the first outer rail 212 being positioned on one side of the mid-longitudinal axis L4, and the second outer rail 214 being positioned on the other side of the mid-longitudinal axis L4.

In addition to providing structural rigidity to the second platform portion 14, the first outer rail 212 and the second outer rail 214 can also be used to support the second patient support portion 210 that can include a first upper thigh support 220, a second upper thigh support 222, a first lower thigh support 224, and a second lower thigh support 226. The first upper thigh support 220, the second upper thigh support 222, the first lower thigh support 224, and the second lower thigh support 226 can be moveably adjusted or fixed in position along portions of the first outer rail 212 and the second outer rail 214 to accommodate differently-sized patients. As depicted in FIGS. 1A and 1C, the first upper thigh support 220 and the first lower thigh support 224 are supported by the first outer rail 212, and the second upper thigh support 222 and the second lower thigh support 226 are supported by the second outer rail 214. As such, the first outer rail 212 and the second outer rail 214 serve as tracks affording movement of the first upper thigh support 220, the second upper thigh support 222, the first lower thigh support 224, and the second upper lower support 226. In addition to the first upper thigh support 220, the second upper thigh support 222, the first lower thigh support 224, and/or the second lower thigh support 226, a lower leg support 228 of the second patient support portion 210 can be provided. As depicted in FIGS. 1B and 6-12, the patient P is supported in a prone position by the first upper thigh support 220, the second upper thigh support 222, the first lower thigh support 224, the second lower thigh support 226, and the lower leg support 228. The first upper thigh support 220, the second upper thigh support 222, the first lower thigh support 224, the second upper thigh support 226, and the lower leg support 228 can be configured and operate similar fashion to those disclosed in U.S. Ser. Nos. 17/740,559 and 17/740,588, both filed May 10, 2022, which are incorporated by reference herein.

As depicted in FIGS. 1B and 6-12, adjustment of the relative positions of the first platform portion 12 and the second platform portion 14 affords positioning/orienting and repositioning/reorienting of the patient P supported thereby before, during, and after surgery. To illustrate, the first platform portion 12 and the second platform portion 14 can be independently adjusted relative to another to position/orient and reposition/reorient portions of the patient supported thereby. The independent adjustment of the relative positions of the first platform portion 12 and the second platform portion 14 is afforded by the separation therebetween defined by the gap G, and such adjustment can correspondingly be used to change the position/orientation of a first portion of the patient P supported by the first platform portion 12 and a second portion of the patient P supported by the second platform portion 14 relative to one another.

As depicted in FIGS. 1B and 6-12, for example, the head and upper torso of the patient P are supported by the first platform portion 12 and the upper and lower legs of the patient P are supported by the second platform portion 14. And, while the head and upper torso of the patient P are supported by the first patient support portion 180 on the first platform portion 12, and the upper and lower legs of the patient P are supported by the second patient support portion 210 on the second platform portion 14, the position of the patient P could be reversed with the first patient support portion 180 supporting the head and upper torso of the patient P on the second platform portion 14, and the second patient support portion 210 supporting the upper and lower legs of the patient P on the first platform portion 12. Furthermore, while the patient is supported in the prone position in FIGS. 1B and 6-12 the patient P could be supported in the supine position on the first platform portion 12 and the second platform portion 12.

The first platform portion 12 can be raised and lowered via operation of the corresponding telescoping column 140, can be rotated with rotation of the corresponding axle 158 via actuation of the corresponding motor and transmission 156 of the corresponding rotational portion 154, can be titled with rotation of the corresponding axle 164 via actuation of the corresponding motor and transmission 162 of the corresponding tilt portion 160, can be moved in side-to-side directions relative to the mid-longitudinal axes L1 and L2 via actuation of the actuator 80 of the slider portion 40, and can be rotated about a vertically-oriented axis relative to the support portion 16 via actuation of the actuator 94 of the rotator portion 42. Furthermore, the second platform portion 14 can be raised and lowered via operation of the corresponding telescoping column 140, can be rotated with rotation of the corresponding axle 158 via actuation of the corresponding motor and transmission 156 of the corresponding rotational portion 154, can be titled with rotation of the corresponding axle 164 via actuation of the corresponding motor and transmission 162 of the corresponding tilt portion 160, and can be moved toward and away from the first platform portion 12 in directions aligned with the mid-longitudinal axes L1 and L2 via actuation of the actuator 132 of the slider portion 100. In addition to such movement, the chest support portion 130, the head support portion 132, the first the first upper thigh support 220, the second upper thigh support 222, the first lower thigh support 224, the second lower thigh support 226, and the lower leg support 228 can be adjusted to accommodate differently-sized patients.

In manipulating the patient P, the telescoping column 140 of the first vertically-oriented portion 22 could be actuated to raise the position of the first platform portion 12 and the tilt portion 160 of the first vertically-oriented portion 22 could be actuated to tilt the position/orientation of the first platform portion 12, and in doing so, bend the patient's body from a neutral position/orientation (FIG. 6) to tilt the head and upper torso upwardly. Similarly, the telescoping platform 140 of the second vertically-oriented portion 22 could be actuated to raise the position of the second platform portion 14 and the tilt portion 160 of the second vertically-oriented portion could be actuated to tilt the position/orientation of the second platform portion 14, and in doing so, bend the patient's body to tilt the legs upwardly. Furthermore, as depicted in FIG. 7, the first support platform 12 and the second support platform 14 could be positioned/oriented to both tilt the head and upper torso of the patient P upwardly and tilt the legs of the patient P upwardly. Accordingly, the positions/orientations of the first support platform 12 and the second support platform 14 via actuation of the telescoping columns 140 and the tilt portions 160 of the first vertically-oriented portion 22 and the second vertically-oriented portion 24 can be adjusted from a neutral position/orientation as depicted in FIG. 6, to bend the patient's body to move the head and upper torso upwardly and/or move the legs upwardly to introduce degrees of extension to the patient's spine.

Figure 6:
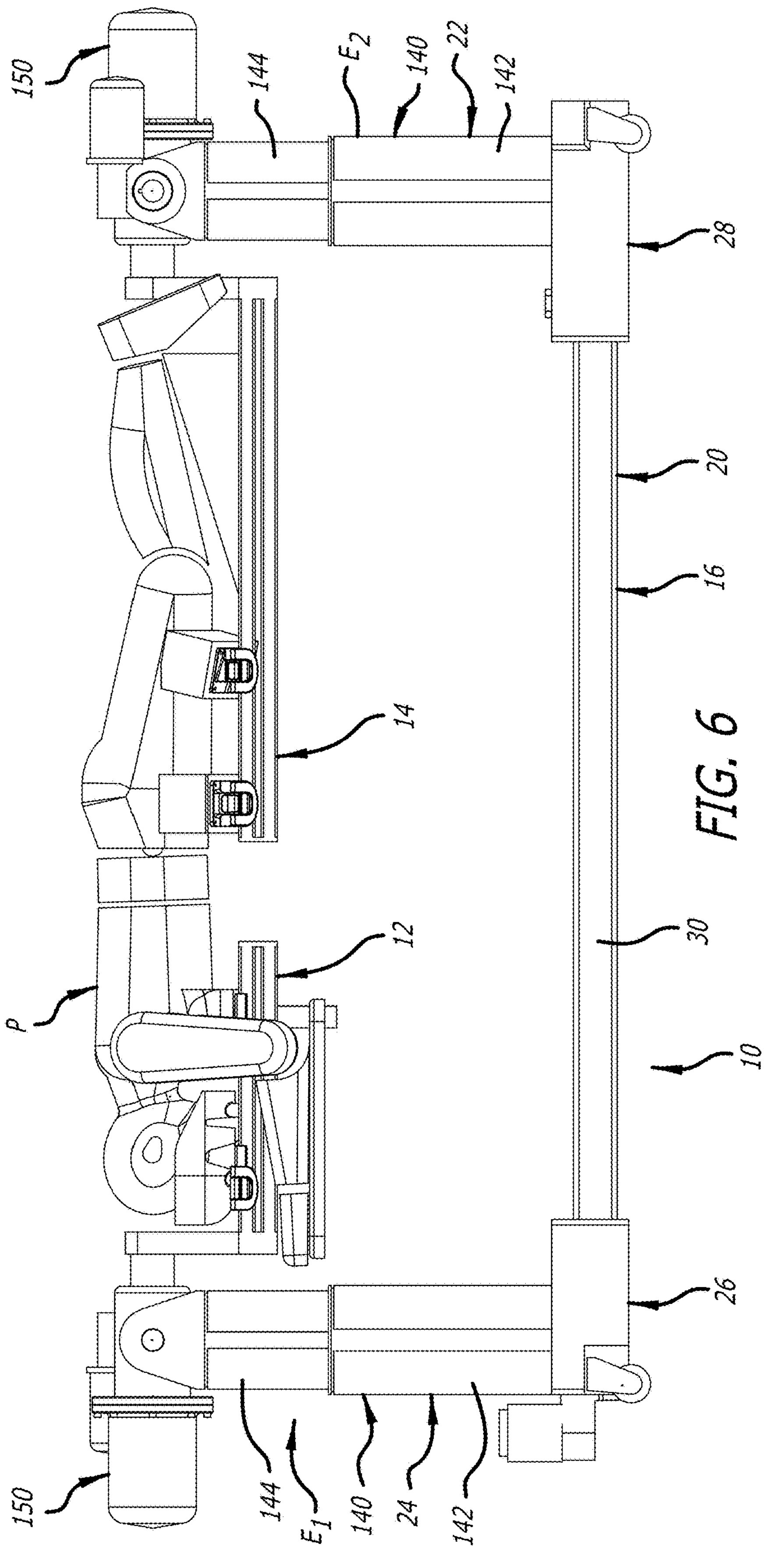
FIG. 6 is a side, elevational view that illustrates the patient positioned on the surgical table of FIG. 1A in the prone position with a first portion of the patient supported by a first platform portion and a second portion of the patient supported by a second platform portion in a neutral position.
Figure 7:
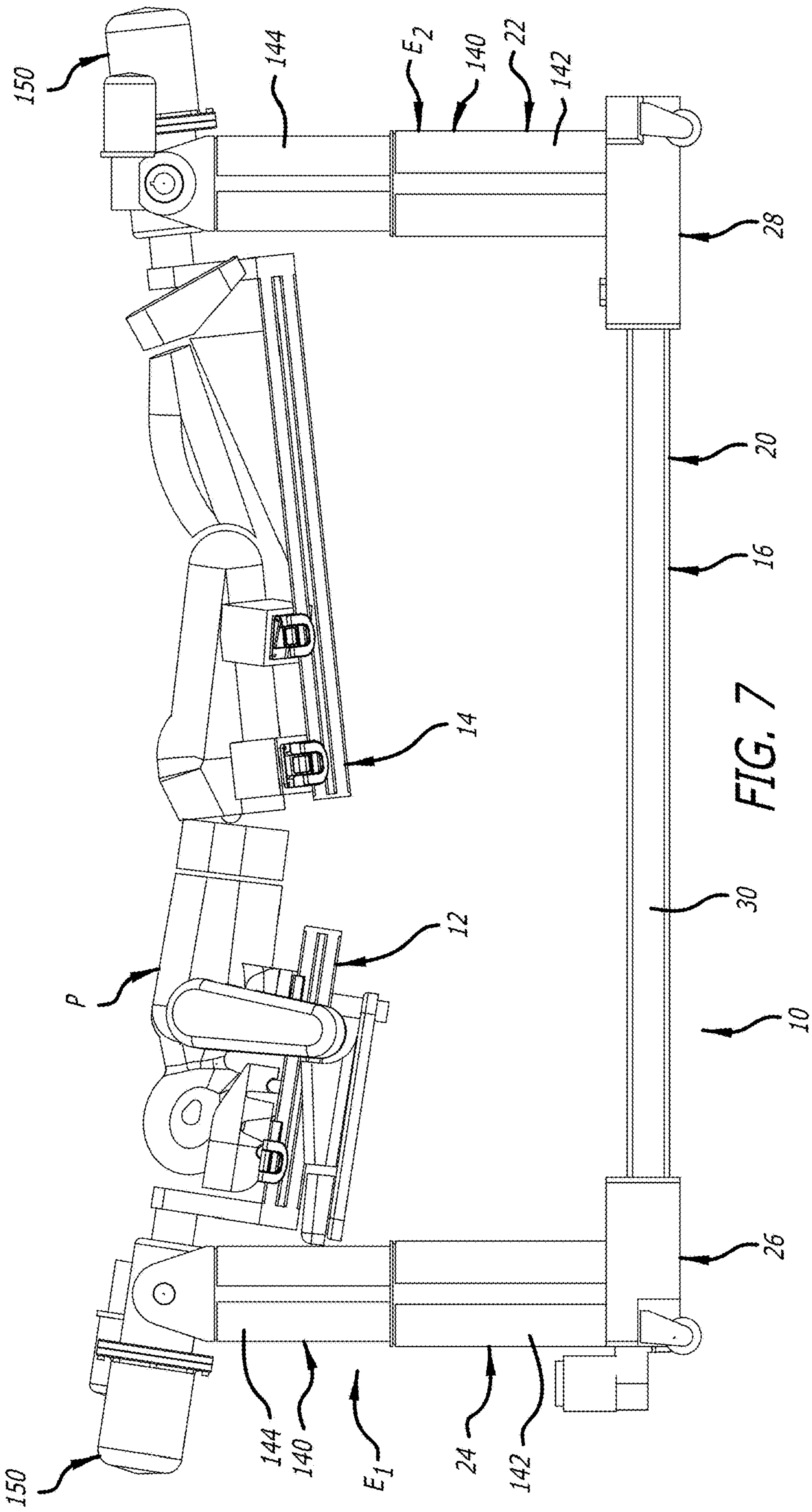
FIG. 7 is a side, elevational view that illustrates the first and second portions of the surgical table of FIG. 1A and the corresponding first and second portions of the patient supported thereon raised and tilted downwardly relative to another.
Figure 8:
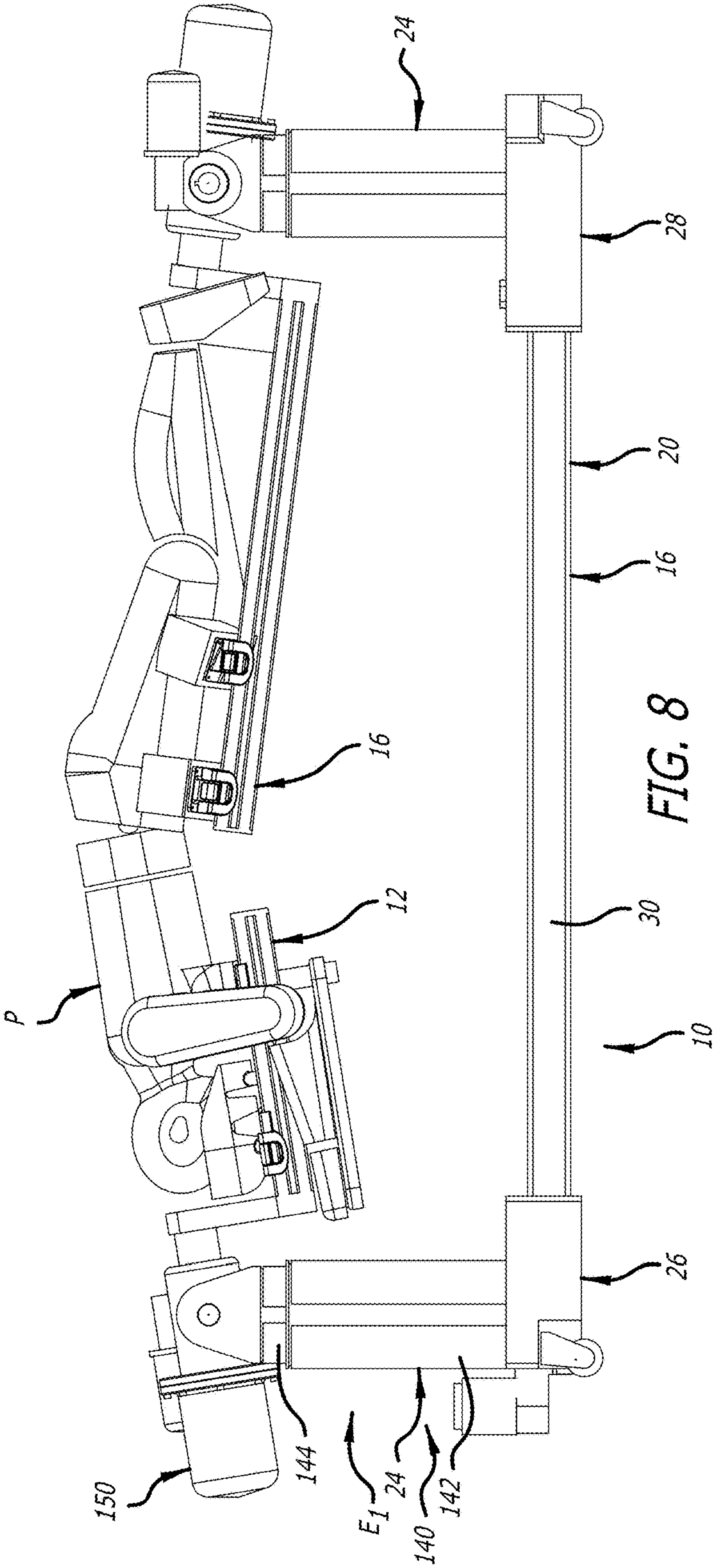
FIG. 8 is a side, elevational view that illustrates the first and second portions of the surgical table of FIG. 1A and the corresponding first and second portions of the patient supported thereon lowered and tilted upwardly relative to another.

Furthermore, the positions/orientations of the first support platform 12 and the second support platform 12, via actuation of the telescoping column 140 and the tilt portions 160 of the first vertically-oriented portion 22 and the second vertically-oriented portion 24, can be adjusted to bend the patient's body from the neutral position/orientation as depicted in FIG. 6, to move the head and upper torso downwardly and/or move the legs downwardly to introduce degrees of flexion to the patient's spine as depicted in FIG. 8.

In addition to the extension and the flexion of the patient's spine discussed above, the first portion of the patient's body supported by the first platform portion 12 and the second portion of the patient's body supported by the second platform portion 16 can be twisted relative to one another to introduce torsion therebetween via actuation of the rotational portions 154 of the first vertically-oriented portion 22 and the second vertically-oriented portion 24. Furthermore, the telescoping columns 140 of the first vertically-oriented portion 22 and the second vertically-oriented portion 24 can also be actuated (without tilting or twisting) to raise the first portion of patient's body supported by the first platform portion 12 relative to the second portion of the patient's body supported by the second platform portion 16, or vice versa. And, the sagittal position of the first portion relative to the second portion of the patient's body can be adjusted by operation of the slider portion 40 and the rotatable portion 42, and the patient's body can be stretched or contracted by operation of the slider portion 100.

Figure 9:
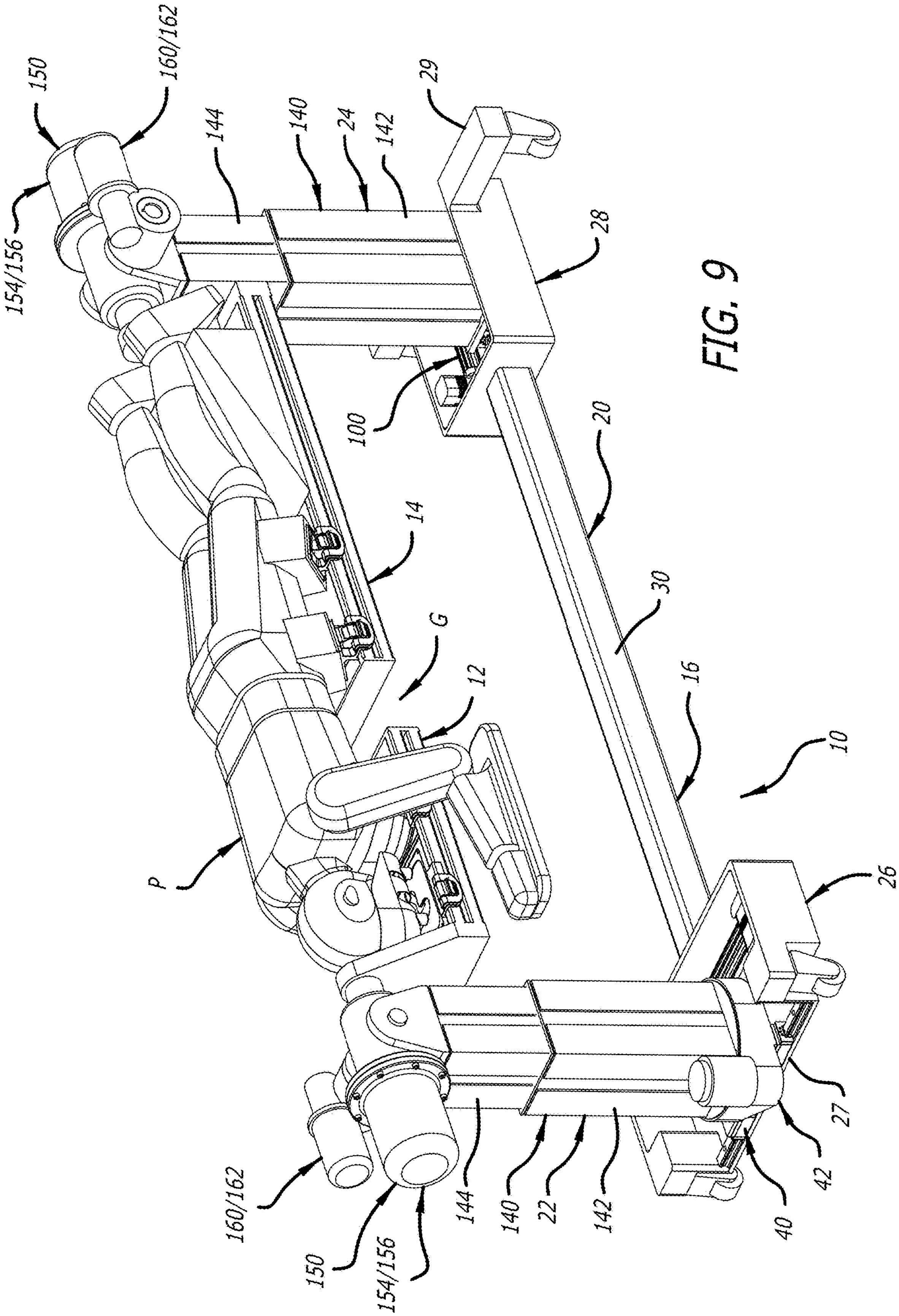
FIG. 9 is a side, perspective view that illustrates the patient positioned on the surgical table of FIG. 1A with the first portion of the patient positioned on the first platform portion and the second portion of the patient positioned on the second platform portion in a neutral position.
Figure 10:
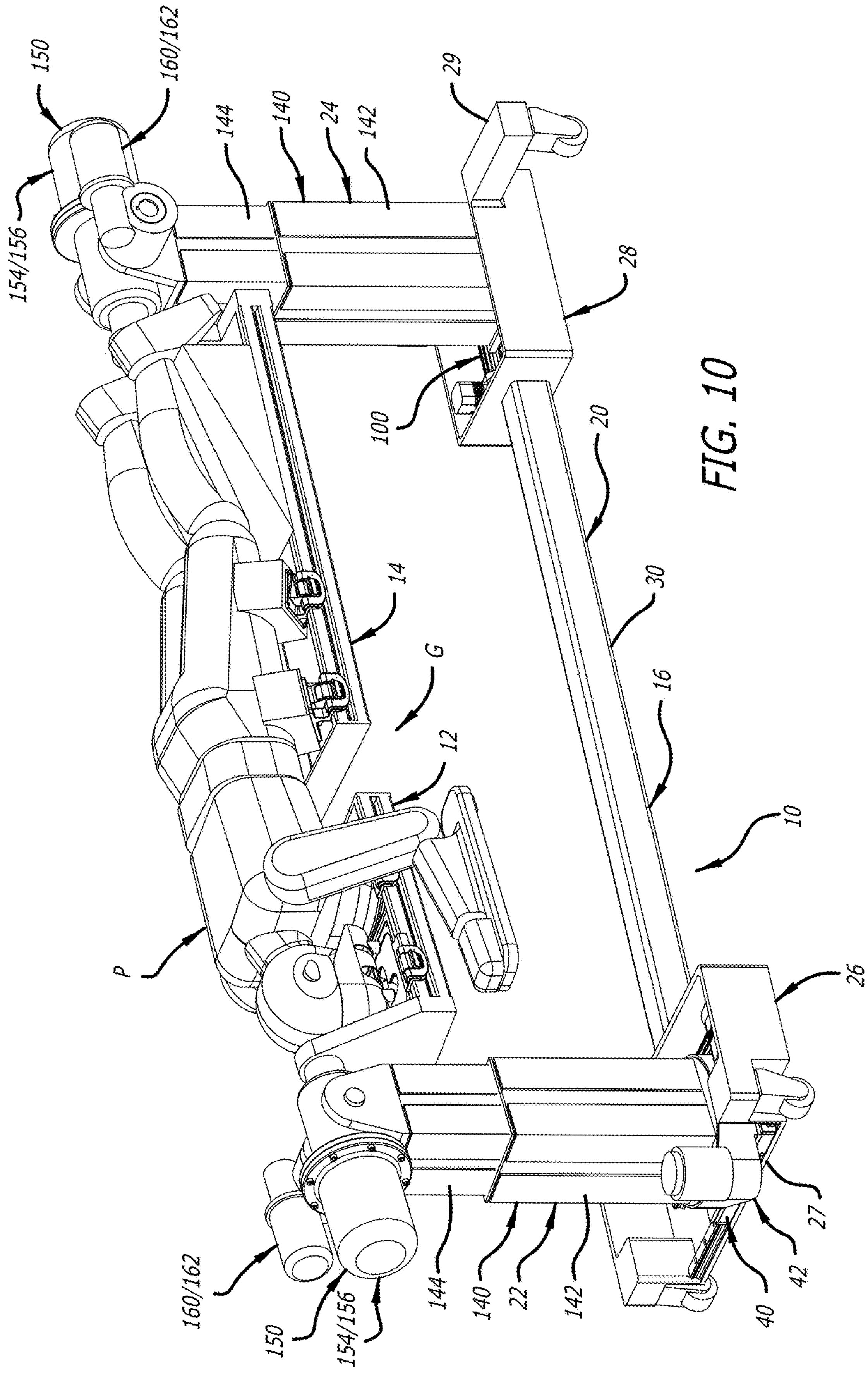
FIG. 10 is a side, perspective view similar to FIG. 9 showing sagittal adjustment of the position/orientation of the patient via movement of the first platform portion relative to the second platform portion.
Figure 11:
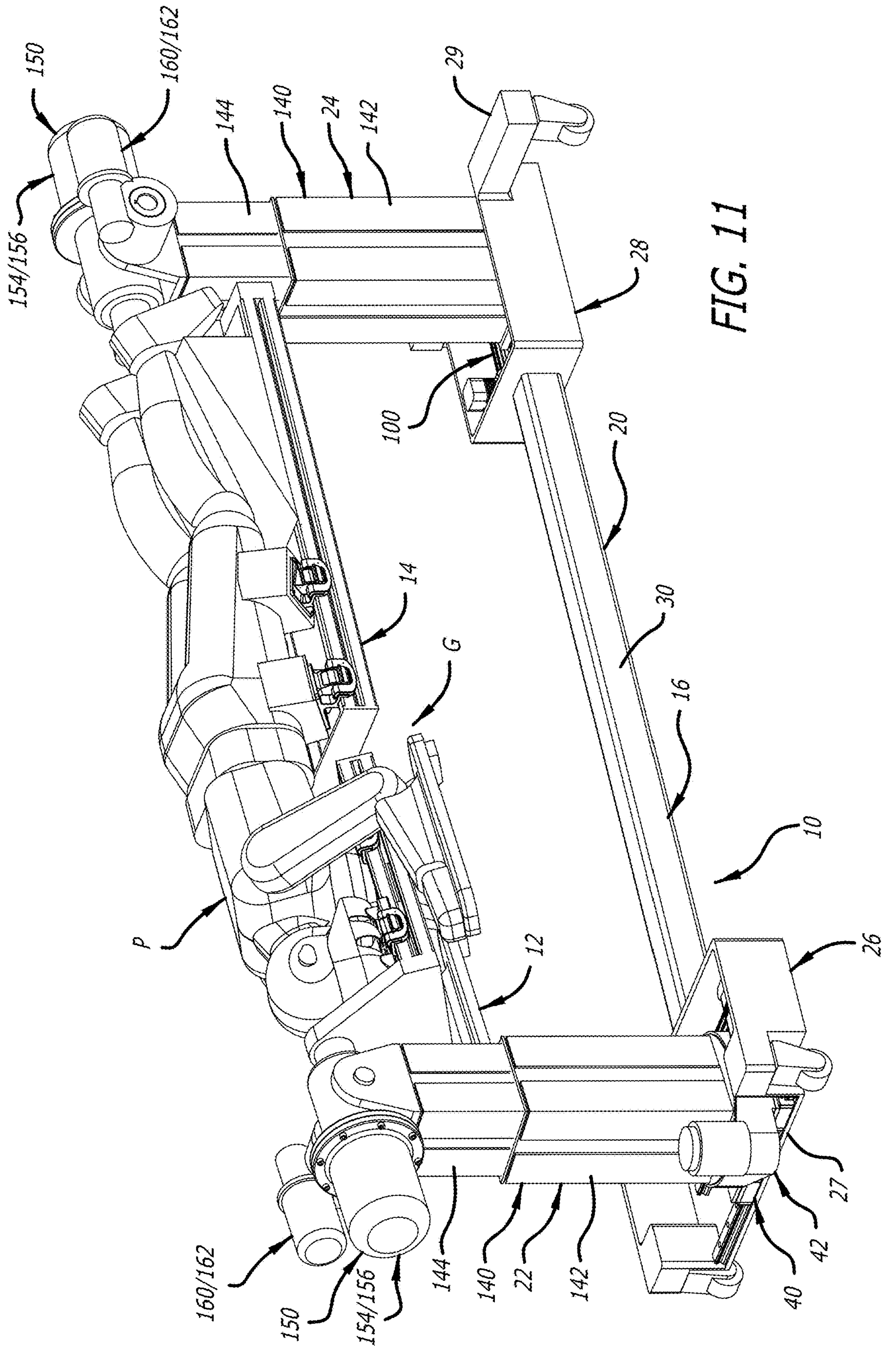
FIG. 11 is a side, perspective view similar to FIGS. 9 and 10 showing torsional adjustment in addition to the sagittal adjustment of the position/orientation of the patient via movement of the first platform portion and the second platform portion relative to one another.
Figure 12:
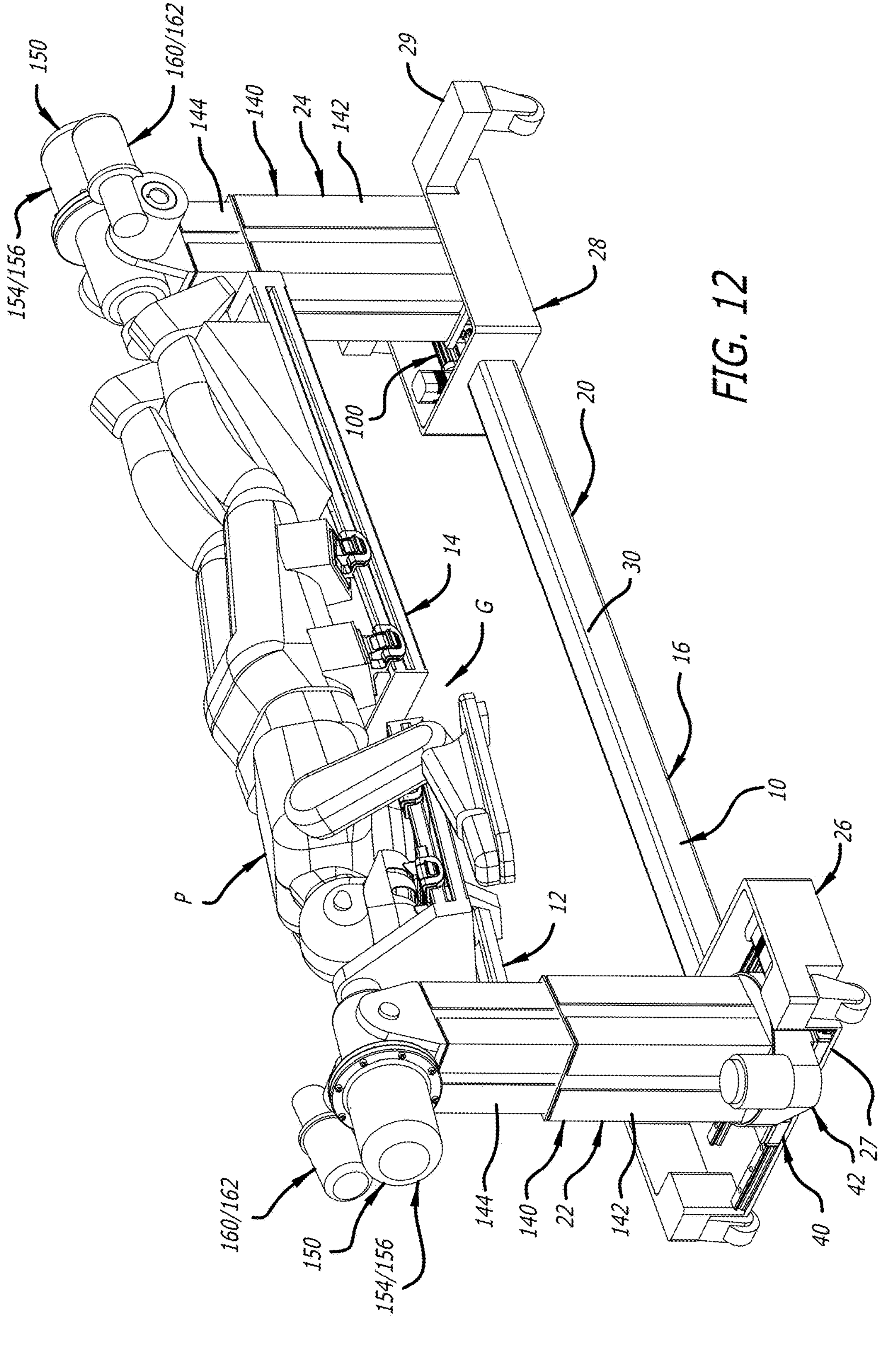
FIG. 12 is a side, perspective view similar to FIGS. 9-11 showing extensional adjustment in addition to the sagittal and torsional adjustment of the position/orientation of the patient via movement of the first platform portion and the second platform portion relative to one another.

As depicted in FIG. 9, the patient P is positioned/oriented in neutral position/orientation, and thereafter in FIGS. 10-12, independent adjustment of the first platform portion 12 and the second platform portion 14 relative to one another is used to adjust the position/orientation of the first portion of the patient's body supported by the first platform portion 12 and the second portion of the patient's body supported by the second platform portion 14 relative to one another. As depicted in FIG. 10, the slider portion 40 can be actuated to move the first platform portion 12 in a direction transverse to the mid-longitudinal axis L2, and the rotator portion 42 can be actuated to rotate the first platform portion 12 about a vertically-oriented axis. In doing so, the sagittal position/orientation of the patient P can be adjusted, as depicted in FIG. 10, via relative adjustment of the first platform portion 12 with respect to the second platform portion 14 using the slider portion 40 and the rotator portion 42. Then, as depicted in FIG. 11, the first platform portion 12 can be rotated via actuation of the rotational portion 154 and the second platform portion 14 can be moved closer to the first platform portion 12 via actuation of the slider 100 to adjust the torsional position/orientation (in addition to the adjusted sagittal position) of the first portion and the second portion of the patient P relative to one another. And, as depicted in FIG. 12, the first platform portion 12 can be raised and tilted via respective actuation of the telescoping column 140 and the tilt portion 160 of the first vertically-oriented portion 22, and the second platform portion 14 can be lowered via actuation of the telescoping column 140 of the second vertically-oriented portion 24 to adjust the extensional position/orientation (in addition to the adjusted sagittal and torsional position/orientation) of the first portion and the second portion of the patient P relative to one another.

Accordingly, the actuation of the telescoping columns 140, the rotational portions 154, tilt portions 160, the slider portions 40, the rotational portions 42, and/or the slider portion 100 can be used to independently adjust the relative positions and orientations of the first platform portion 12 and the second platform portion 16. And the relative movement of the first platform portion 12 and the second platform portion 16 can be used to adjust the position/orientation of the patient's body P before, during, and after surgery. As discussed above, the surgical table 10 can include a controller or controllers for controlling actuatable portions thereof to facilitate the operation thereof to coordinate movement therebetween. And such coordinated movement via the controller or controllers, for example, can be used to manipulate and prevent over-extension or over-flexion of the spine of the patient before, during, and after surgery. Thereafter, when the surgery is complete, the patient can be removed from the first platform portion 12 and the second platform portion 14.

Portions of the interface I of FIGS. 13-27 can be incorporated on a modified version of the surgical table 10 (discussed hereinabove) referenced by the identifier 10' and in a gantry Y. As depicted in FIG. 15, for example, the surgical table 10' can include similar features to the surgical table 10, and identical numbering will be used to denote these similar features. And as depicted in FIGS. 13, 14, and 16-27, the gantry Y can be stationary and can be used in conjunction with a surgical robotic system R that can be supported by and/or integrated with the gantry Y. While the interface I is depicted in FIGS. 15, 16-21, and 23-27 as being used with the surgical table 10', the interface I is not so limited, and the interface I can be used with other surgical tables.

As discussed below, portions of the interface I incorporated on the surgical table 10' can be positioned relative to and then docked with portions of interface I incorporated on or relative to the gantry Y. The use of the interface I, as depicted in FIGS. 16-19, allows the surgical table 10' to be docked to the gantry Y from either lateral side thereof, and such side-loading of the surgical table 10 affords initial placement of portions of the patient P in close proximity to the surgical robotic system R. The docking of the surgical table 10' moveably interconnects to the surgical table 10' relative to the gantry. Thereafter, actuation of the interface I affords movement (FIGS. 20 and 21) of the surgical table 10' relative to the gantry Y. The movement afforded by the interface I can be used to position and reposition a patient P supported by the surgical table 10' relative to the gantry Y and the surgical robotic system R in a cranial-caudal direction. As such, the patient P can be positioned before, during, and after surgery relative to the surgical robotic system R so that the surgical robotic system R can aid and/or perform surgery on the patient P. Furthermore, an operational area of the surgical robotic system R is correspondingly increased via using of the interface I and the movement of the surgical table 10' relative to the gantry Y afforded thereby. Thus, the surgical robotic system R can reach significant portions of the bony anatomy of the patient P using the interface I, the surgical table 10', and the gantry Y.

Figure 13:
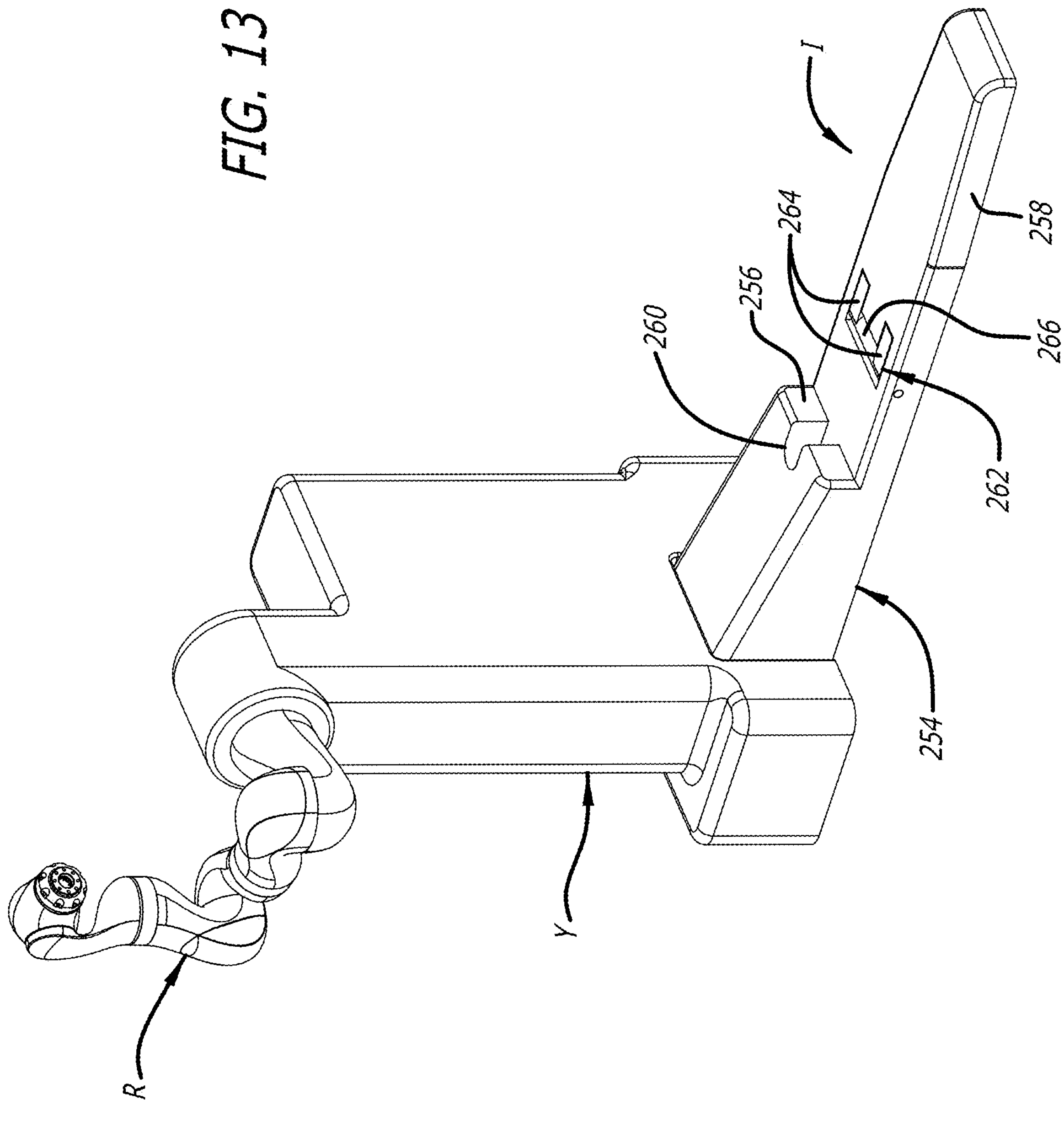
FIG. 13 is a side, perspective view that illustrates a gantry and a surgical robotic system supported by the gantry of the present disclosure, with the gantry incorporating a portion of an interface, for moveably interconnecting the gantry to an embodiment of the surgical table of the present disclosure, in a disengaged position.
Figure 19:
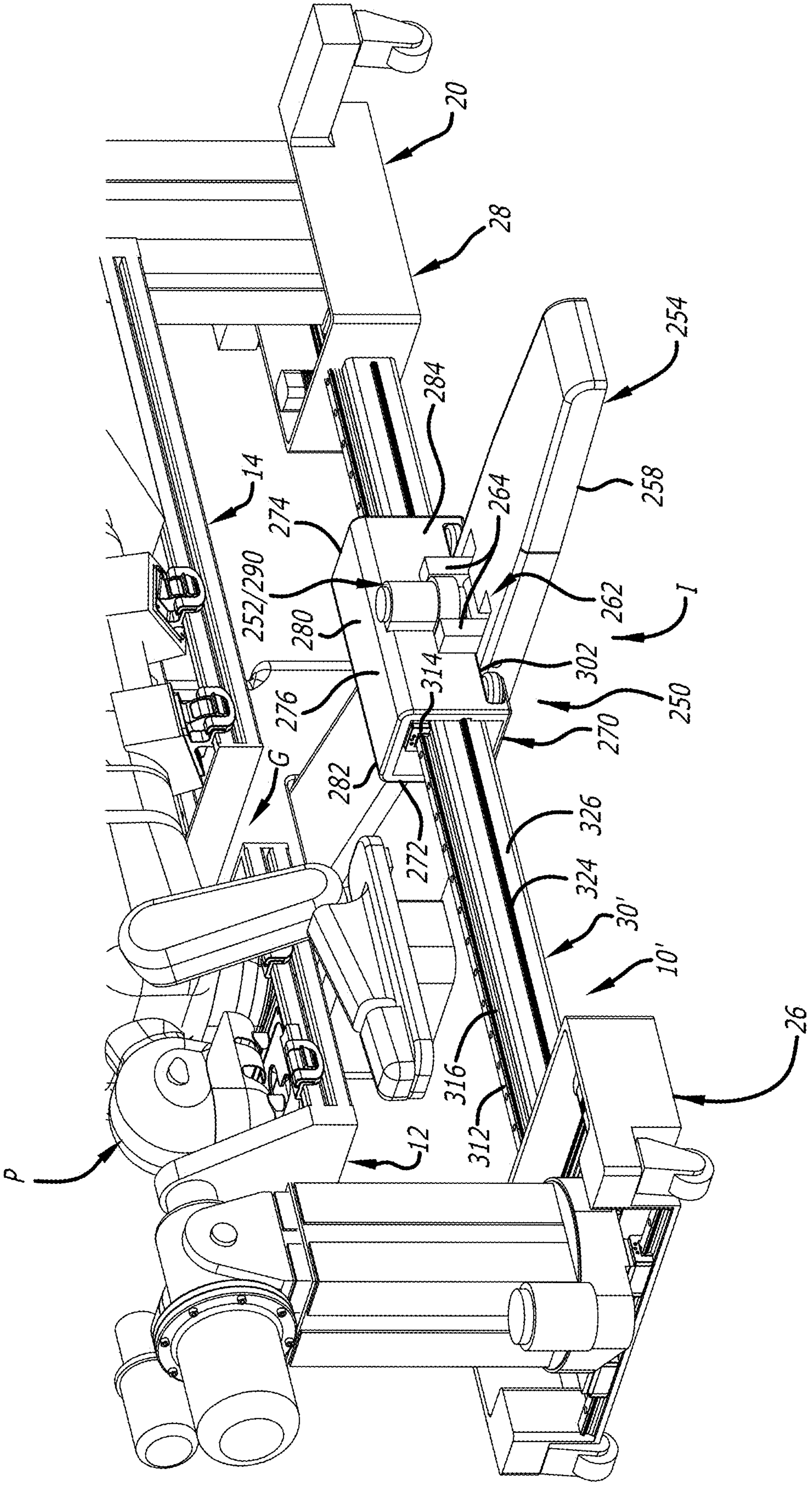
FIG. 19 is a side, perspective view similar to FIG. 18 that illustrates the surgical table of FIG. 15 positioned relative to the gantry of FIG. 13 with the portion of the interface of the gantry in the engaged position relative to the collar portion of the surgical table.

As depicted in FIG. 19, the interface I includes a first portion 250 attached to the surgical table 10' that can include a first actuator 252 actuatable to facilitate movement of the surgical table 10' and adjust the position thereof relative the gantry Y and the surgical robotic system R. Furthermore, as depicted in FIGS. 13 and 14, the interface I also includes a second portion 254 incorporated on or relative to the gantry Y.

The second portion 254 can be attached to and/or supported relative to the gantry Y, and can include a shoulder portion 256 and an outrigger portion 258. As depicted in FIGS. 13 and 14, the shoulder portion 256 can be attached to the gantry Y, and the outrigger portion 258 can extend outwardly from the shoulder portion 256. As discussed below, portions of the shoulder portion 256 can abut portions of the first portion 250 of the interface I, and portions of the first portion 250 of the interface I can be docked to the outrigger portion 258 to facilitate interconnection of the surgical table 10' and the gantry Y. And the shoulder portion 256 can include an indentation 260 for receiving a portion of the first portion 250 of the interface I attached to the surgical table 10'.

Figure 14:
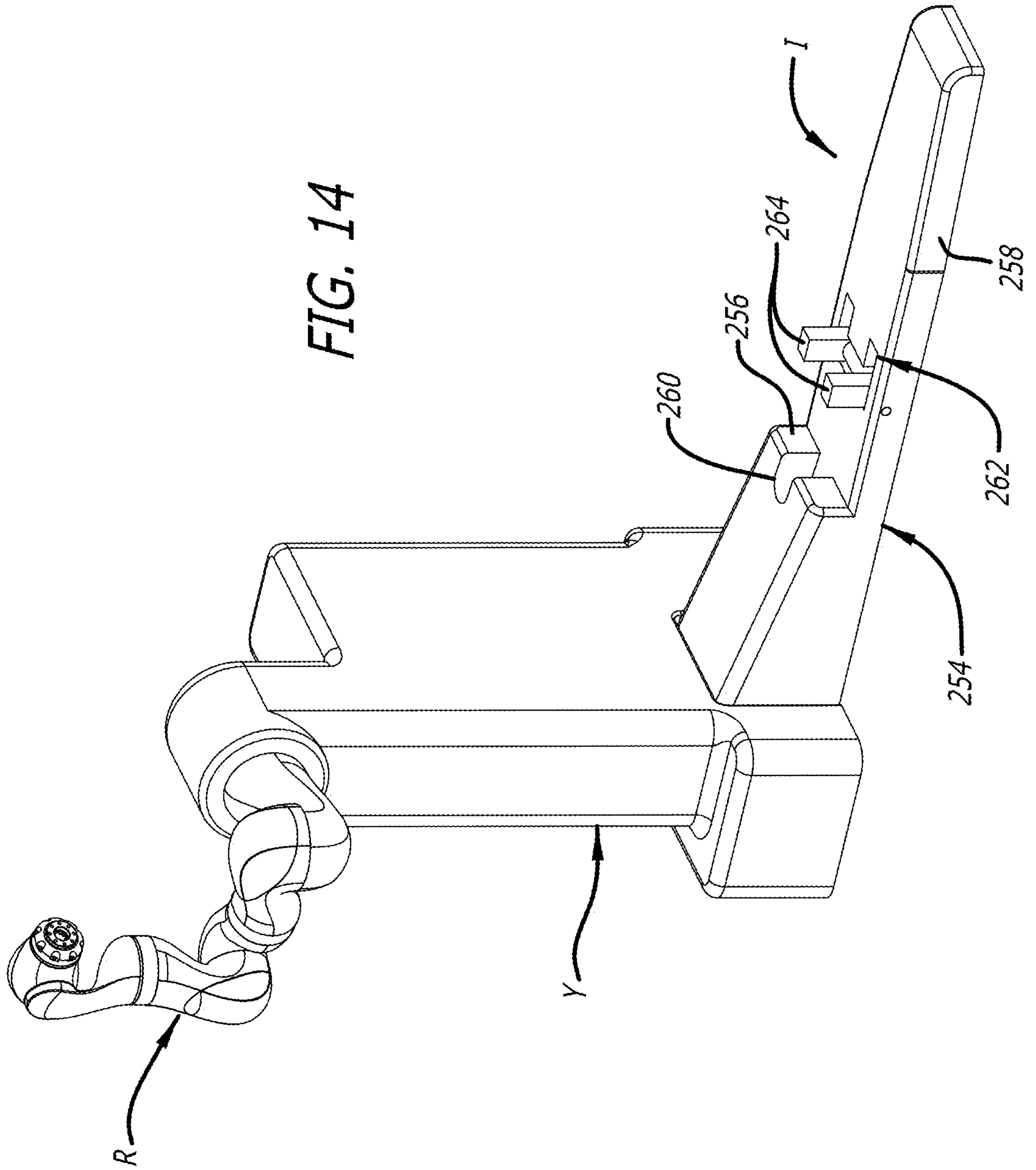
FIG. 14 is a side, perspective view similar to FIG. 13 that illustrates the portion of the interface of the gantry in an engaged position.
Figure 15:
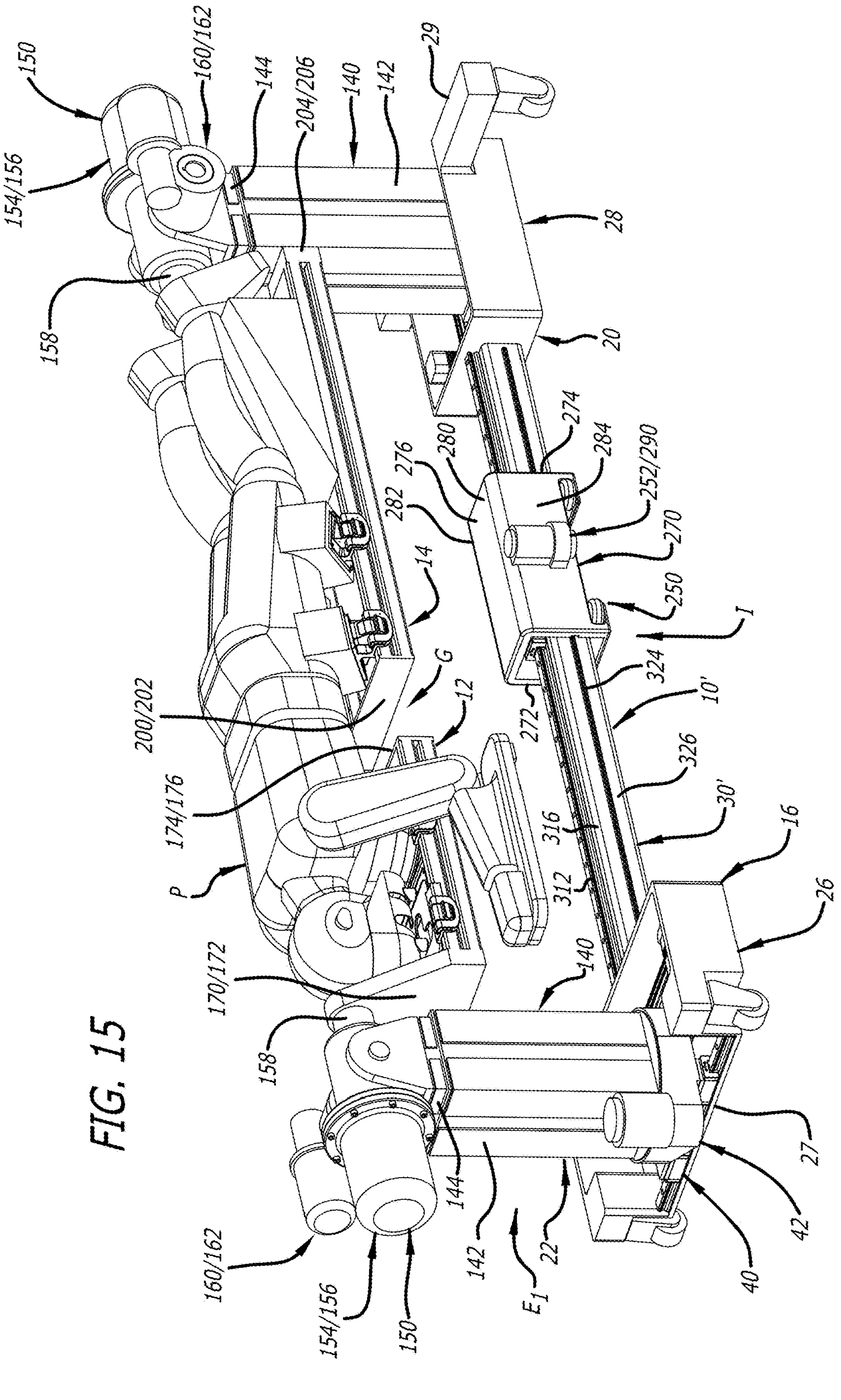
FIG. 15 is a side, perspective view of a surgical table of the present disclosure that illustrates the surgical table incorporating a collar portion of the interface thereon that includes a first actuator for facilitating movement afforded by the interface in a cranial-caudal direction.

Additionally, as depicted in FIGS. 13, 14, 18, and 19, the second portion 254 of the interface I can include a locking portion 262 serving to retain the portions of the first portion 250 of the interface I provided on the surgical table 10' in position relative the second portion 254. The locking portion 262 can incorporate all or portions of the shoulder portion 256, and can include an engagement portion in the form of one or more post portions 264 and a rotator 266 included in the outrigger portion 258, and the one or more post portions 264 are moveable upwardly and downwardly via rotation of the rotator 266 between an undeployed position (FIGS. 13 and 18) and a deployed position (FIGS. 14 and 19). As discussed below, when in the undeployed position, the post portions 264 are retracted into the outrigger portion 258 to afford passage of the first portion 250 attached to the surgical table 10', and when in the deployed position, the one of more post portions 264 are engaged to and retain the first portion 250 attached to the surgical table 10' in position relative to the gantry Y. The locking portion 262 can include an actuator (not shown) including a motor and a transmission (not shown) for driving movement of the post portions 264. While operation of the locking portion 262 is automated using the motor and transmission, the present disclosure is not limited thereto, and the actuation of the locking portion 262 can be manual.

As depicted in FIG. 19, the first portion 250 of the interface I can include a collar portion 270 attached to and moveably supported by the surgical table 10'. As discussed below, a modified longitudinal cross member 30' of the horizontally-oriented portion 20 of the support portion 16 of the surgical table 10' is received through the collar portion 270. The collar portion 270 includes a first end 272, a second end 274, and a body portion 276 extending between the first end 272 and the second end 274. As depicted in FIG. 15, the first actuator 252 is attached to the collar portion 270, and can include a motor and a transmission (not shown). Actuation of the first actuator 252 serves in facilitating movement of the cross member 30' relative to the collar portion 270, the surgical robotic system R, and the gantry Y (when the collar portion 270 is attached relative to the gantry Y). And as discussed above, such movement can be used to adjust the position of the patient P supported by the surgical table 10' relative to the surgical robotic system R before, during, and after surgery.

Figure 16:
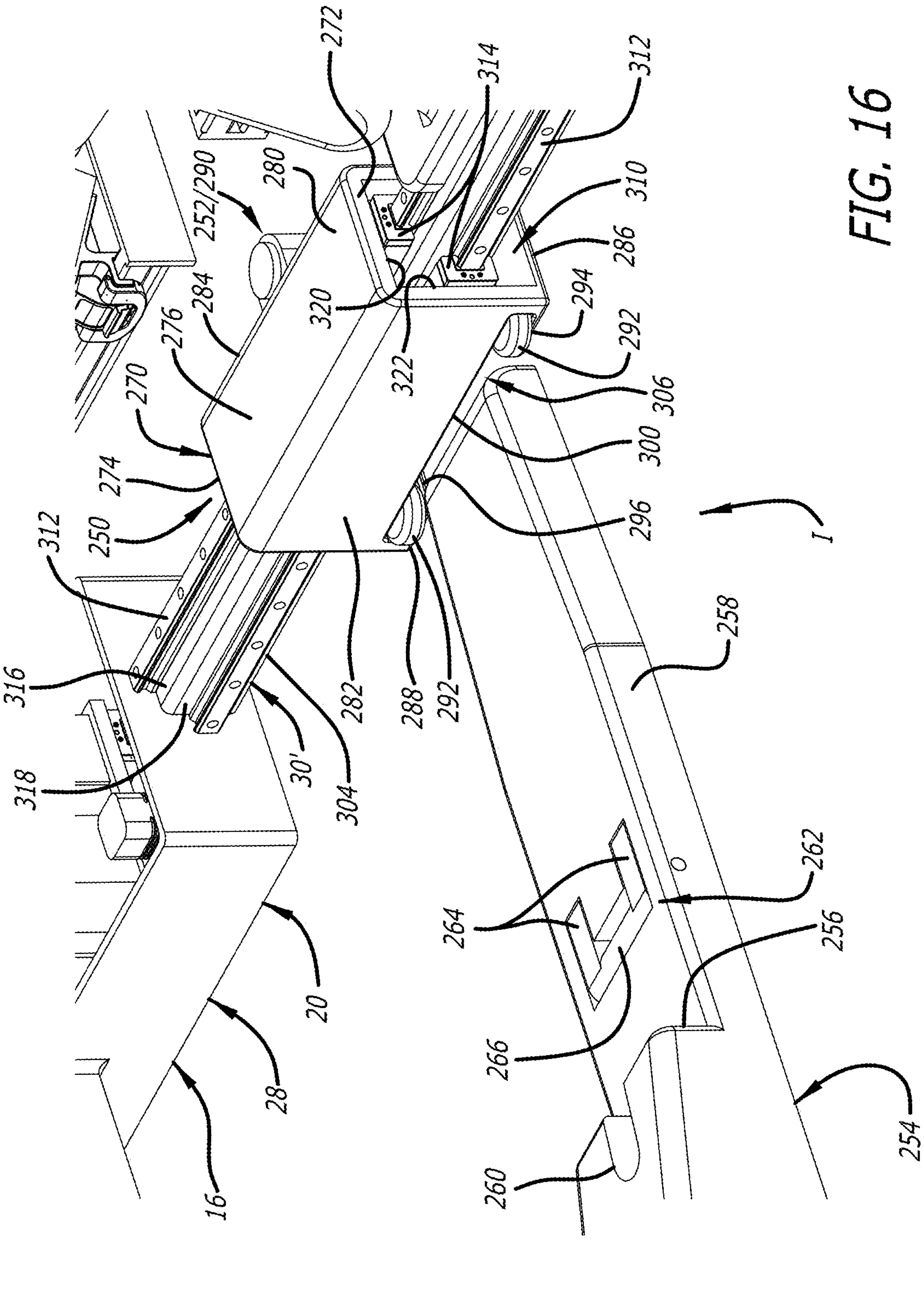
FIG. 16, is a side, perspective view of the collar portion included on the surgical table of FIG. 15 and the gantry of FIG. 13 that illustrates the collar portion being positioned relative to the portion of the interface of the gantry.

The body portion 276 includes an upper wall 280, a first sidewall 282, a second sidewall 284, a first lower wall 286, and a second lower wall 288. As depicted in FIG. 16, the first actuator 252 includes a housing 290 that can be attached to the second sidewall 284. Furthermore, the first lower wall 286 extends from inwardly from the first end 272, the second lower wall 288 extends inwardly from the second end 274, the first lower wall 286 supports one or more of bumpers 292, and the second lower wall 288 also supports one or more of the bumpers 292. As depicted in FIG. 16, the bumpers 292 can be wheels for rolling along portions of the outrigger portion 258. The wheels 292, an inner edge 294 of the first lower wall 286, an inner edge 296 of the second lower wall 288, a lower edge 300 of the first sidewall 282, and a lower edge 302 of the second sidewall 284, together with a bottom surface 304 of the cross member 30' define an outrigger-receiving area 306 (FIG. 16) in which portions of the outrigger portion 258 can be received.

Figure 17:
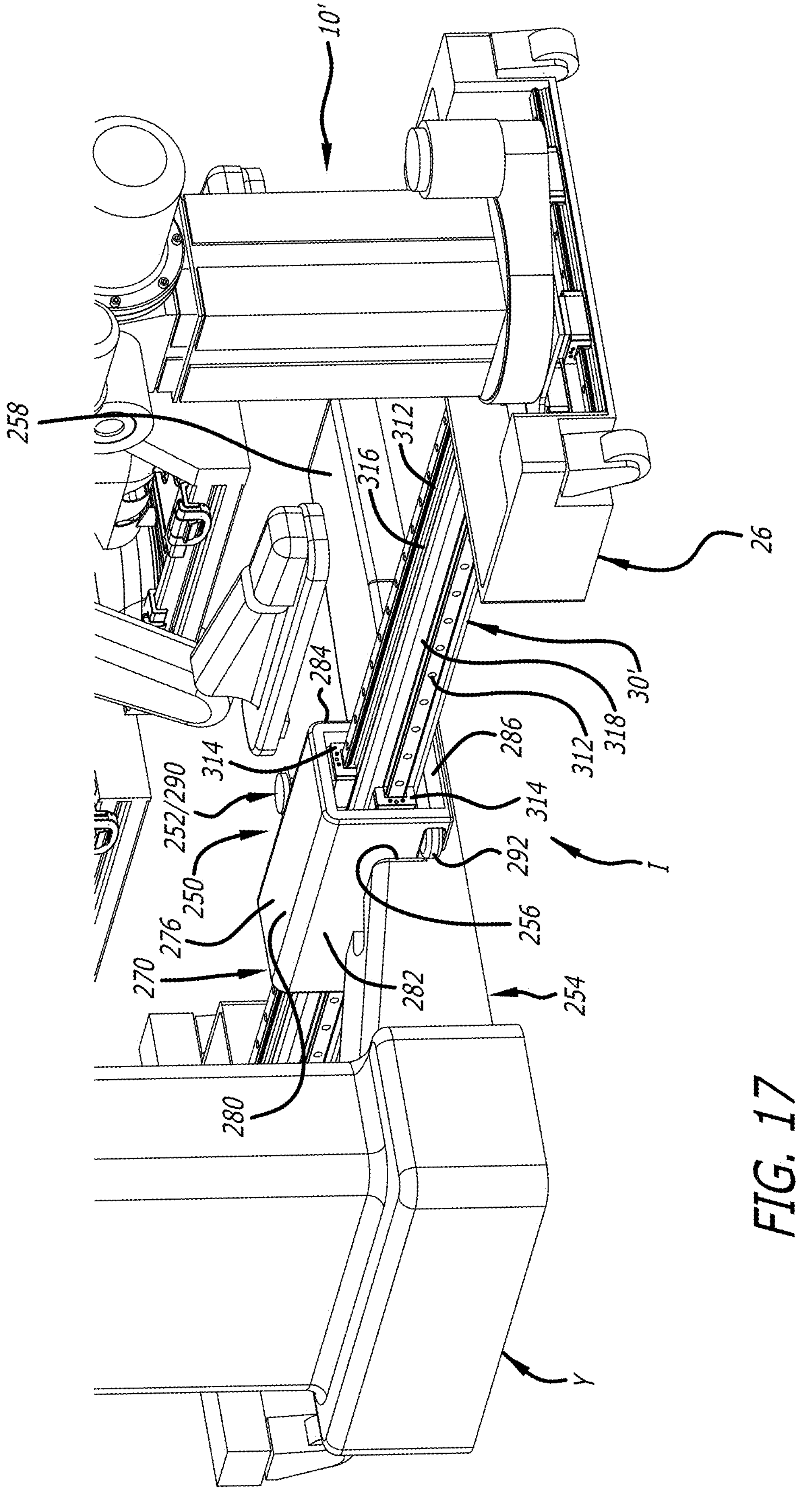
FIG. 17 is a side, perspective view of the collar portion included on the surgical table of FIG. 15 and the gantry of FIG. 13 that illustrates the collar portion in position relative to the portion of the interface of the gantry.

When positioning the surgical table 10' relative to the gantry Y, as depicted in FIGS. 16 and 17, the outrigger portion 258 can be inserted into the outrigger-receiving area 306, and the wheels 292 can be used guide movement (via contact of the wheels 292 with sidewalls of the outrigger portion 258) of the collar portion 270 of the first portion 250 of the interface I. Such guidance affords movement of the collar portion 270 (and the surgical table 10' attached thereto) into position so that either the first sidewall 282 (corresponding to a first orientation (FIGS. 18-21) of the surgical table 10' relative to the gantry Y) or the second sidewall 284 (corresponding to an opposite second orientation) of the surgical table 10' relative to the gantry Y) contacts the shoulder portion 256 of the second portion 254 of the interface I. If the first sidewall 282 is contacted to the shoulder portion 256, the housing 290 of the first actuator 252 is opposite from the indentation 260, and if the second the second sidewall 284 is contacted to the shoulder portion 256, the housing 290 of the first actuator 252 is received in the indentation 260.

After either the first sidewall 282 or the second sidewall 284 is contacted to the shoulder portion 256, the locking portion 262 can be actuated to move the post portions 264 from the undeployed position (FIGS. 13 and 18) to the deployed position (FIGS. 14 and 19). When the first sidewall 282 is contacted to the shoulder portion 256 and the housing 290 of the first actuator 252 is opposite from the indentation 260, the post portions 264 contact the second sidewall 284 and side portions of the housing 290 in the deployed position. And when the second sidewall 284 is contacted to the shoulder portion 256 and the housing 290 of the first actuator 252 is received in the indentation 260, the post portions 264 contact the first sidewall 282. Use of the post portions 264 in contacting the first sidewall 282 and the second sidewall 284, the contact of the post portions 264 with the side portions of the housing 290, and the receipt of the housing 290 in the indentation 260, serve in maintaining the position of the first portion 250 of the interface I (including the collar portion 270) relative to the second portion 254 of the interface I (including the shoulder portion 256 and the outrigger portion 258) and the gantry Y.

The modified cross member 30' of the horizontally-oriented portion 20 of the support portion 16 is received through the collar portion 270. To that end, as depicted in FIG. 16, the body portion 276 includes a cavity 310 extending between the first end 272 and the second end 274 for receiving the modified cross member 30'. The cavity 310 can be defined at least in part by the upper wall 282, the first sidewall 284, the second sidewall 286, the first lower wall 286, and/or the second lower wall 288. During movement of the cross member 30' relative collar portion 270, portions of the cross member 30' move into and out of the cavity 310. The first actuator 252 is configured to move the cross member 30' relative to the collar portion 270 gantry Y, and such movement readjusts the position of the surgical table 10' relative to the gantry Y and the surgical robotic system R. As such, the position of the surgical table 10' can be adjusted before, during, and after surgery, and such adjustment can serve to position and reposition the surgical robotic system R relative to the patient P supported by the surgical table 10'.

To facilitate movement of the cross member 30' relative to the collar portion 270, portions of the cross member, as depicted in FIG. 16, can include one or more tracks 312, and portions of the collar portion 270 can include one or more trucks 314 for operatively engaging the tracks 312. The operative engagement of the trucks 314 to the tracks 312 allows the cross member 30' to move relative to the collar portion 270 by sliding within the cavity 310. The tracks 312 can be provided on an upper surface 316 and a side surface 318 of the cross member 30'. To operatively engage the tracks 312, the one or more trucks 314 can be provided on an inner surface 320 of the upper wall 280 and an inner surface 322 of the first sidewall 282. The one or more trucks 314 provided on the inner surface 320 of the upper wall 280 engage the track 312 provided on the upper surface 316, and the one or more trucks 314 provided on the inner surface 322 of the first sidewall 282 engage the track 312 provided on the side surface 318.

Figure 18:
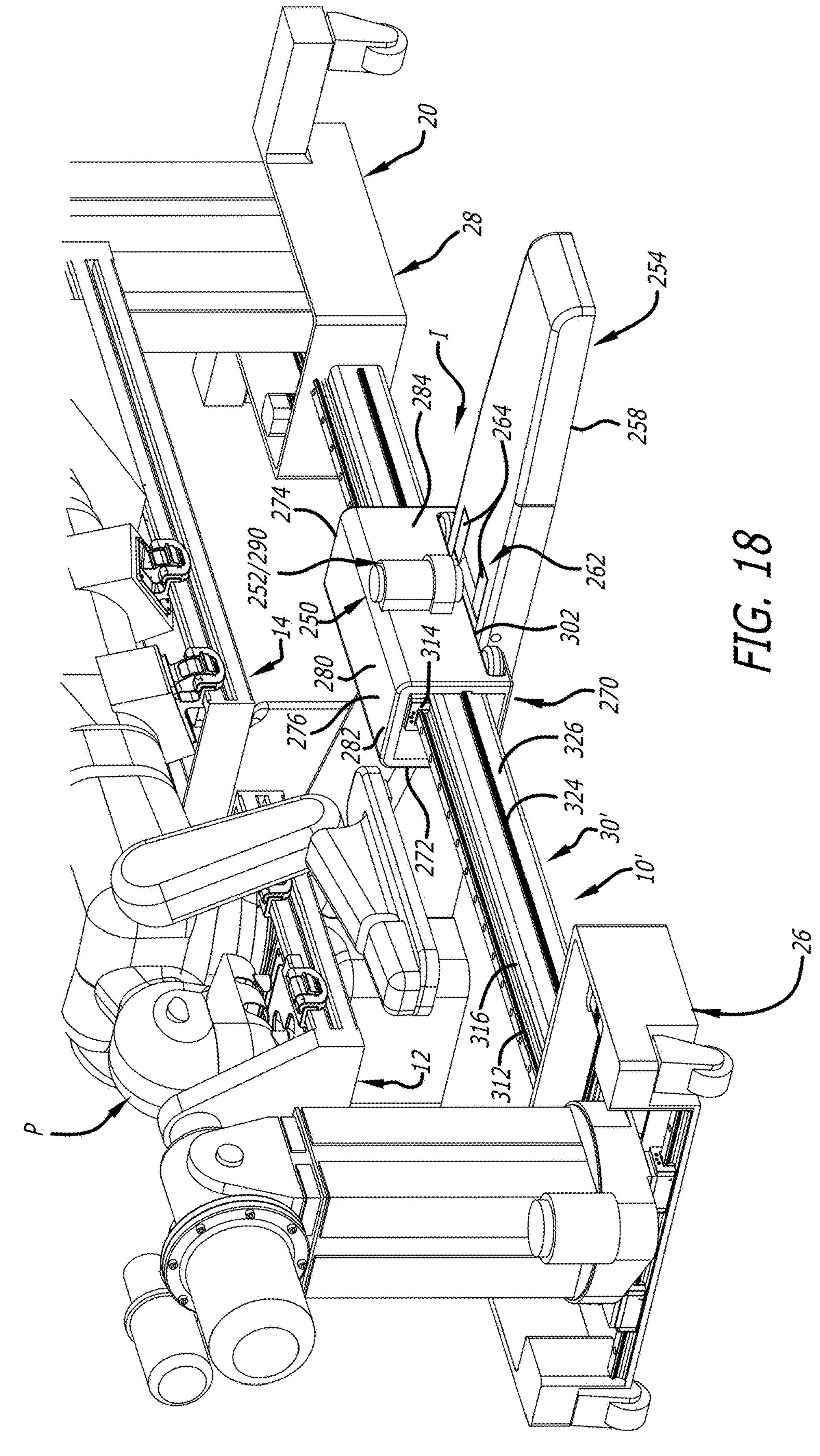
FIG. 18 is a side, perspective view of the surgical table of FIG. 15 positioned relative to the gantry of FIG. 13 that illustrates the portion of the interface of the gantry in the disengaged position relative to the collar portion of the surgical table.
Figure 20:
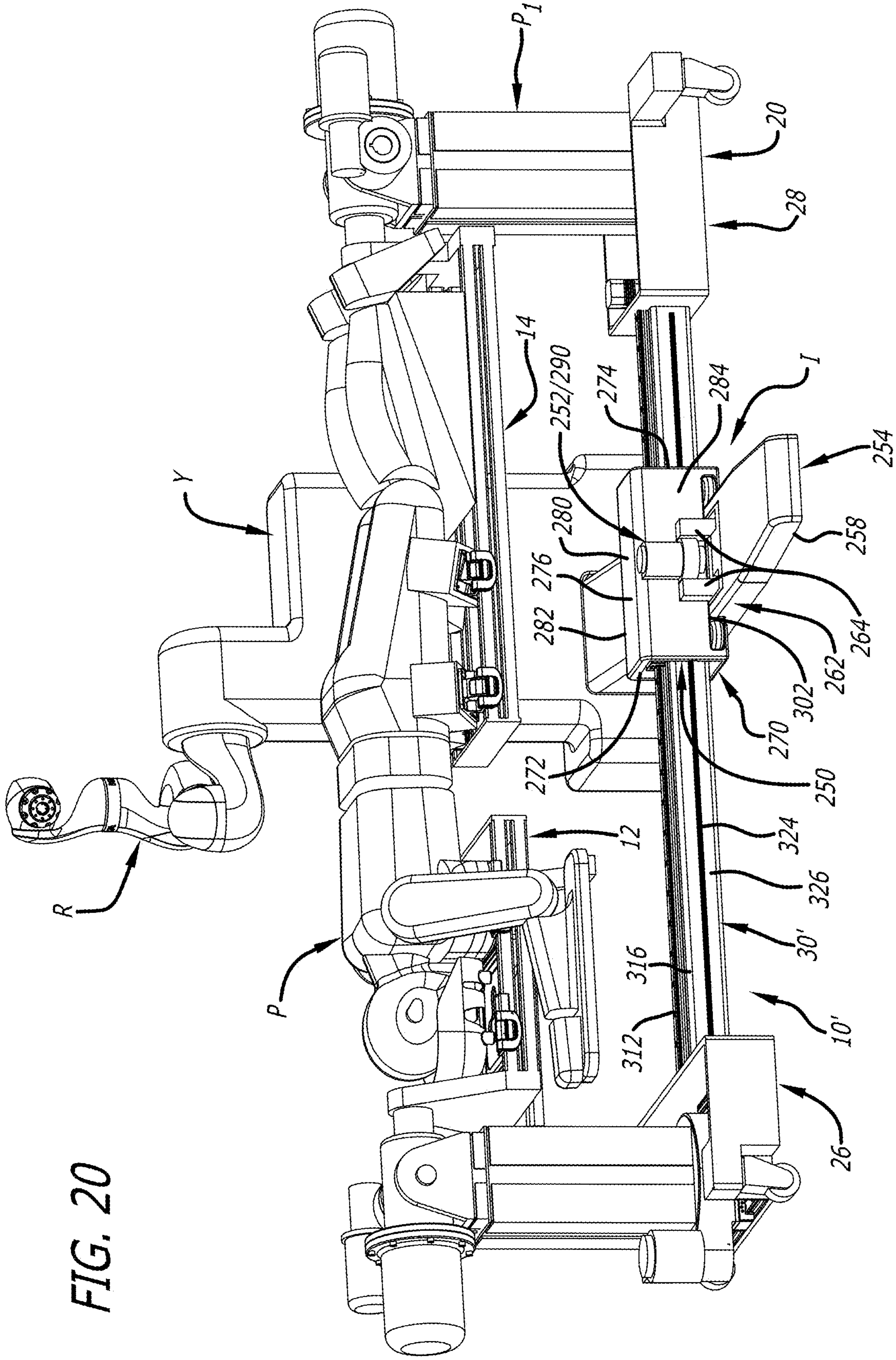
FIG. 20 is a side, perspective view of the surgical table of FIG. 15 positioned relative to the gantry of FIG. 13 that illustrates the surgical table in a first cranial-caudal position relative to the gantry before movement of the surgical table in the cranial-caudal direction via actuation of the first actuator.
Figure 21:
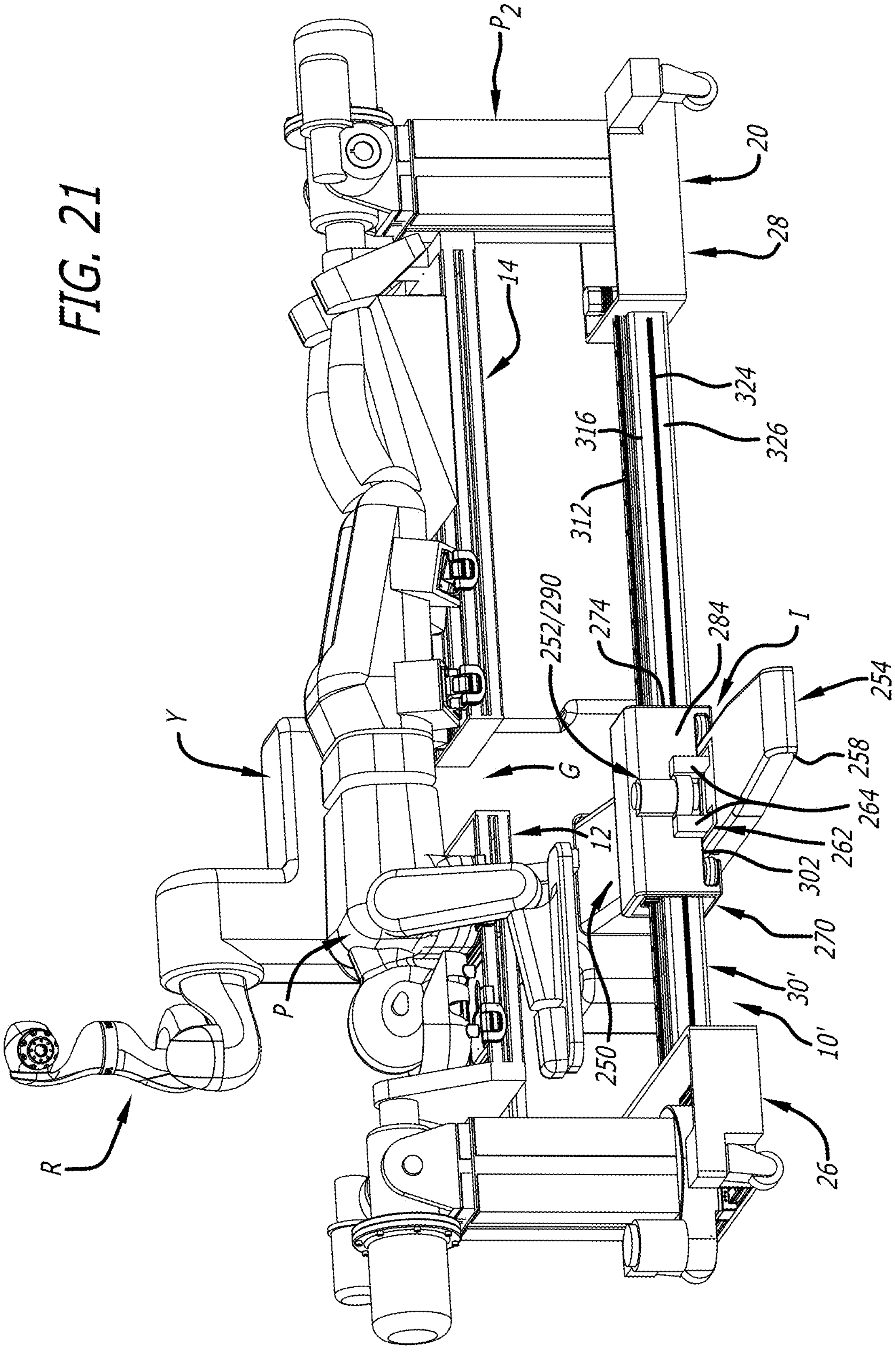
FIG. 21 is a side, perspective view similar to FIG. 20 that illustrates the surgical table of FIG. 15 positioned relative to the gantry of FIG. 13 with the surgical table moved to a second cranial-caudal position from the first cranial-caudal position relative to the gantry after movement of the surgical table in the cranial-caudal direction via actuation of the first actuator.

A first gear portion in the form of circular gear (or pinion) (not shown) can be provided in the cavity 310 and driven by the first actuator 252, and, in addition to the tracks 312, a second gear portion in the form of a linear gear (or rack) 324 can be provided on the modified cross member 30'. As depicted in FIGS. 18 and 19, the linear gear 324 can be provided on a side surface 326 of the cross member 30'. Furthermore, the circular gear can be attached to a shaft (not shown) that extends through the second sidewall 284, and the shaft can be rotated by operation of the first actuator 252. The circular gear can be engaged to the linear gear 324, and rotation of the circular gear via actuation of the first actuator 252 serves move the cross member 30' relative to the collar portion 270. For example, rotation of the circular gear in a first rotational direction can move the cross member 30' in a first linear direction relative to the collar portion 270, and rotation of the circular gear in an opposite rotational direction can move the cross member 30' in an opposite second linear direction relative to the collar portion 270. As such, rotation of the circular gear (via actuation of the actuator 252) serves in adjusting the position of the surgical table 10' relative to the gantry Y and the surgical robotic system R, as well as affording positioning and repositioning the patient P supported by the surgical table 10' in cranial-caudal directions relative to the surgical robotic system R. A first position P1 of the surgical table 10' is depicted in FIG. 20, and a second position P2 of the surgical table 10' is depicted in FIG. 21. Thus, such adjustment allows the patient P to be positioned before, during, and after surgery relative to the surgical robotic system R, so that the surgical robotic system R can perform and/or aid the performance of surgery on the patient P.

Figure 22:
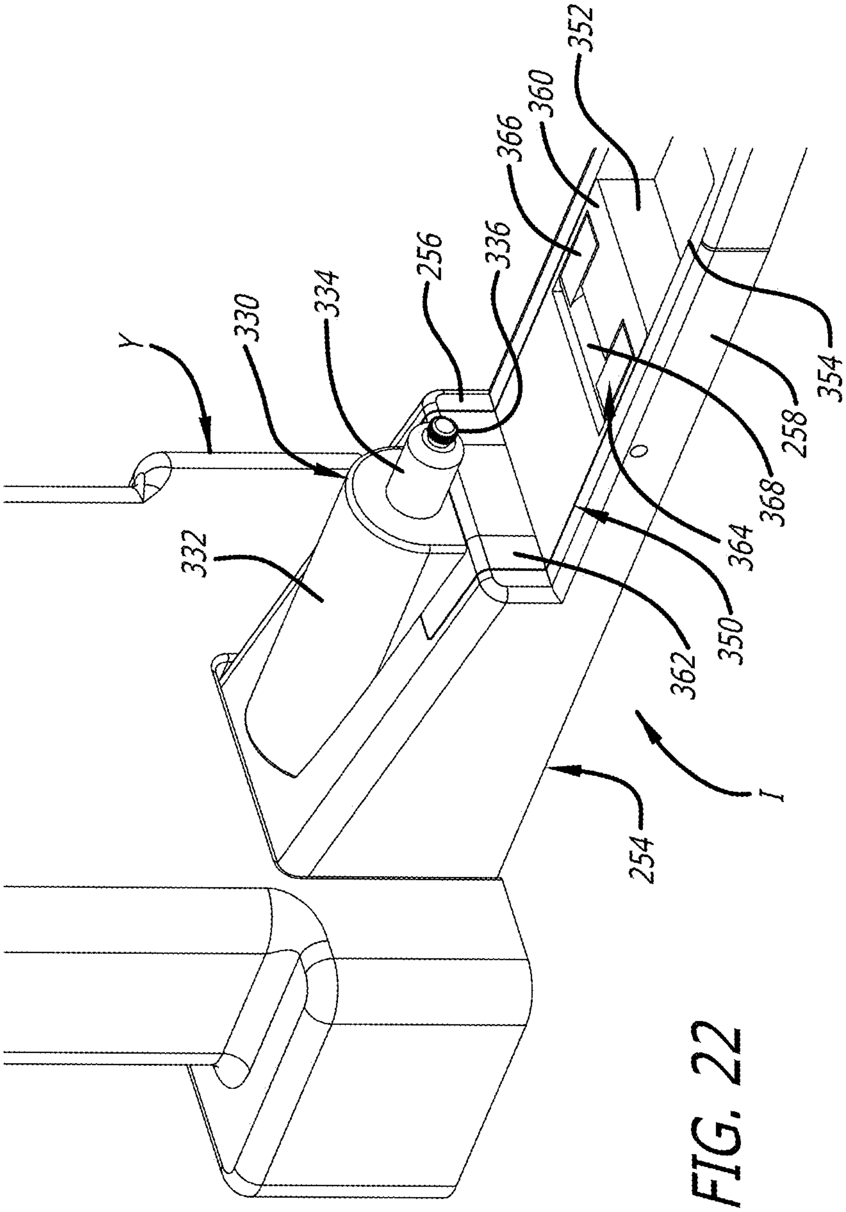
FIG. 22 is a side, perspective view of a portion of the interface included on the gantry that illustrates modifications including both a second actuator for facilitating movement of the surgical table of FIG. 15 in the cranial-caudal direction, and an actuatable slider portion for facilitating movement of the surgical table of FIG. 15 in a direction transverse to the cranial-caudal direction.

Rather than using the first actuator 252 attached to the collar portion 270, the gantry Y can be modified so that the second portion 254 of interface I can include a second actuator 330. For example, as depicted in FIGS. 21 and 22, portions of the second actuator 330 can be attached to the shoulder portion 256, and other portions of the actuator 330 can extend over the outrigger portion 258. The portions of the second actuator 330 extending over the outrigger portion 258 can include a projection portion 332, a shaft 334 extending outwardly from the projection portion 332, and the first gear portion in the form of a circular gear 336 attached to the shaft 334. Actuation of the second actuator 330 serves to rotate the shaft 334 and the circular gear 336 attached thereto.

Figure 23:
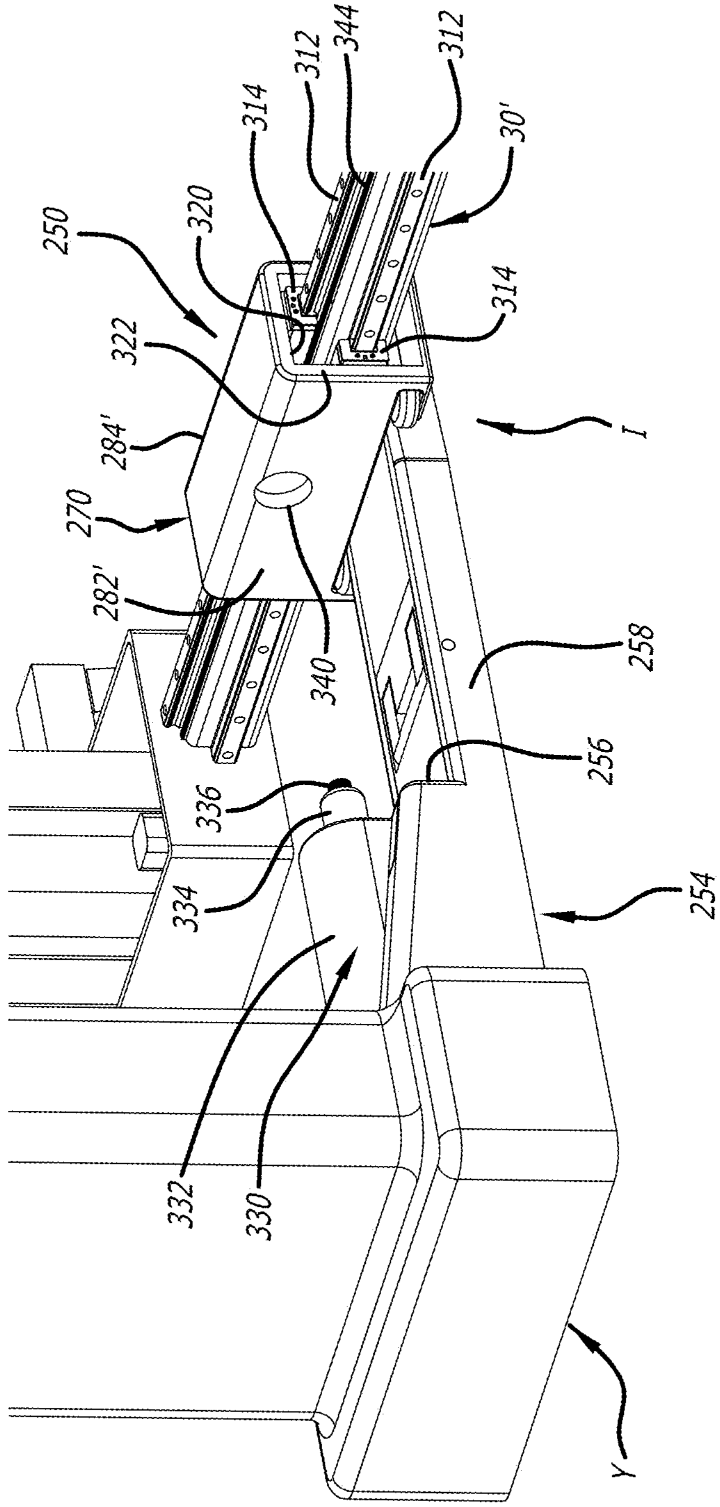
FIG. 23 is a side, perspective view of the collar portion of the interface and the gantry of FIG. 22 that illustrates modifications to the collar portion incorporated on the surgical table of FIG. 15, and the collar portion with the modifications being positioned relative to the portion of the interface of the gantry.
Figure 24:
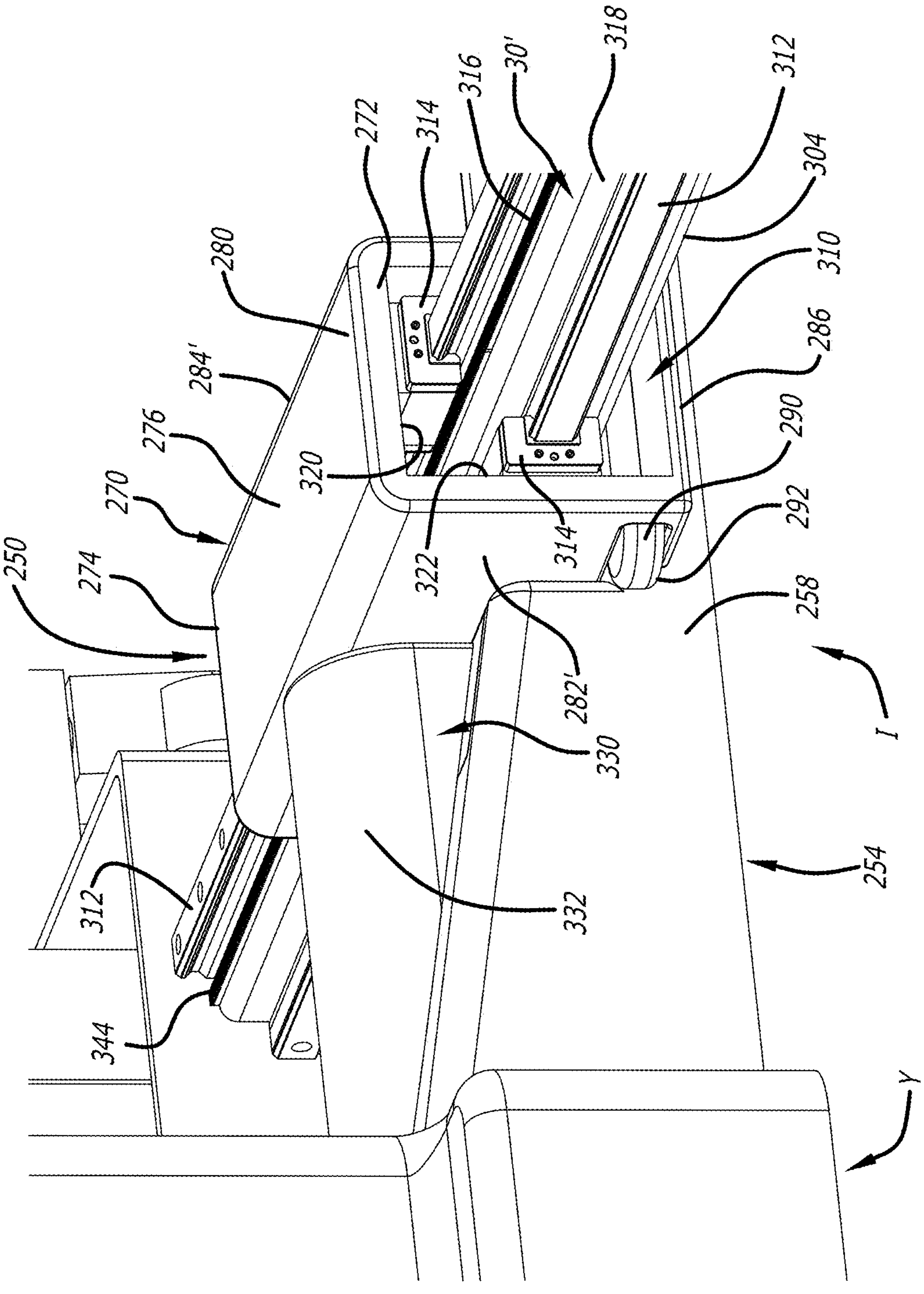
FIG. 24 is a side, perspective view of the collar portion of FIG. 23 and the portion of the gantry of FIG. 22 that illustrates the collar portion with the modifications incorporated on the surgical table of FIG. 15 in position relative to the portion of the interface of the gantry.
Figure 25:
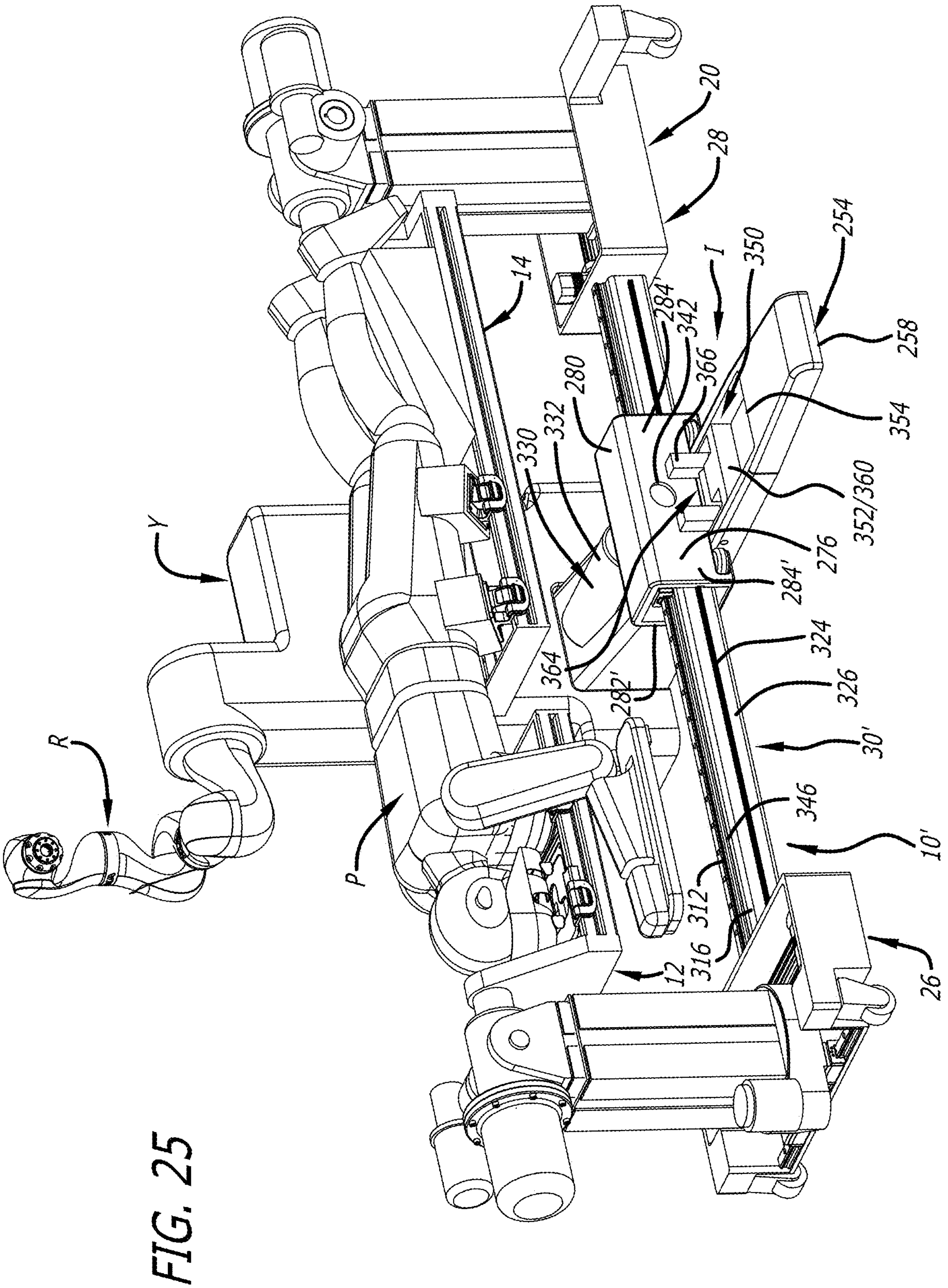
FIG. 25 is a side, perspective view of the surgical table of FIG. 15 incorporating the collar portion of FIG. 23 and the gantry of FIG. 22 that illustrates the collar portion in position relative to the gantry.

As depicted in FIGS. 23 and 25, the collar portion 270 can include a first opening 340 formed in a modified first sidewall 282' and/or a second opening 342 formed in a modified second sidewall 284'. When the outrigger portion 258 is received in the outrigger-receiving area 306 (FIG. 24), the projection portion 332, the shaft 334, and the circular gear 336 can be received through the first opening 340 if the modified first sidewall 282' is contacted to the shoulder portion 256, and the projection portion 332, the shaft 334, and the circular gear 336 can be received through the second opening 342 if the modified second sidewall 284' is contacted to the shoulder portion 256. When the circular gear 336 is inserted through the first opening 340, it can engage a first linear gear (or rack) 344 provided on the upper surface 316 on one side of the corresponding track 312 (FIG. 24). And when the circular gear 336 is inserted through the second opening 342, it can engage a second linear gear (or rack) 346 provided on the upper surface 316 on the other side of the corresponding track 312 (FIG. 25). When engaged to either the first linear gear 344 or the second linear gear 346, rotation of the circular gear 336 (via actuation of the actuator 330) serves in moving the cross member 30' in linear directions relative to the collar portion 270. As such, rotation of the circular gear 336 affords positioning and repositioning of the patient P supported by the surgical table 10' in cranial-caudal directions relative to the surgical robotic system R. Thus, such adjustment allows the patient P to be positioned before, during, and after surgery relative to the surgical robotic system R, so that the surgical robotic system R can perform and/or aid the performance of surgery on the patient P.

Figure 26:
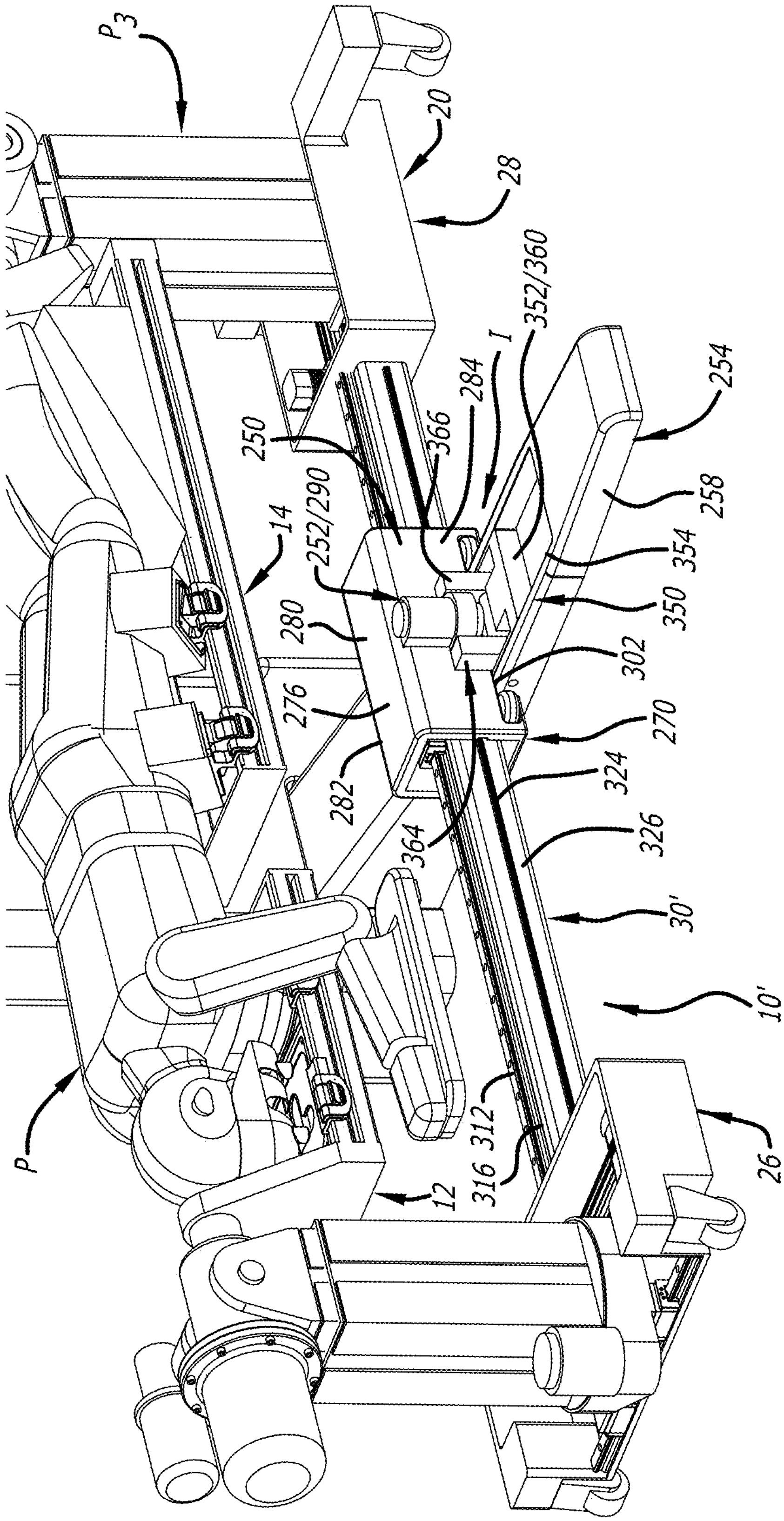
FIG. 26 is a side, perspective view of the surgical table of FIG. 15 positioned relative to the gantry modified to include the actuatable slider portion of the interface of FIG. 22 that illustrates the surgical table in a first transverse position relative to the gantry before movement of the surgical table in the direction traverse to the cranial-caudal direction via actuation of the actuatable slider portion.
Figure 27:
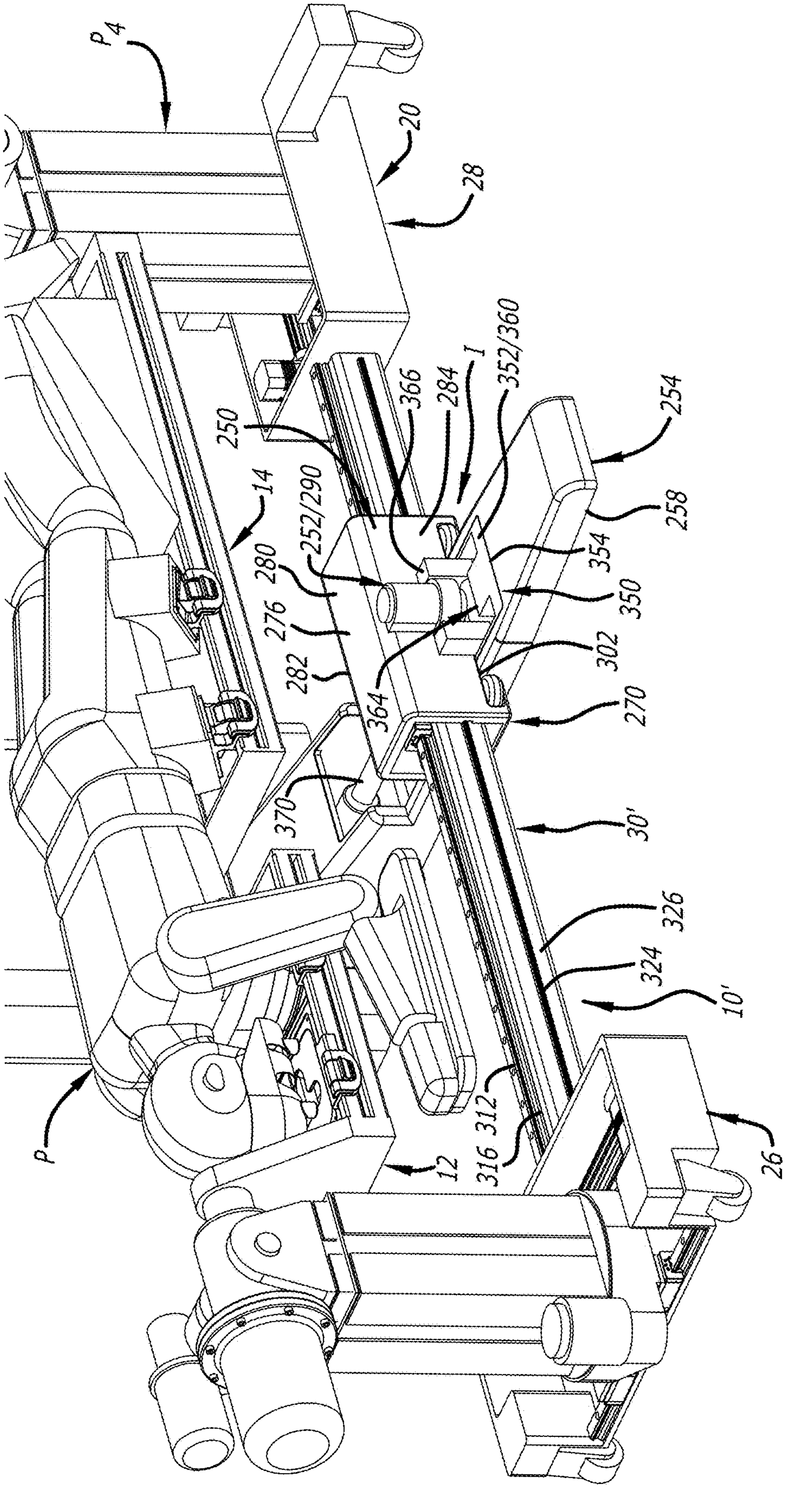
FIG. 27 is a side, perspective view similar to FIG. 26 that illustrates the surgical table of FIG. 15 positioned relative to the gantry including the actuatable slider portion of the modified interface of FIG. 22 with the surgical table moved to a second transverse position from the first transverse position relative to the gantry after movement of the surgical table in the direction transverse to the cranial-caudal direction via actuation of the modified interface.

In addition to being positionable and repositionable in cranial-caudal directions, the gantry Y also can be modified so that the second portion 254 of the interface I can include an adjustment portion 350 capable of moving the surgical table 10' and the patient P in transverse directions to the cranial-caudal directions. As depicted in FIGS. 22 and 25-27, the adjustment portion 350 includes an actuatable slider portion 352 and a recess 354 for receiving portions of the slider portion 352. The slider portion 352 includes a base portion 360, a wall portion 362, and a locking portion 364 including one or more post portions 366, and a rotator portion 368. The base portion 360 is received in the recess 354, the wall portion 362 extends upwardly from the base portion 360, and the one or more post portions 366 are rotatably supported relative to the base portion 360 by the rotator portion 368. The one or more post portions 366 can be moved upwardly and downwardly via rotation of the rotator 368 between an undeployed position (FIG. 26) and a deployed position (FIG. 27), and the wall portion 362 can include an indentation (not shown) for receiving the housing 290 of the first actuator 252. Depending on the orientation of the surgical table 10', either the first sidewall 282 or the second sidewall 284 of the collar portion 270 can be contacted to the wall portion 362. After the collar portion 270 is positioned relative to the slider portion 352, the rotator portion 368 can be rotated by the locking portion 364 using an actuator (not shown) including a motor and transmission (not shown) to move the one or more post portions 366 from the undeployed position to the deployed position to be engaged to and retain the collar portion 270 in position relative to the slider portion 352. While operation of the locking portion 364 is automated using the motor and transmission, the present disclosure is not limited thereto, and the actuation of the locking portion 364 can be manual. Thereafter, the slider portion 352 can be moved outwardly and inwardly relative to the shoulder portion 256 by a third actuator 370 positioned, for example, between the shoulder portion 256 and the wall portion 362. Such inward and outward movement, as depicted in FIGS. 26 and 27, can be used to move the patient P supported by the surgical table 10' in directions transverse to the above-discussed cranial-caudal directions relative to the surgical robotic system R.

A surgical gantry of the present disclosure is generally indicated by the numeral 400 in FIGS. 28, 29, 32-34, 36, and 37. The surgical gantry 400 can be provided in a operating room on a floor thereof. As discussed below, the surgical gantry 400 can incorporate multiple surgical robotic arms SA supported thereby and/or integrated therewith, and a surgical table 10" (FIGS. 36 and 37) or the surgical table 10" can be moveably interconnected with the gantry 400. The surgical table 10" can include features similar to the surgical table 10' to facilitate interconnection with the gantry 400.

The moveable interconnection between the surgical tables 10'/10" and the gantry 400 allows the surgical table 10'/10" and a patient P supported thereby to be positioned and repositioned relative to the gantry 400 (and the multiple surgical robotic arms SA supported by the gantry 400) before, during, and after surgery. Furthermore, the surgical robotic arms SA can be used as part of a surgical robotic system to aid and/or perform surgery on the patient P using surgical equipment such as tools and/or attachments manipulated thereby, and can be manipulated relative to the patient P supported by the surgical table 10'/10" before, during, and after the positioning and repositioning of the surgical table 10'/10" and the patient supported thereby. As such, the positioning and repositioning of the surgical table 10'/10" relative to the surgical robotic arms SA and the manipulation of the surgical robotic arms SA themselves can used in conjunction to aid and/or perform surgery on the patient P supported by the surgical table 10'/10".

Figure 36:
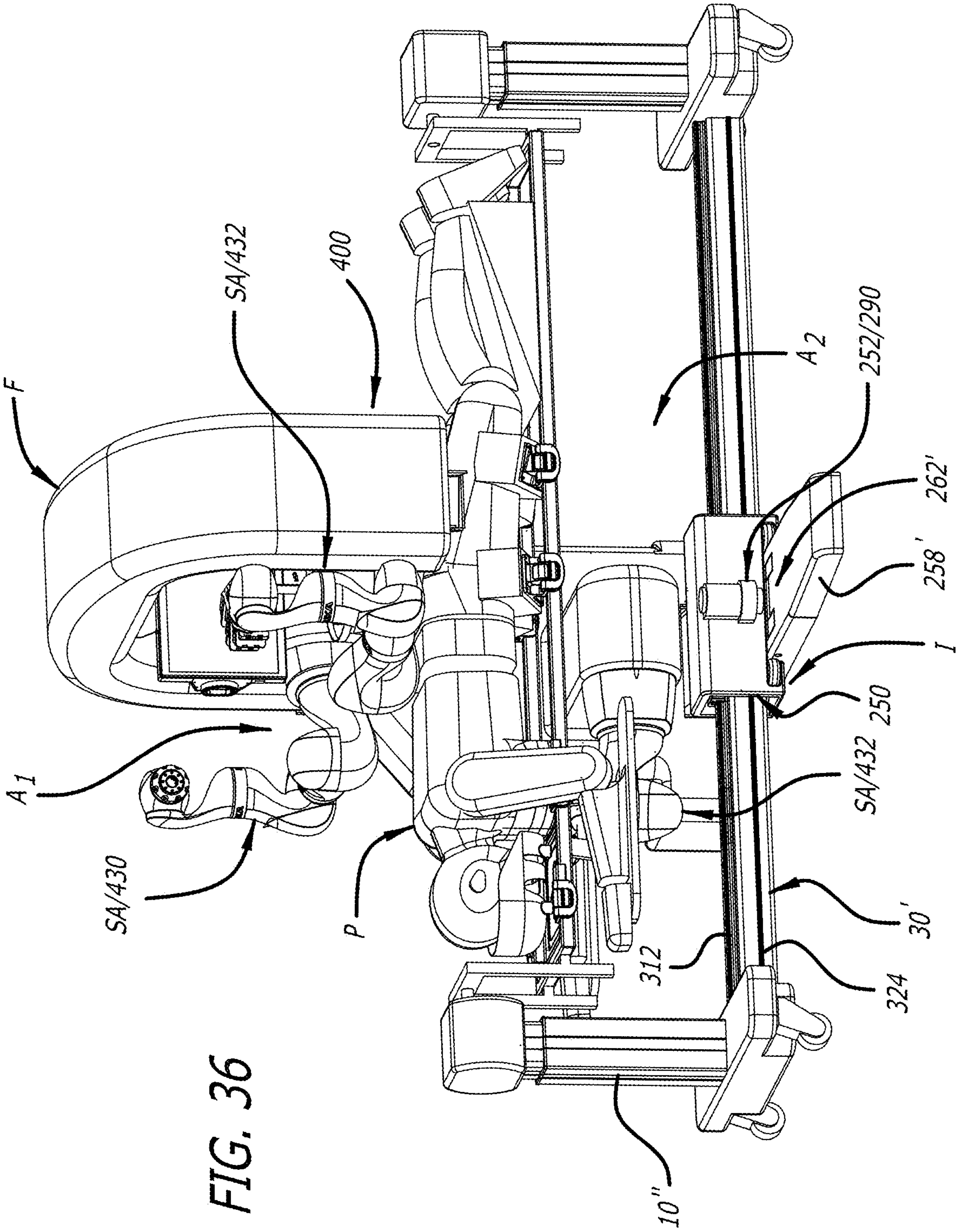
FIG. 36 is a side, perspective view of the surgical gantry of FIG. 28 with a surgical table interconnected therewith via engagement of portions of the interface incorporated on the surgical gantry and the surgical table with the surgical table and a patient supported thereby in a first position relative to the surgical gantry.
Figure 37:
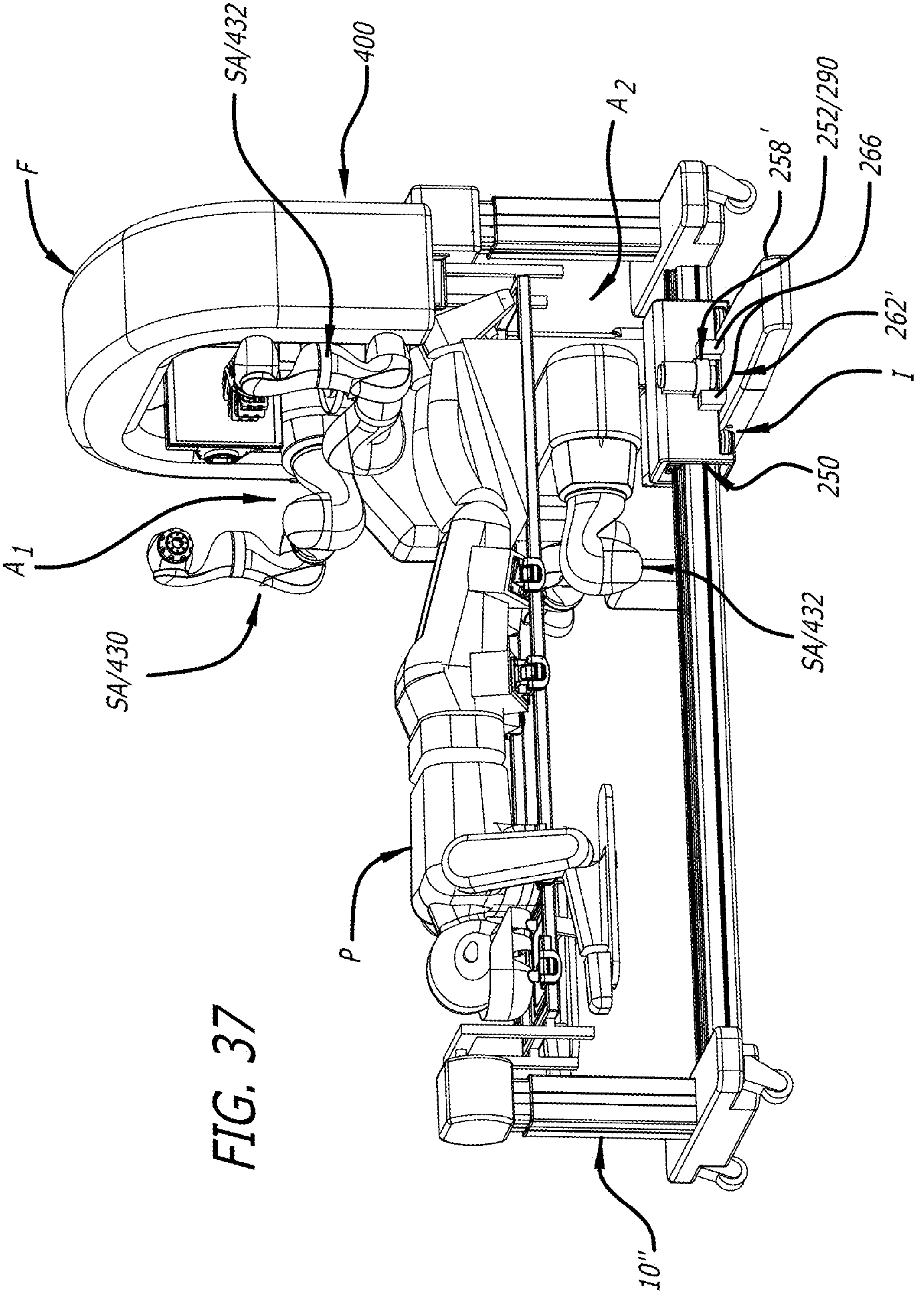
FIG. 37 is a side, perspective view of the surgical gantry of FIG. 28 and the surgical table of FIG. 36 interconnected therewith with the surgical table and the patient supported thereby in a second position relative to the surgical gantry.

To provide the moveable interconnection of the surgical table 10'/10" with the gantry 400, portions of the interface I can be incorporated on or relative to portions of the gantry 400 and on the surgical table 10'/10". The portions of the interface I incorporated on the gantry 400, like similar portions incorporated on the gantry Y, can facilitate the moveable interconnection with the portions of the interface I incorporated on the surgical table 10'/10". During use, the portions of the interface I incorporated on the surgical table 10'/10" can be positioned relative to and then docked with portions of interface I incorporated on or relative to the gantry 400. The use of the interface I, as depicted in FIGS. 36 and 37, allows the surgical table 10'/10" to be docked to the gantry 400 from either lateral side thereof, and such side-loading of the surgical table 10'/10" affords initial placement of portions of the patient P in close proximity to the surgical robotic arms SA. The docking of the surgical table 10'/10" then moveably interconnects to the surgical table 10'/10" relative to the gantry 400. Thereafter, actuation of the interface I affords positioning and repositioning (FIGS. 36 and 37) of the surgical table 10" (or the surgical table 10') and the patient P supported thereby in a cranial-caudal direction relative to the gantry 400 and the surgical robotic arms SA. As such, using the interface I of the gantry 400 and the surgical table 10'/10", the patient P can be positioned and repositioned before, during, and after surgery relative to the surgical robotic arms SA so that the surgical robotic arms SA can aid and/or perform surgery on the patient P. And the surgical arms SA can be manipulated before, during, and after positioning and repositioning of the surgical table 10'/10" and the patient P supported thereby. Accordingly, an operational area of the surgical robotic arms SA is correspondingly increased via using of the interface I and the movement of the surgical table 10'/10" relative to the gantry 400 afforded thereby. Thus, in similar fashion to use of the gantry Y, the surgical robotic arms SA can reach significant portions of the bony anatomy of the patient P using the interface I, the surgical table 10'/10", and the gantry 400.

The gantry 400, as depicted in FIGS. 28, 29, and 32-34, includes a frame F including a base portion 402, an intermediate portion 404, and a support portion 406. The base portion 402 of the frame F can be mounted relative to an operating-room floor (not shown), the intermediate portion 404 of the frame F can be supported by the base portion 402, and the support portion 406 of the frame F can have an inverted U-shape and can be supported by the intermediate portion 404. As such, the base portion 402 and the intermediate portion 404 spaces the support portion 406 from the operating-room floor. As discussed below, the portions of the interface I are provided on or relative to portions of the base portion 402, and the intermediate portion 404 and the support portion 406 can support the surgical robotic arms SA.

Figure 30:
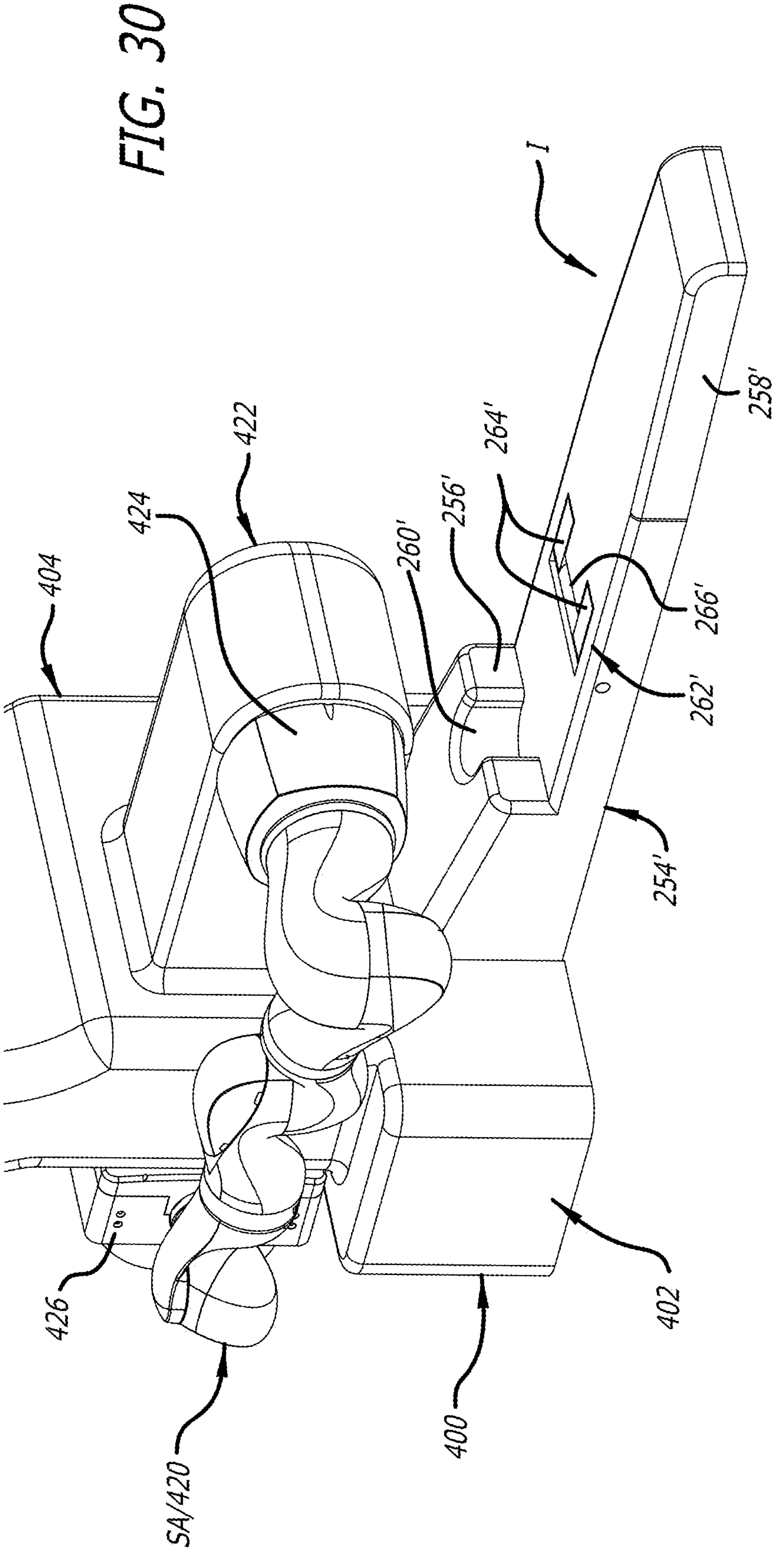
FIG. 30 is an enlarged, side, perspective view of a portion of the surgical gantry of FIG. 28 depicting a portion of the interface incorporated thereon with portions thereof in a disengaged position.
Figure 31:
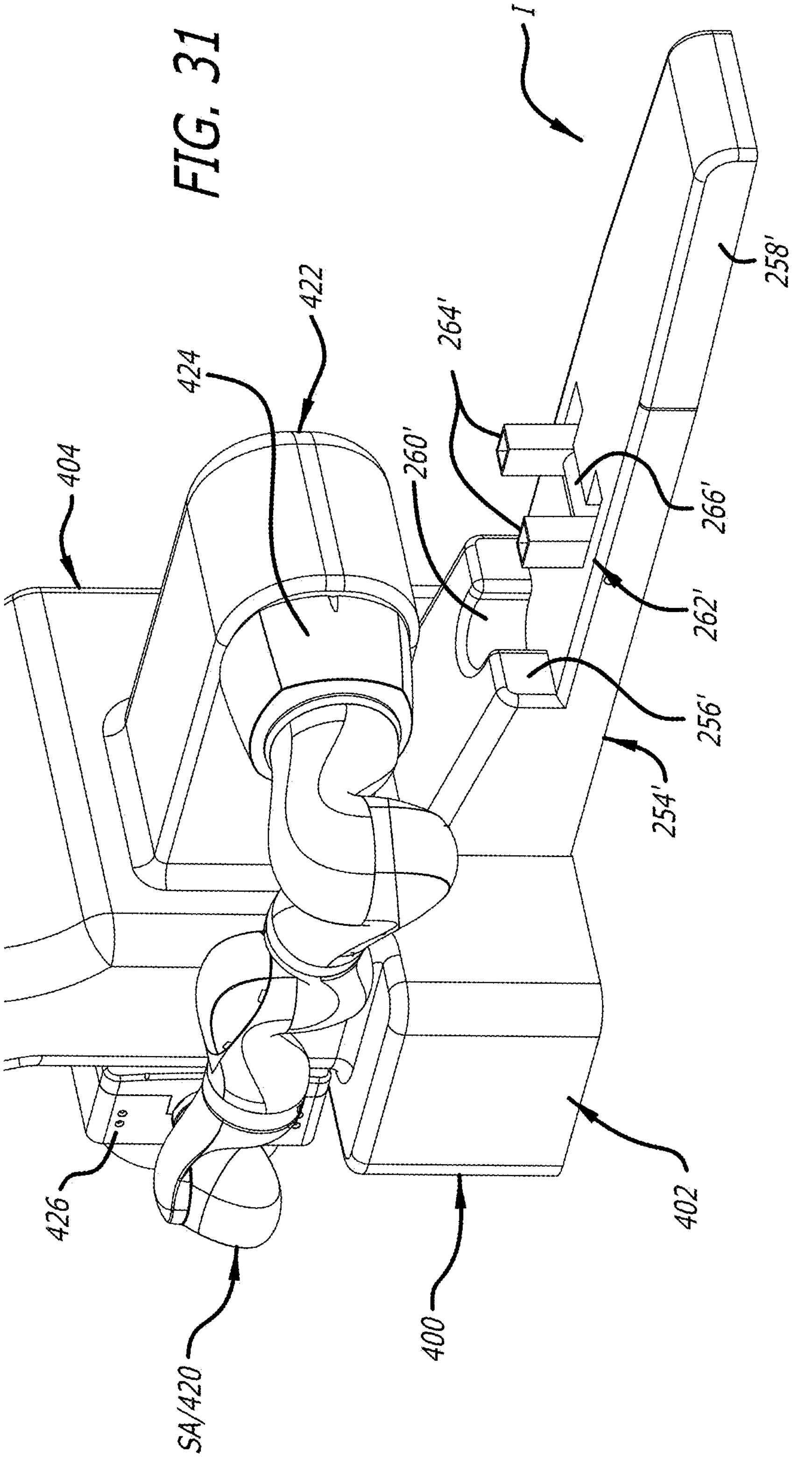
FIG. 31 is an enlarged, side, perspective view of a portion of the surgical gantry of FIG. 28 depicting the portion of the interface incorporated thereon with the portions thereof in an engaged position.

As depicted in FIGS. 30 and 31, the portions of the interface I incorporated on or relative to the frame F of the gantry 400 can be similar to those portions incorporated on or relative to the gantry Y. As such, similar element numbering is used to describe portions of the interface I incorporated on or relative to the frame F of the gantry 400. The interface I incorporated into the gantry 400 includes a second portion 254' incorporated on or relative to the gantry 400. The second portion 254' can be attached to and/or supported relative to the gantry 400, and can include a shoulder portion 256' and an outrigger portion 258'. As depicted in FIGS. 30 and 31, the shoulder portion 256' can be attached to the gantry 400, and the outrigger portion 258' can extend outwardly from the shoulder portion 256'. As discussed below, portions of the shoulder portion 256' can abut portions of the first portion 250 of the interface I, and portions of the first portion 250 of the interface I can be docked to the outrigger portion 258' to facilitate interconnection of the surgical table 10'/10" and the gantry 400. And the shoulder portion 256' can include an indentation 260' for receiving a portion of the first portion 250 of the interface I attached to the surgical table 10'/10".

Additionally, as depicted in FIGS. 30 and 31, the second portion 254' of the interface I can include a locking portion 262' serving to retain the portions of the first portion 250 of the interface I provided on the surgical table 10'/10" in position relative the second portion 254'. The locking portion 262' can incorporate all or portions of the shoulder portion 256', and can include an engagement portion in the form of one or more post portions 264' and a rotator 266' included in the outrigger portion 258', and the one or more post portions 264' are moveable upwardly and downwardly via rotation of the rotator 266' between an undeployed position (FIGS. 30 and 36) and a deployed position (FIGS.

31 and 37). As discussed below, when in the undeployed position, the post portions 264' are retracted into the outrigger portion 258' to afford passage of the first portion 250 attached to the surgical table 10'/10", and when in the deployed position, the one of more post portions 264' are engaged to and retain the first portion 250 attached to the surgical table 10'/10" in position relative to the gantry 400. The locking portion 262' can include an actuator (not shown) including a motor and a transmission (not shown) for driving movement of the post portions 264'. While operation of the locking portion 262' is automated using the motor and transmission, the present disclosure is not limited thereto, and the actuation of the locking portion 262' can be manual.

When positioning the surgical table 10'/10" relative to the gantry 400, as depicted in FIGS. 36 and 37, the outrigger portion 258' can be inserted into the outrigger-receiving area 306, and the wheels 292 can be used guide movement (via contact of the wheels 292 with sidewalls of the outrigger portion 258') of the collar portion 270 of the first portion 250 of the interface I. Such guidance affords movement of the collar portion 270 (and the surgical table 10'/10" attached thereto) into position so that either the first sidewall 282 (corresponding to a first orientation (FIGS. 36 and 37) of the surgical table 10'/10" relative to the gantry 400) or the second sidewall 284 (corresponding to an opposite second orientation) of the surgical table 10'/10" relative to the gantry 400) contacts the shoulder portion 256' of the second portion 254' of the interface I. If the first sidewall 282 is contacted to the shoulder portion 256', the housing 290 of the first actuator 252 is opposite from the indentation 260', and if the second the second sidewall 284 is contacted to the shoulder portion 256', the housing 290 of the first actuator 252 is received in the indentation 260'.

After either the first sidewall 282 or the second sidewall 284 is contacted to the shoulder portion 256', the locking portion 262' can be actuated to move the post portions 264' from the undeployed position (FIGS. 30 and 36) to the deployed position (FIGS. 31 and 37). When the first sidewall 282 is contacted to the shoulder portion 256' and the housing 290 of the first actuator 252 is opposite from the indentation 260', the post portions 264' contact the second sidewall 284 and side portions of the housing 290 in the deployed position. And when the second sidewall 284 is contacted to the shoulder portion 256' and the housing 290 of the first actuator 252 is received in the indentation 260', the post portions 264' contact the first sidewall 282. Use of the post portions 264' in contacting the first sidewall 282 and the second sidewall 284, the contact of the post portions 264' with the side portions of the housing 290, and the receipt of the housing 290 in the indentation 260', serve in maintaining the position of the first portion 250 of the interface I (including the collar portion 270) relative to the second portion 254' of the interface I (including the shoulder portion 256' and the outrigger portion 258') and the gantry 400.

The circular gear driven by the first actuator 252 can be engaged to the linear gear 324, and rotation of the circular gear via actuation of the first actuator 252 serves to move the cross member 30' relative to the collar portion 270. For example, rotation of the circular gear in a first rotational direction can move the cross member 30' in a first linear direction relative to the collar portion 270, and rotation of the circular gear in an opposite rotational direction can move the cross member 30' in an opposite second linear direction relative to the collar portion 270. As such, rotation of the circular gear (via actuation of the actuator 252) serves in adjusting the position of the surgical table 10'/10" relative to the gantry 400 and the surgical robotic arms SA, as well as affording positioning and repositioning the patient P supported by the surgical table 10'/10" in cranial-caudal directions relative to the surgical robotic arms SA. A first position of the surgical table 10'/10" is depicted in FIG. 36, and a second position of the surgical table 10'/10" is depicted in FIG. 37. Thus, such adjustment allows the patient P to be positioned and repositioned before, during, and after surgery relative to the surgical robotic arms SA, so that the surgical robotic arms SA can perform and/or aid the performance of surgery on the patient P.

Figure 35:
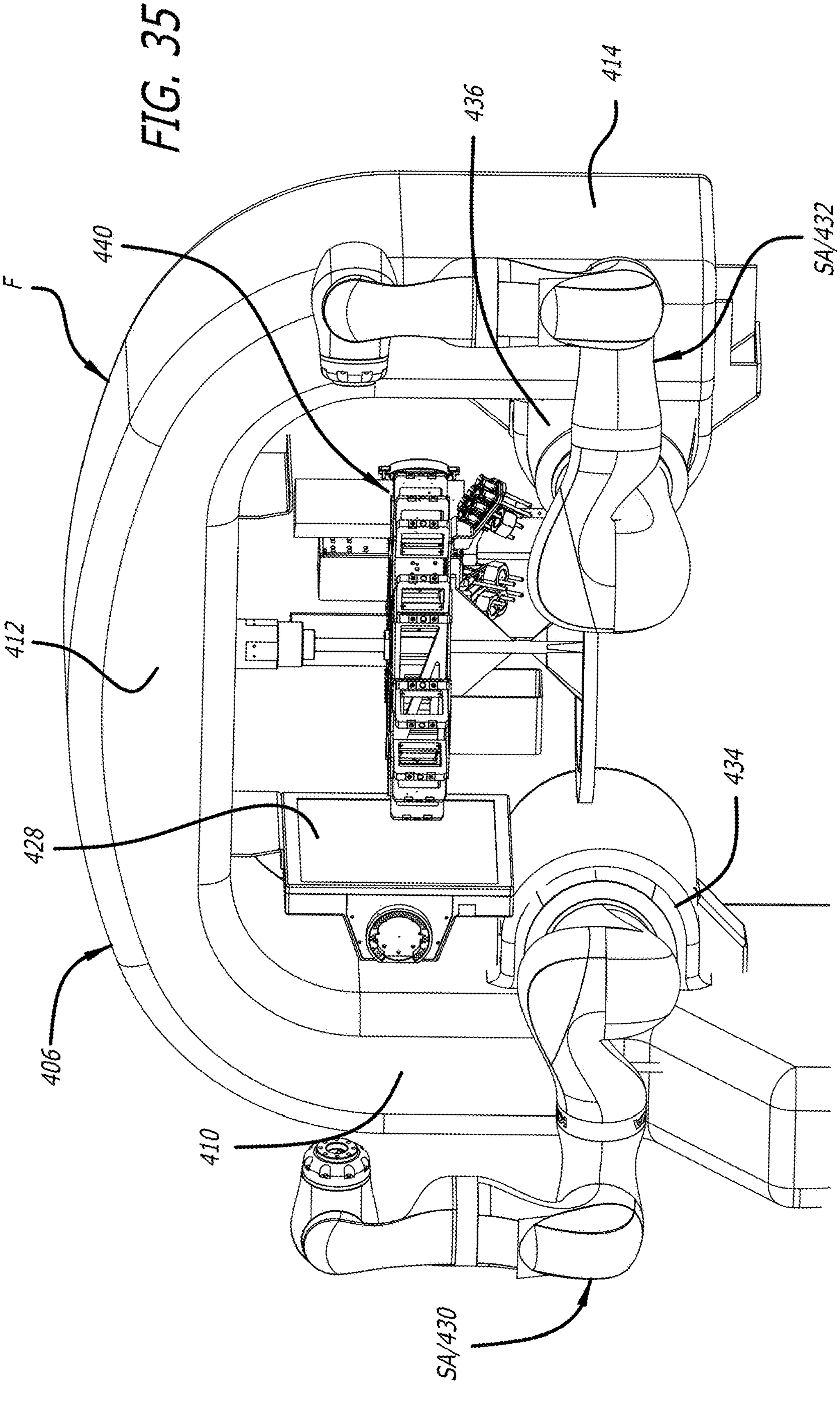
FIG. 35 is an enlarged, front, perspective view of an upper portion of the surgical gantry of FIG. 28 that is configured to extend above and over portions of a surgical table and a patient supported by the surgical table.

The support portion 406 of the frame F of the gantry 400, as depicted in FIG. 35, includes a first portion 410, a second portion 412, and a third portion 414. The first portion 410 is supported by and attached to the intermediate portion 404, the second portion 412 is supported by and attached to the first portion 410, and the third portion 414 is supported by and attached to the second portion 412. As such, the second portion 412 bridges the first portion 410 and the third portion 414, and the first portion 410 and the third portion 414 are opposed to one another on. When the surgical table 10'/10" is moveably interconnected with the frame F of the surgical gantry 400, the first portion 410, the second portion 412, and the third portion 414 can define an area $A_1$ above (FIGS. 36 and 37) the patient P supported by the surgical table 10'/10" in which one of more of the surgical robotic arms SA can be operated.

Figure 28:
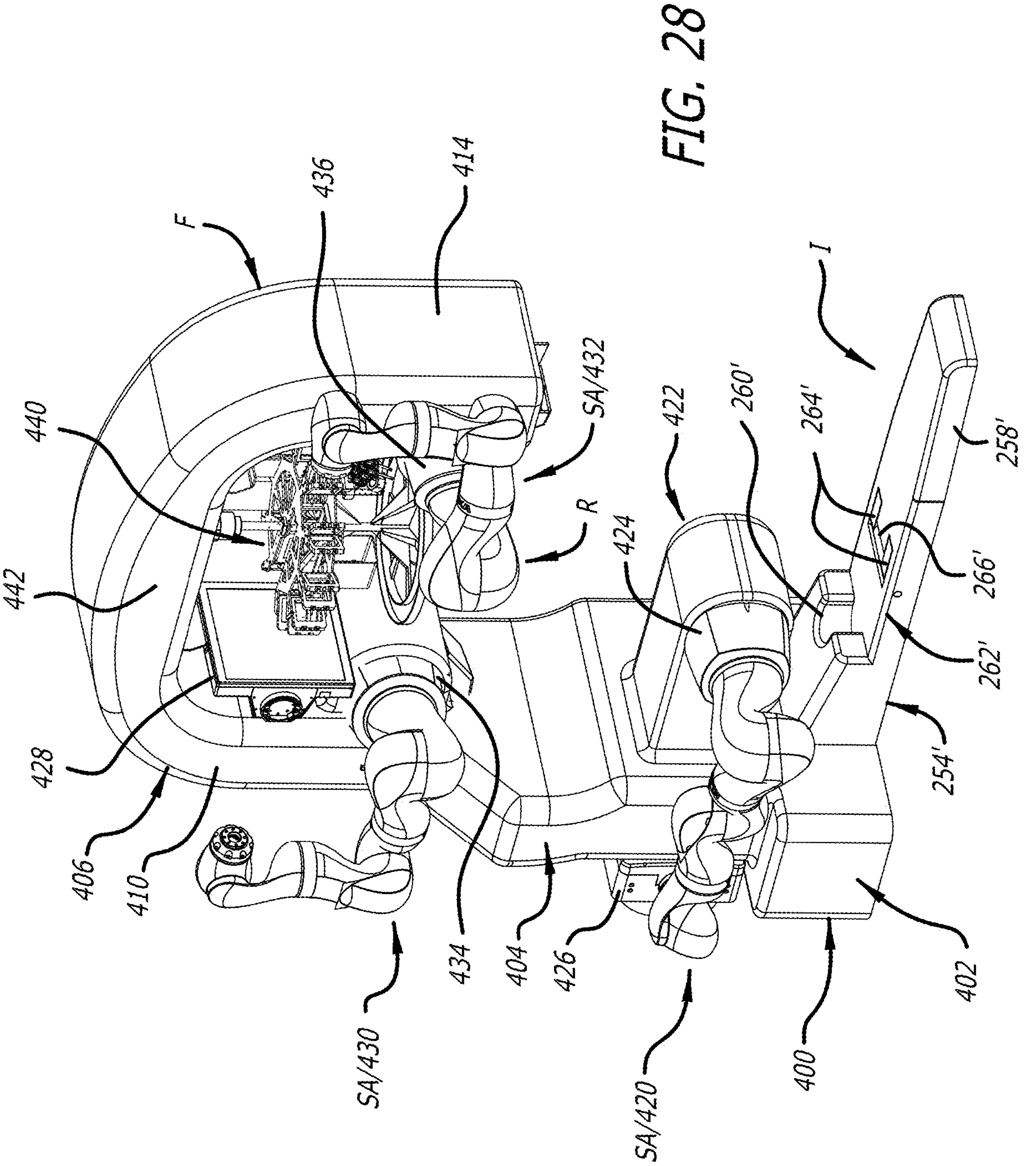
FIG. 28 is first side, perspective view that illustrates a surgical gantry incorporating three surgical robotic arms and portions of an interface facilitating attachment of a surgical table relative thereto.

Similarly, when the surgical table 10'/10" is moveably interconnected with the frame F of the surgical gantry 400, a second area $A_2$ can be defined above an extension portion 422 and below (FIGS. 36 and 37) the patient supported by the surgical table 10'/10" in which one or more of the surgical robotic arms SA can be operated. As depicted in FIGS. 28, 30, and 31, a first surgical arm 420 of the surgical arms SA is supported relative to the intermediate portion 404 of the frame F by the extension portion 422 and a mounting portion 424 attached to the extension portion. The first surgical arm 420 can include one or more actuators and one or more arm portions actuatable by the one or more actuators to facilitate manipulation thereof. As depicted in FIGS. 28 and 30-34, the extension portion 422 can extend outwardly from the intermediate portion 404 over portions of the second portion 254' of the interface I, and the mounting portion 424 can extend outwardly from an end portion of the extension portion 422. When the surgical table 10'/10" is moveably interconnected with the gantry 400, the positions of the extension portion 422 and the mounting portion 424, and the support of the first surgical arm 420 thereby affords access of the first surgical arm 420 to the area $A_2$ between the extension portion 422 and the patient P supported by the surgical table 10'/10".

Figure 29:
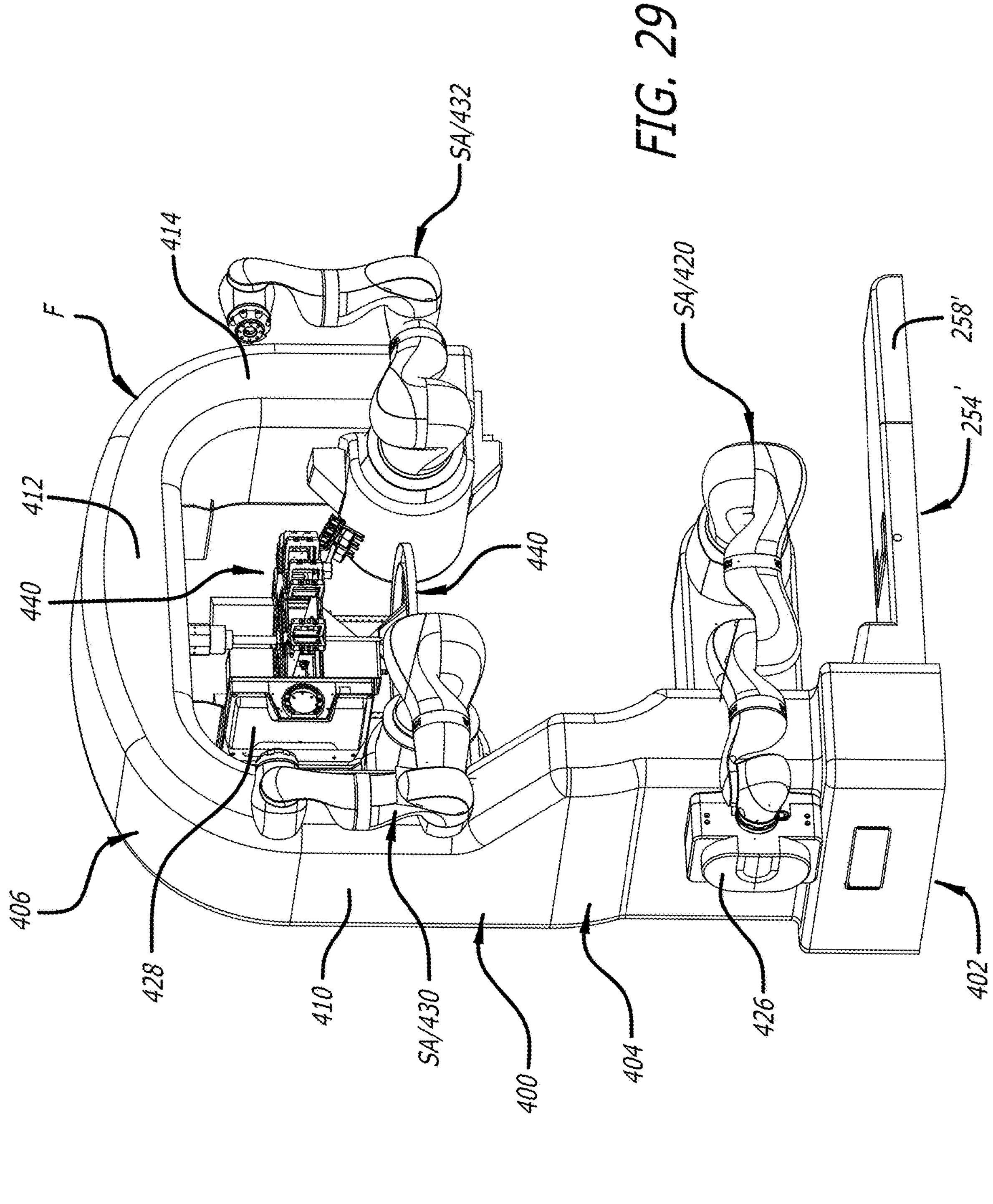
FIG. 29 is a second side, perspective view that illustrates the surgical gantry of FIG. 28.

The first surgical arm 420 can be used in moving the attachments/tools supported thereby into and out of the area $A_2$ before, during, and after articulation and rotation of the patient P via use of the surgical table 10'/10". For example, a radiographic projector (or emitter) 426 or other surgical attachments/tools can be supported by an end portion the first surgical arm 420, and the radiographic projector 426 or the other surgical attachments/tools can be moved into and out of the area $A_2$ by the first surgical arm 420. As discussed below, the radiographic projector 426 can be used for directing electromagnetic radiation toward the patient P, and such electromagnetic radiation can penetrate through the patient P and ultimately be received at one or more image receptors 428 supported by others of the surgical robotic arms SA. The radiographic projector 426 can be attached and detached from the first surgical arm 420, and, when detached, the radiographic projector 426 can be stored on a portion of the gantry 400 (FIG. 29). The other attachments/tools can be attached and detached from the end portion of the first surgical arm 420 to aid and/or perform surgery on the patient P. For example, a patient-contacting support portion (not shown) can be attached to the first surgical arm 420, and via manipulation of the first surgical arm 420, the patient-contacting support portion can be contacted to the patient P to support portions of the patient P before, during, and after articulation and rotation of the patient P via use of the surgical table 10'/10".

A second surgical arm 430 and a third surgical arm 432 of the surgical arms SA can be supported relative to the support portion 406 of the frame F. Like the first surgical arm 420, each of the second surgical arm 430 and the third surgical arm 432 can include one or more actuators and one or more arm portions actuatable by the one or more actuators to facilitate manipulation thereof. The second surgical arm 430 can be attached relative to the first portion 410 using a mounting portion 434, and the third surgical arm 432 can be attached relative to the third portion 414 using a mounting portion 436. When the surgical table 10'/10" is moveably interconnected with the gantry, the positions of the mounting portions 434 and 436 and the support of the second surgical arm 430 and the third surgical arm 432 thereby affords access of the second surgical arm 430 and the third surgical arm 432 to the area $A_1$ above the patient P. The attachments/tools can be attached and detached from end portions of the second surgical arm 430 and the third surgical arm 432 to aid and/or perform surgery on the patient P. In doing so, the second surgical arm 430 and the third surgical arm 432 can be used in moving the attachments/tools supported thereby into and out of the area $A_1$ before, during, and after articulation and rotation of the patient P via use of the surgical table 10'/10". Furthermore, the mounting portions 434 and 436 can be moveably attached to the first portion 410 and the third portion 414. For example, the mounting portions 434 and 436 can be pivotally attached to first portion 410 and the third portion 414 to afford swiveling of the second surgical arm 430 and the third surgical arm 432 into and out of the area $A_1$.

As depicted in FIGS. 28, 29, and 32-25 rack portion 440 can be supported by the second portion 412 of the support portion 406 of the frame F. The rack portion 440 can be rotatably attached relative to the second portion 412, and the rack portion 440 can include an actuator facilitating such rotation. The rack portion 440 can be used to store and support attachments/tools attachable to and detachable from the second surgical arm 430 and/or the third surgical arm 432. To illustrate, the rack portion 440 can support attachments/tools affording radiography, nerve retraction, tissue retraction, drilling, taping, screw placement, hard and soft tissue cutting, disc preparations, disc sizing, device implantation, etc. During use, the rack portion 440 can be rotated into position relative to the second surgical arm 420 and/or the third surgical arm 420 so that the arms can be manipulated to attach the desired attachment thereto. The rack portion 440, for example, can be rotated to position a hard and soft tissue cutting attachment relative to the second surgical arm 430, and the hard and soft tissue cutting attachment then can be attached to the second surgical arm 430; and the rack portion 440 can be rotated to position a retraction attachment relative to the third surgical arm 432 and the retraction attachment then can be attached to the third surgical arm 432. Additionally, the rack portion 440 can be used to store and support one or more of the image receptors 428, and the rack portion 440 can be rotated to position the one or more image receptors 428 relative to and for attachment to the second surgical arm 430 and the third surgical arm 432, The image receptors 428 also can be stored and supported elsewhere on the frame F (FIGS. 28 and 29).

Figure 32:
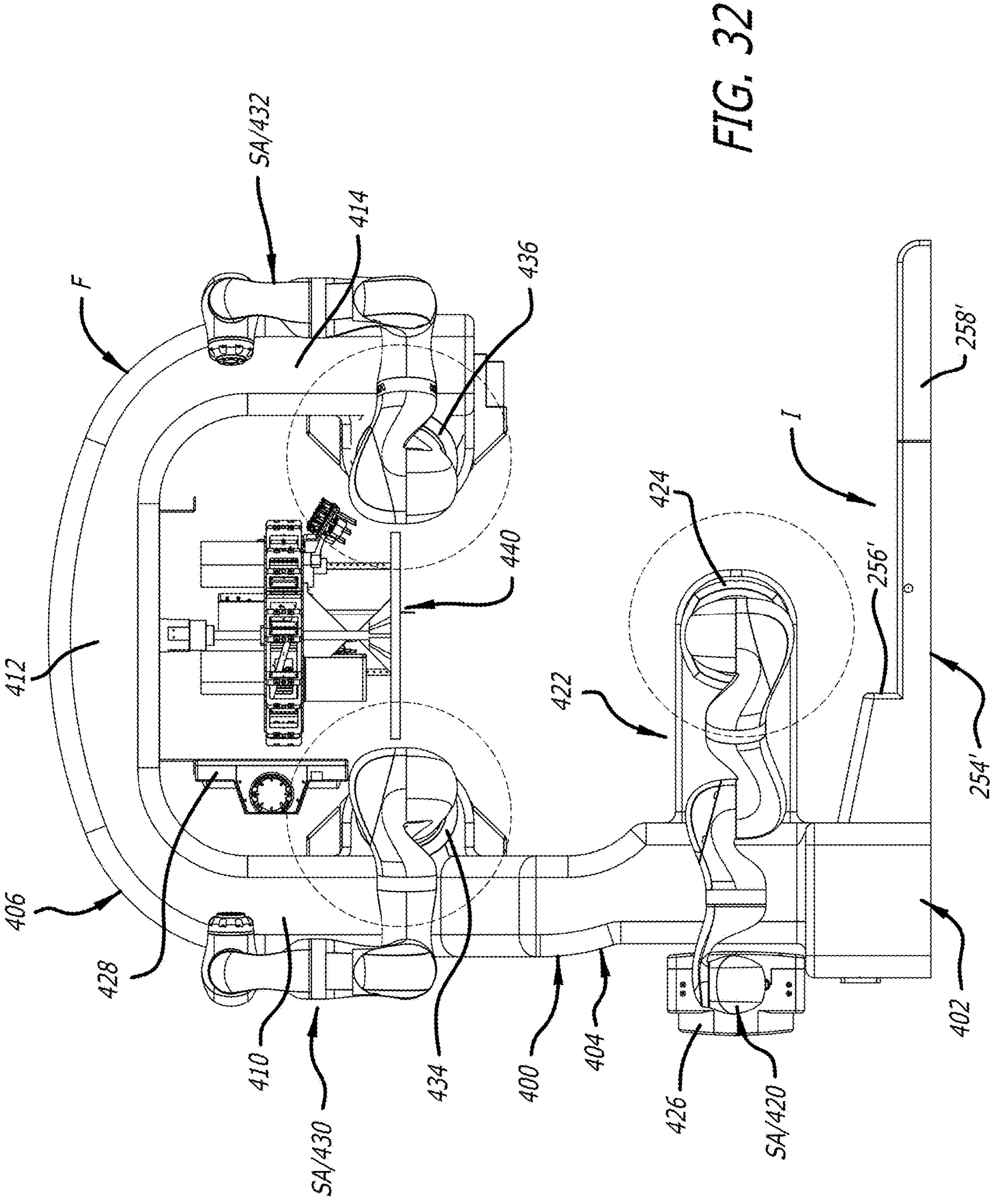
FIG. 32 is a front, elevational view of the surgical gantry of FIG. 28 including the three surgical arms depicting potential rotational movement of each of the three surgical robotic arms on the surgical gantry.

With the attachments/tools attached to the end portions thereof, the first surgical arm 420, the second surgical arm 430, and/or the third surgical arm 432 can be moved independently or coordinatedly in simultaneous or non-simultaneous fashion relative to the patient P to aid and/or perform surgery on the patient P. As discussed above, the first surgical arm 420, the second surgical arm 430, and the third surgical arm 432 can be moved relative to the patient P before, during, and after articulation and rotation of the patient P by the surgical table 10'/10". As depicted in FIG. 32, the first surgical arm 420, the second surgical arm 430, and the third surgical arm 432 can be rotated (as denoted by dashed circles) about the mounting portions 424, 434, and 436, respectively, independently and/or coordinately in simultaneous or non-simultaneous fashion. The remaining portions of the first surgical arm 420, the second surgical arm 430, and the third surgical arm 432 can also be moved independently and/or coordinatedly in simultaneous or non-simultaneous fashion.

Figure 33:
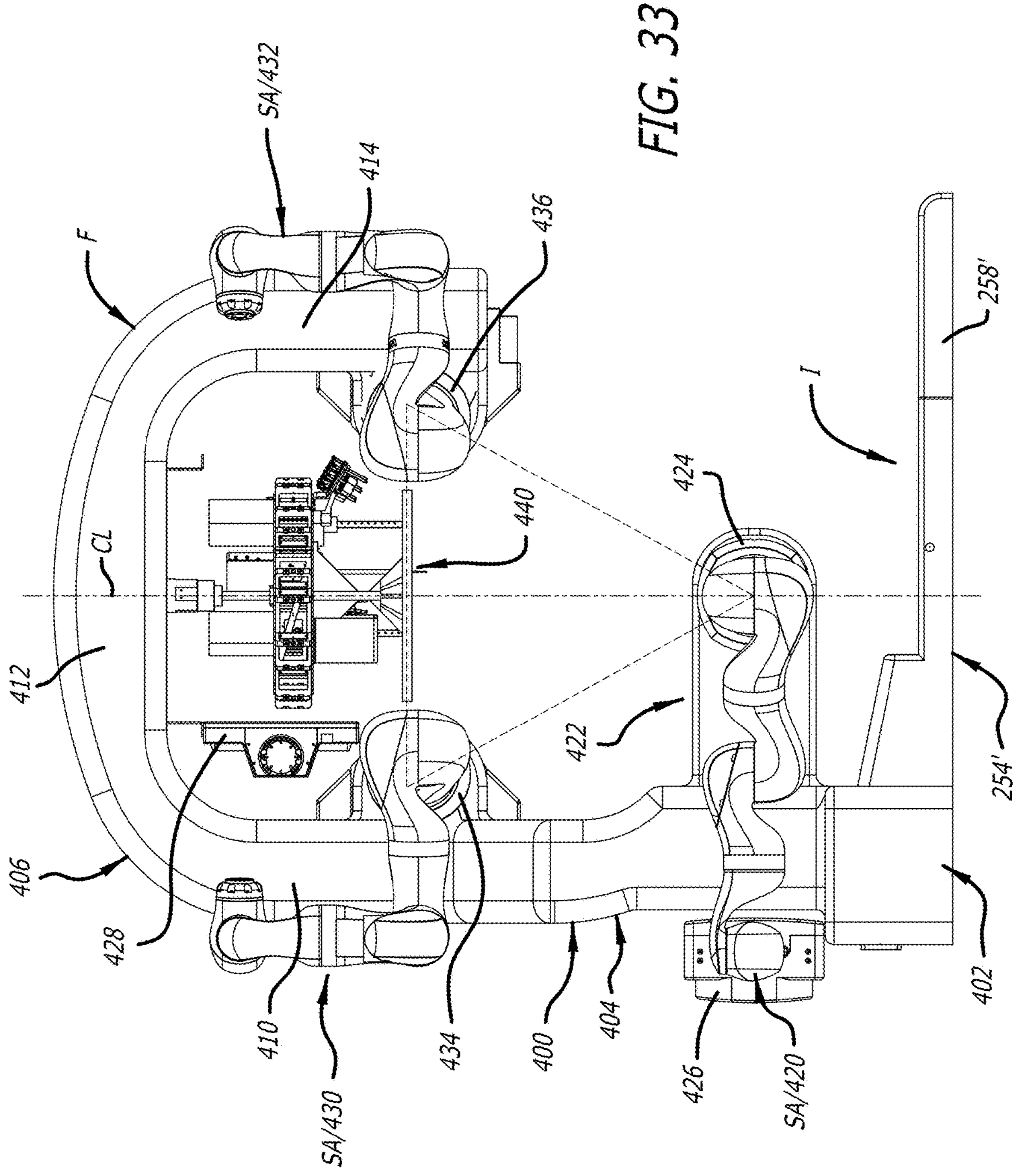
FIG. 33 is a front, elevational view of the surgical gantry of FIG. 28 including the three surgical robotic arms depicting a potential area of access afforded using the three surgical arms.
Figure 34:
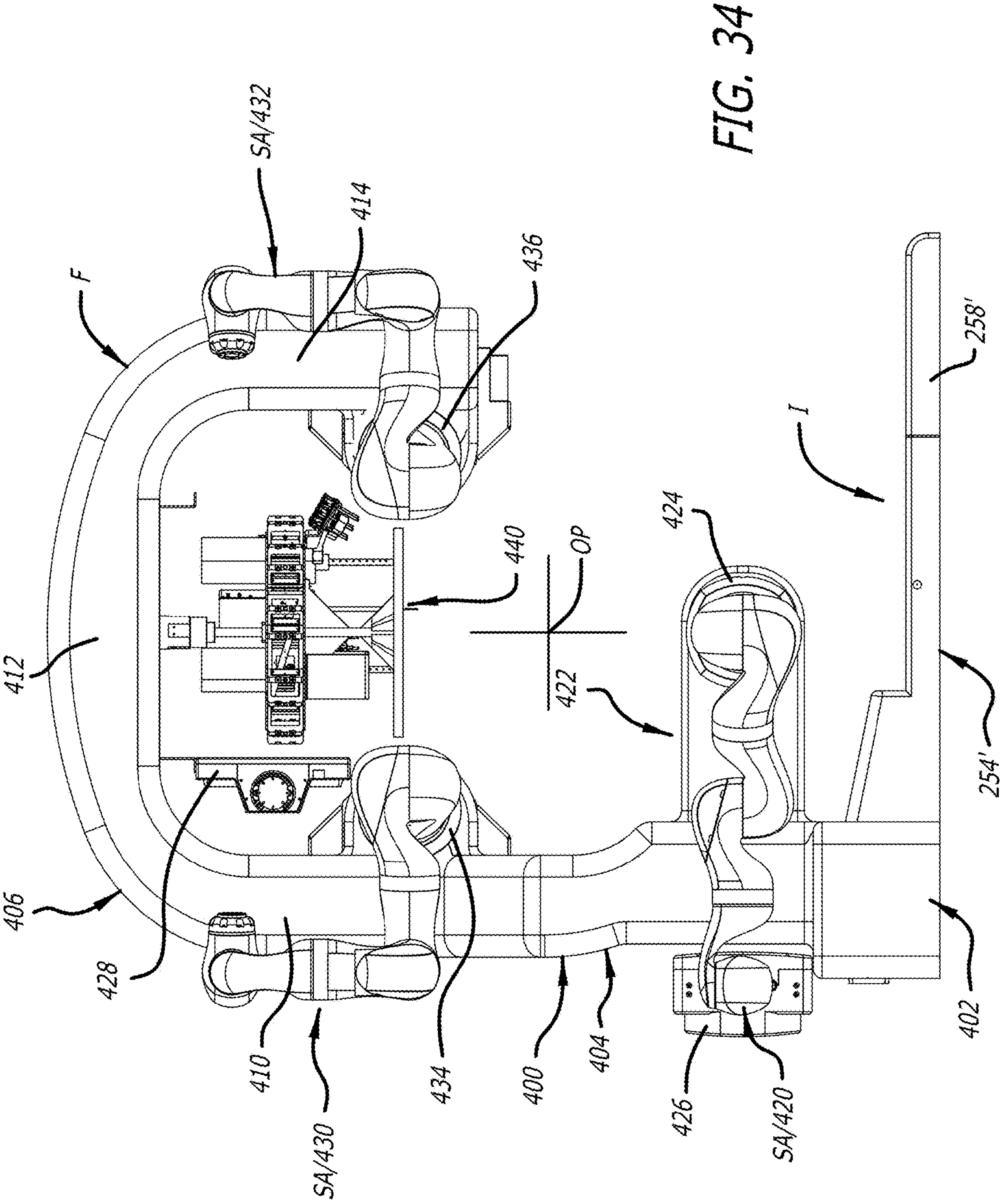
FIG. 34 is a front, elevational view of the surgical gantry of FIG. 28 including the three surgical robotic arms depicting an origin from which the three surgical robotic arms can be articulated thereabout.

As depicted in FIG. 33, the first surgical arm 420 is positioned along a centerline CL, and the second surgical arm 430 and the third surgical arm 432 are positioned on opposite sides of the centerline CL. During manipulation thereof, the end portions of the first surgical arm 420, the second surgical arm 430, and the third surgical arm 432, and the attachments/tools supported thereby can be moved within at least a first two-dimensional plane denoted by a dashed triangle depicted in FIG. 33 about an origin point OP denoted in FIG. 34. Typically, the manipulation of the first surgical arm 420, the second surgical arm 430, and the third surgical arm 432 will be versatile enough during manipulation to move the end portions thereof side-to-side into and out of the first plane in additional second two-dimensional planes parallel to the first plane. The first and second two-dimensional planes can define a three-dimensional operational area in which the attachments/tools can be moved by the first surgical arm 420, the second surgical arm 430, and the third surgical arm 432.

When the surgical table 10'/10" is moveably interconnected with the gantry 400, the first and second two-dimensional planes extend transversely to a cranial-caudal axis of the patient P supported by the surgical table 10'/10", and the three-dimensional operational area (formed by the first and second two-dimensional planes) will overlap with portions of the areas $A_1$ and $A_2$. Portions of the patient P can be articulated and rotated by the surgical tables 10'/10" to be at or adjacent the origin point OP to afford access by the attachments/tools supported thereby to these portions of the patient P and/or position the attachment/tools opposite from one another across the origin point OP or across areas adjacent the origin point OP. When the patient P is moved via positioning and repositioning of the surgical table 10'/10" relative to the gantry 400 using the interface I, the three-dimensional operational area of the first surgical arm 420, the second surgical arm 430, and the third surgical arm 432 can be correspondingly increased by such movement. Thus, positioning and repositioning of the patient P using the interface I in the cranial-caudal directions correspondingly increases access to the patient P by the attachments/tools attached to the first surgical arm 420, the second surgical arm 430, and/or the third surgical arm 432.

To illustrate, the second surgical arm 430 with the cutting attachment attached thereto, and the third surgical arm 432 with the retraction attachment attached thereto can be manipulated to access the same or different portions of the patient P. And the use of the interface I to position and reposition the patient P relative to the second surgical arm 430 and the third surgical arm 432 increases the three-dimensional operational area of the cutting attachment and the retraction attachment over that afforded by use of the second surgical arm 430 and the second surgical arm 432 alone. Similarly, the radiographic projector 426 when supported by the first surgical arm 420, and the one or more radiographic receptors 428 when supported by the second surgical arm 430 and/or the third surgical arm 432 can be manipulated on opposite from on another across the patient P to facilitate two-dimensional or three-dimensional radiographic imaging of portions of the patient P. And the use of the interface I to position and reposition the patient P relative to the first surgical arm 420, the second surgical arm 430, and/or the third surgical arm 432 increases the three-dimensional operational area of the radiographic projector 436 and the one or more radiographic receptors 428 over that afforded by use of the first surgical arm 420, the second surgical arm 430, and/or the third surgical arm 432 alone.

During use of the surgical gantry 400 and the surgical tables 10'/10", the patient P can be positioned on the surgical tables 10'/10" in a prone position, a supine position, and lateral positions. Thereafter, the patient P can be articulated and rotated using the surgical tables 10'/10", and the tables 10'/10" can be moveably interconnected relative to the gantry 400 using the interface I. As depicted in FIGS. 36 and 37, the patient P is supported by the surgical table 10" in the prone position, and the surgical table 10" is moveably interconnected with the surgical gantry 400 using the interface I. As discussed above, the actuation of the interface I affords positioning and repositioning (FIGS. 36 and 37) of the surgical table 10" (or the surgical table 10') and the patient P supported thereby in the cranial-caudal directions relative to the gantry 400 and the surgical robotic arms SA through the above-discussed three-dimensional operational area. As such, the patient P can be positioned and repositioned using the relative movement of the surgical table 10'/10" before, during, and after manipulation of the first surgical arm 420, the second surgical arm 430, and the third surgical arm 432 (and the attachments/tools attached thereto) to afford use of the surgical robotic arms SA at different locations on the patient P and increase the corresponding three-dimensional operational areas afforded thereby.

The surgical table 10'/10" and the surgical gantry 400 can include a controller or controllers for controlling actuatable features thereof. To illustrate, when using the surgical table 10', the controller or controllers included therein can control the operation of the slider portion 40 and the actuator 80 thereof; the operation of the rotator portion 42 and the actuator 94 thereof; the operation of the slider portion 100 and the actuator 132 thereof; the operation of the telescoping columns 140; the operation of the motors and transmissions 156 of the rotational portions 154; and the operation of the motors and transmissions 162 of the tilt portions 160. And, when using the surgical table 10", the operation of similar actuatable features thereof can be controlled using a controller or controllers included therein.

During use, the controller or controllers, in addition to controlling the actuatable features of the surgical table 10'/10", can control operation of actuatable features including the actuator 252 of the interface I to facilitate movement of the surgical table 10'/10" relative to the frame F of the surgical gantry 400, the actuator of the locking portion 262' to facilitate movement of the rotator 266' of the interface I; the actuators of the surgical robotic arms SA to control manipulation thereof; the actuator of the rack portion 440 to facilitate rotation thereof; and operation of the attachments/tools (including the radiographic projector 426 and the one or more radiographic receptors 428) attachable to and detachable from the surgical robotic arms.

Each or some of the surgical table 10'/10", the surgical gantry 400, and/or components thereof can include at least one controller for controlling operation of the corresponding actuatable features associated therewith. For example, each of the surgical table 10'/10" and the surgical gantry 400 can include a controller or controller, and the controllers can communicate with the above-discussed actuatable features and one another to control and coordinate operation with the above-discussed actuatable features. Or, for example, one or more controllers can be included on a single one or multiple ones of the surgical table 10'/10", the surgical gantry 400, and/or the components thereof, and the controller or controllers can communicate with the above-discussed actuatable features and one another to control and coordinate operation with the above-discussed actuatable features.

As such, the controller or controllers can be used to actuate movement of the actuatable features of the surgical table 10'/10 and the surgical gantry 400 in coordination and concert with one another to synchronize movement therebetween. Such synchronized movement, for example, can allow the surgical table 10'/10" to move relative to the frame F and the surgical arms SA supported thereby, and the surgical arms SA with the attachments/tools attached thereto to be moved independently or coordinatedly in simultaneous or non-simultaneous fashion relative to the patient P to aid and/or perform surgery on the patient P before, during, or after the relative movement of the surgical table 10'/10". The controllers can communicate with one another and the actuatable above-discussed features via hardwired and/or wireless connections.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. A combination of a surgical table, a gantry including surgical robotic arms, and an interface for moveably interconnecting the surgical table with the gantry, the combination comprising: the surgical table comprising a first end, an opposite second end, a first lateral side, an opposite second lateral side, a longitudinal cross-member extending between the first end and the second end, at least one track attached to the longitudinal cross-member, and a patient support portion being configured to support a patient thereon; the gantry comprising: a base portion provided on an operating room floor; a support portion supported relative to the base portion, the support portion having a first portion on a first side of the gantry, and a second portion on a second side of the gantry; and a first surgical robotic arm and a second surgical robotic arm of the surgical robotic arms, the first surgical robotic arm supported by the first portion of the gantry and the second surgical robotic arm supported by the second portion of the gantry, the first surgical robotic arm and the second surgical robotic arm each including a first end portion for supporting surgical equipment thereon; and the interface comprising: a collar portion attached relative to the longitudinal cross-member of the surgical table, the collar portion including a first end, an opposite second end, an interior cavity extending between the first end and the second end, an interior surface defining a portion of the interior cavity, and at least one truck attached relative to the interior surface, portions of the longitudinal cross member being received in the interior cavity, and the at least one truck engaged to the at least one track portion attached to the longitudinal cross member; an actuator portion actuatable to facilitate movement of the at least one truck along the at least one track; and a locking portion attached to and/or supported relative to the gantry, and at least one engagement portion moveable between a disengaged position and an engaged position to maintain a position of the collar portion of the surgical table relative to the gantry; wherein, after the collar portion is maintained in position relative to the gantry by the interface, an actuation of the actuator portion drives movement of portions of cross member into and out of the interior cavity via movement of the at least one truck along the at least one track to correspondingly adjust positions of the surgical table relative to the gantry, and the first surgical robotic arm and the second surgical robotic arm supported by the gantry; wherein, after the collar portion is maintained in position relative to the gantry, the first surgical robotic arm and the second surgical robotic arm are supported by the gantry above the patient supported by the surgical table, the surgical equipment supported by the first surgical robotic arm and the second surgical robotic arm are moveable within at least a first plane transverse to a cranial-caudal axis of the patient supported by the patient support portion of the surgical table, and as the positions of the surgical table are adjusted relative to the gantry via actuation of the actuator portion, portions of the patient supported by the patient support portion are configured to be moved into and out of the first plane to thereby creating a three-dimensional operational area in which the first surgical robotic arm and the second surgical robotic arm are configured to access the patient and/or areas around the patient.

2. The combination of claim 1, wherein, after the collar portion is maintained in position relative to the gantry, the surgical equipment supported by the first surgical robotic arm is positionable relative to one of a first lateral side and a second lateral side of the patient supported in a prone position on the patient support portion, and the surgical equipment supported by the second surgical robotic arm is positionable relative to the other of the first lateral side and the second lateral side of the patient supported in the prone position on the patient support portion.

3. The combination of claim 1, wherein the gantry further comprises an extension portion extending outwardly relative to the base portion, and a third surgical robotic arm of the surgical robotic arms supported by the extension portion, and, after the collar portion is maintained in position relative to the gantry, the third surgical robotic arm is supported by the gantry below the patient supported by the surgical table, and surgical equipment supported third surgical robotic arm is moveable within at least the first plane.

4. The combination of claim 1, wherein the collar portion includes an exterior surface and the gantry includes a shoulder portion, and the exterior surface is contacted to the shoulder portion, when the collar portion is maintained in position relative to the gantry by the interface.

5. The combination of claim 4, wherein, when the collar portion is maintained in position relative to the gantry by the interface, the collar portion is position between the shoulder portion and the least one engagement portion of the locking portion in the engaged position.

6. The combination of claim 1, wherein the actuator portion is one of attached to the collar portion and attached to and/or supported by the gantry, the actuator portion including a first gear portion being configured to operatively engage a second gear portion attached to the cross member.

7. The combination of claim 6, wherein, when the collar portion is maintained in position relative to the gantry by the interface, the first gear portion is a circular gear and the second gear portion is a linear gear, and wherein rotation of the circular gear in a first rotational direction moves the cross member in a first linear direction relative to the collar portion and the gantry, and rotational of the circular gear in an opposite second rotational direction moves the cross member in an opposite second linear direction relative to the collar portion and the gantry.

8. The combination of claim 7, wherein movement of the cross member in the first and second linear directions relative to the collar portion corresponding moves the surgical table in the first and second linear directions relative to the gantry adapted to be stationary to afford positioning and repositioning of the portions of the patient supported by the surgical table into and out of the first plane.

9. The combination of claim 1, wherein the interface includes an outrigger portion attached to and/or supported relative to the gantry, the outrigger portion including a first side surface and a second side surface; and wherein the collar portion includes a receiving area defined in part by one or more bumpers attached to the collar portion on a first side of the receiving area and one or more bumpers attached to the collar portion on a second side of the receiving area, the outrigger portion being receivable in the receiving area, and contact of the one or more bumpers on the first side of the receiving area with the first side surface of the outrigger and contact of the one or more bumpers on the second side of the receiving area with the second side surface of the outrigger serving to guide the collar portion into position relative to the shoulder portion.

10. The combination of claim 9, wherein the engagement portion of the locking includes at least one post portion rotatable from the disengaged position that allows passage of the collar portion over the locking portion to the deployed position that prevents movement of the collar portion relative to the gantry to maintain the position of the collar portion of the surgical table relative to the gantry.

11. A combination of a surgical table, a gantry including surgical robotic arms, and an interface for moveably interconnecting the surgical table with the gantry, the combination comprising: the surgical table comprising a first end, an opposite second end, a first lateral side, an opposite second lateral side, a longitudinal cross-member extending between the first end and the second end, and a patient support portion being configured to support a patient thereon; the gantry comprising: a base portion provided on an operating room floor; an extension portion extending outwardly relative to the base portion; a support portion supported relative to the base portion, the support portion having a first portion on a first side of the gantry, and a second portion on a second side of the gantry; a first surgical robotic arm, a second surgical robotic arm, and a third surgical robotic arm of the surgical robotic arms, the first surgical robotic arm supported by the first portion of the gantry, the second surgical robotic arm supported by the second portion of the gantry, and the third surgical robotic arm supported by the extension portion, the first surgical robotic arm, the second surgical robotic arm, and the third surgical robotic arm each including a first end portion for supporting surgical equipment thereon; and the interface comprising: a collar portion attached relative to the longitudinal cross-member of the surgical table, the collar portion including a first end, an opposite second end, and an interior cavity extending between the first end and the second end, portions of the longitudinal cross member being received in the interior cavity; an actuator portion actuatable to facilitate movement of the longitudinal cross-member relative to the collar portion; and a locking portion attached to and/or supported relative to the gantry, and at least one engagement portion moveable between a disengaged position and an engaged position to maintain a position of the collar portion of the surgical table relative to the gantry; wherein, after the collar portion is maintained in position relative to the gantry by the interface, an actuation of the actuator portion drives movement of portions of cross member into and out of the interior cavity to correspondingly adjust positions of the surgical table relative to the gantry, and relative to the first surgical robotic arm, the second surgical robotic arm, and the third surgical robotic arm supported by the gantry; and wherein, after the collar portion is maintained in position relative to the gantry, the first surgical robotic arm and the second surgical robotic arm are supported by the gantry above the patient supported by the surgical table, the third surgical arm is supported by the gantry below the patient supported by the surgical table, the surgical equipment supported by the first surgical robotic arm, the second surgical robotic arm, and the third surgical robotic arm are moveable within at least a first plane transverse to a cranial-caudal axis of the patient supported by the patient support portion of the surgical table, and as the positions of the surgical table are adjusted relative to the gantry via actuation of the actuator portion, portions of the patient supported by the patient support portion are configured to be moved into and out of the first plane to thereby creating a three-dimensional operational area in which the first surgical robotic arm, the second surgical robotic arm, and the third surgical robotic arm are configured to access the patient and/or areas around the patient.

12. The combination of claim 11, wherein, after the collar portion is maintained in position relative to the gantry, the surgical equipment supported by the first surgical robotic arm is positionable relative to one of a first lateral side and a second lateral side of the patient supported in a prone position on the patient support portion, and the surgical equipment supported by the second surgical robotic arm is positionable relative to the other of the first lateral side and the second lateral side of the patient supported in the prone position on the patient support portion.

13. The combination of claim 11, wherein the collar portion includes an exterior surface and the gantry includes a shoulder portion, and the exterior surface is contacted to the shoulder portion, when the collar portion is maintained in position relative to the gantry by the interface.

14. The combination of claim 13, wherein, when the collar portion is maintained in position relative to the gantry by the interface, the collar portion is position between the shoulder portion and the least one engagement portion of the locking portion in the engaged position.

15. The combination of claim 11, wherein the actuator portion is one of attached to the collar portion and attached to and/or supported by the gantry, the actuator portion including a first gear portion being configured to operatively engage a second gear portion attached to the cross member.

16. The combination of claim 11, wherein the interface includes an outrigger portion attached to and/or supported relative to the gantry, the outrigger portion including a first side surface and a second side surface; and wherein the collar portion includes a receiving area defined in part by one or more bumpers attached to the collar portion on a first side of the receiving area and one or more bumpers attached to the collar portion on a second side of the receiving area, the outrigger portion being receivable in the receiving area, and contact of the one or more bumpers on the first side of the receiving area with the first side surface of the outrigger and contact of the one or more bumpers on the second side of the receiving area with the second side surface of the outrigger serving to guide the collar portion into position relative to the shoulder portion.

17. The combination of claim 16, wherein the engagement portion of the locking includes at least one post portion rotatable from the undeployed position that allows passage of the collar portion over the locking portion to the deployed position that prevents movement of the collar portion relative to the gantry to maintain the position of the collar portion of the surgical table relative to the gantry.

18. A combination of a surgical table, a gantry including surgical robotic arms, and an interface for moveably interconnecting the surgical table with the gantry, the combination comprising: the surgical table comprising a first end, an opposite second end, a first lateral side, an opposite second lateral side, a longitudinal cross-member extending between the first end and the second end, and a patient support portion being configured to support a patient thereon; the gantry comprising: a base portion provided on an operating room floor; an extension portion extending outwardly relative to the base portion; a support portion supported relative to the base portion; a first surgical robotic arm and a second surgical robotic arm of the surgical robotic arms, the first surgical robotic arm supported by the support portion of the gantry, and the second surgical robotic arm supported by the extension portion, the first surgical robotic arm and the second surgical robotic arm each including a first end portion for supporting surgical equipment thereon; and the interface comprising: a collar portion attached relative to the longitudinal cross-member of the surgical table, the collar portion including a first end, an opposite second end, and an interior cavity extending between the first end and the second end, portions of the longitudinal cross member being received in the interior cavity; an actuator portion actuatable to facilitate movement of the longitudinal cross-member relative to the collar portion; and a locking portion attached to and/or supported relative to the gantry, and at least one engagement portion moveable between a disengaged position and an engaged position to maintain a position of the collar portion of the surgical table relative to the gantry; wherein, after the collar portion is maintained in position relative to the gantry by the interface, an actuation of the actuator portion drives movement of portions of cross member into and out of the interior cavity to correspondingly adjust positions of the surgical table relative to the gantry, and relative to the first surgical robotic arm and the second surgical robotic arm supported by the gantry; and wherein, after the collar portion is maintained in position relative to the gantry, the first surgical robotic arm is supported by the gantry above the patient supported by the surgical table, the second surgical arm is supported by the gantry below the patient supported by the surgical table, the surgical equipment supported by the first surgical robotic arm and the second surgical robotic arm are moveable within at least a first plane transverse to a cranial-caudal axis of the patient supported by the patient support portion of the surgical table, and as the positions of the surgical table are adjusted relative to the gantry via actuation of the actuator portion, portions of the patient supported by the patient support portion are configured to be moved into and out of the first plane thereby creating a three-dimensional operational area in which the first surgical robotic arm and the second surgical robotic arm are configured to access the patient and/or areas around the patient.

19. The combination of claim 18, wherein, after the collar portion is maintained in position relative to the gantry, the surgical equipment supported by the first surgical robotic arm is positionable relative to one of a first lateral side and a second lateral side of a posterior portion of the patient supported in a prone position on the patient support portion, and the surgical equipment supported by the second surgical robotic arm is positionable relative to one of a first lateral side and a second lateral side of an anterior portion of the patient supported in the prone position on the patient support portion.

20. The combination of claim 18, wherein the posterior portion and the anterior portion of the patient supported by the patient support portion are simultaneously accessible by the first surgical robotic arm and the second surgical robotic arm, respectively.

* * * * *